US012209241B2

(12) United States Patent
Leonov et al.

(10) Patent No.: US 12,209,241 B2
(45) Date of Patent: Jan. 28, 2025

(54) VIRUS LIKE PARTICLE

(71) Applicants: The University of Leeds, Leeds (GB); The University of York, York (GB)

(72) Inventors: German Leonov, London (GB); Simon White, Mansfield, CT (US); Peter Stockley, Leeds (GB); Nikesh Patel, Leeds (GB); Emma Wroblewski, Leeds (GB); Dan Maskell, Leeds (GB); Reidun Twarock, York (GB); Richard Bingham, York (GB); Eva Weiss, York (GB); Eric Dykeman, York (GB)

(73) Assignees: The University of Leeds, Leeds (GB); The University of York, York (GB)

(\*) Notice: Subject to any disclaimer, the term of this patent is extended or adjusted under 35 U.S.C. 154(b) by 279 days.

(21) Appl. No.: 16/617,098

(22) PCT Filed: May 31, 2018

(86) PCT No.: PCT/GB2018/051475
§ 371 (c)(1),
(2) Date: Nov. 26, 2019

(87) PCT Pub. No.: WO2018/220371
PCT Pub. Date: Dec. 6, 2018

(65) Prior Publication Data
US 2020/0165613 A1    May 28, 2020

(30) Foreign Application Priority Data
Jun. 1, 2017   (GB) ..................................... 1708709

(51) Int. Cl.
*C12N 15/113*   (2010.01)
*A61K 39/00*   (2006.01)
(Continued)

(52) U.S. Cl.
CPC ...... *C12N 15/1131* (2013.01); *C12N 15/8283* (2013.01); *A61K 39/292* (2013.01);
(Continued)

(58) Field of Classification Search
None
See application file for complete search history.

(56) References Cited

U.S. PATENT DOCUMENTS

2003/0211996 A1\*  11/2003  Gowans ................... C12N 7/00
                                                          424/277.1
2014/0255439 A1   9/2014  Leclerc et al.

FOREIGN PATENT DOCUMENTS

CN      103687942 A    3/2014
WO   WO 2005/014836 A2   2/2005
(Continued)

OTHER PUBLICATIONS

Protzer U, Nassal M, Chiang PW, Kirschfink M, Schaller H. Interferon gene transfer by a hepatitis B virus vector efficiently suppresses wild-type virus infection. Proc Natl Acad Sci U S A. Sep. 14, 1999;96(19): 10818-23. doi: 10.1073/pnas.96.19.10818. PMID: 10485909; PMCID: PMC17966. (Year: 1999).\*

(Continued)

*Primary Examiner* — Michelle S Horning
(74) *Attorney, Agent, or Firm* — Klarquist Sparkman, LLP

(57) ABSTRACT

The disclosure relates to the assembly of Virus Like Particles [VLPs] using packaging native and artificial packaging signals and their use in vaccines and immunological compositions and the methods of vaccination or immunisation against human and animal viral pathogens.

Figure 1A:
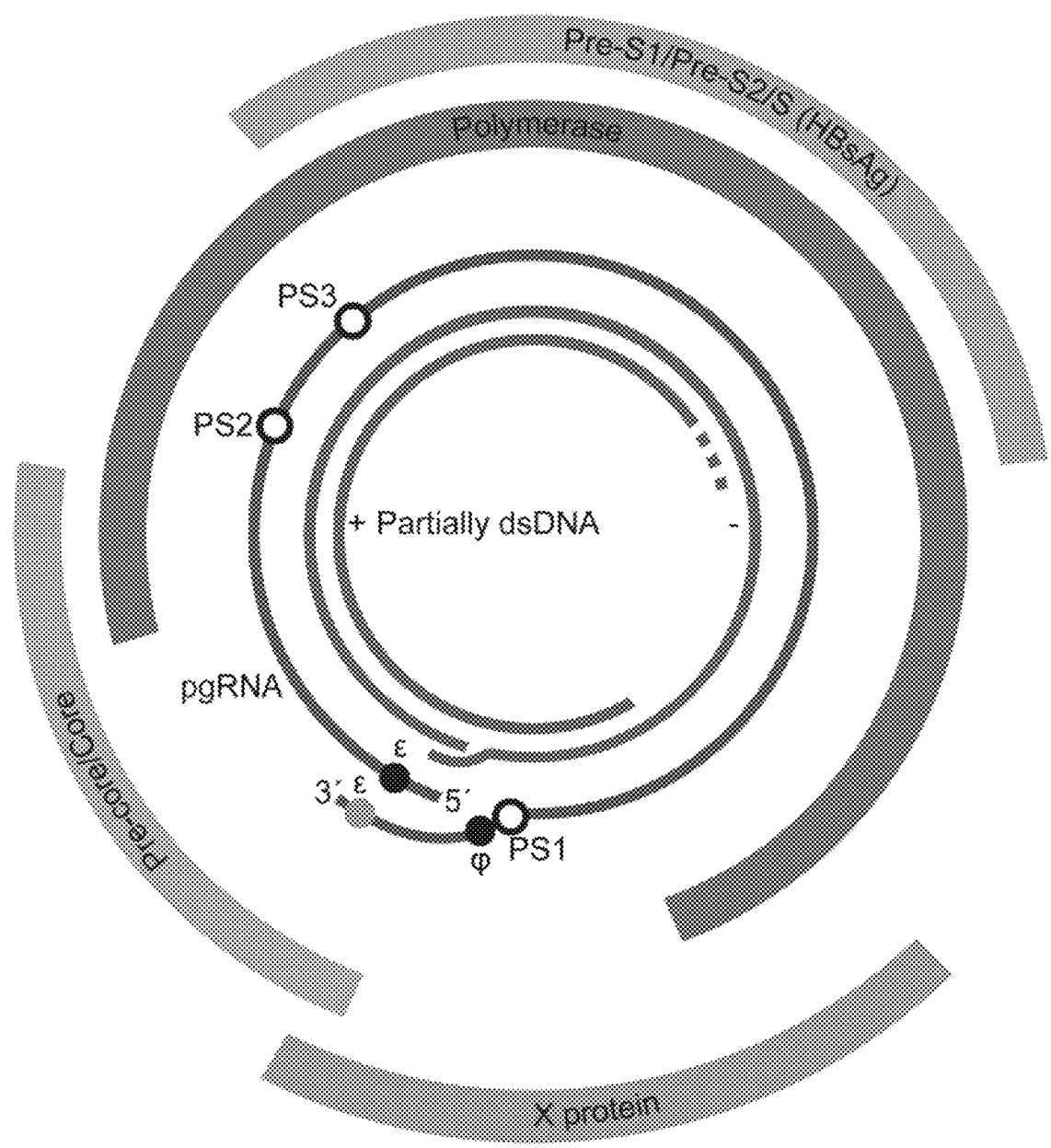

32 Claims, 42 Drawing Sheets
Specification includes a Sequence Listing.

(51) Int. Cl.
*A61K 39/29* (2006.01)
*C12N 15/82* (2006.01)
(52) U.S. Cl.
CPC .. *A61K 2039/5258* (2013.01); *C12N 2310/11* (2013.01); *C12N 2310/14* (2013.01); *C12N 2310/531* (2013.01)

(56) References Cited

FOREIGN PATENT DOCUMENTS

| WO | WO 2006/135413 A2 | | 12/2006 | |
|---|---|---|---|---|
| WO | WO 2014093965 | * | 6/2014 | ........... C07K 14/005 |
| WO | WO 2015/033155 A1 | | 3/2015 | |

OTHER PUBLICATIONS

Feng H, Beck J, Nassal M, Hu KH. A SELEX-screened aptamer of human hepatitis B virus RNA encapsidation signal suppresses viral replication. PLoS One. 2011;6(11):e27862. doi: 10.1371/journal.pone.0027862. Epub Nov. 18, 2011. PMID: 22125633; PMCID: PMC3220704. (Year: 2011).*
Dykeman et al., "Solving a Levinthal's paradox for virus assembly identifies a unique antiviral strategy," *Proceedings Natl Academy Sciences* 111:5361-66, 2014.
Ford et al., "Sequence-specific, RNA-protein interactions overcome electrostatic barriers preventing assembly of satellite tobacco necrosis virus coat protein," *J Mol Biol.* 425:1050-1064, 2013.
Patel et al., "HBV RNA pre-genome encodes specific motifs that mediate interactions with the viral core protein that promote nucleocapsid assembly," *Nat Microbiol.* 2:17098, 2017.
Prevelige et al., "Follow the Yellow Brick Road: A Paradigm Shift in Virus Assembly," *J Mol Biol.* 428:416-418, 2015.
Rolfsson et al., "Direct Evidence for Packaging Signal-Mediated Assembly of Bacteriophage MS2," *J Mol Biol.* 428:431-448, 2015.
Stewart et al., "Identification of novel RNA secondary structures within the hepatitis C virus genome reveals a cooperative involvement in genome packaging," *Scientific Reports* 6:1-10, 2016.
International Search Report for International Application No. PCT/GB2018/051475 Mailed on Aug. 13, 2018 (17 pages).
Search Report for GB 1708709.9 mailed on Mar. 7, 2018 (4 pages).

* cited by examiner

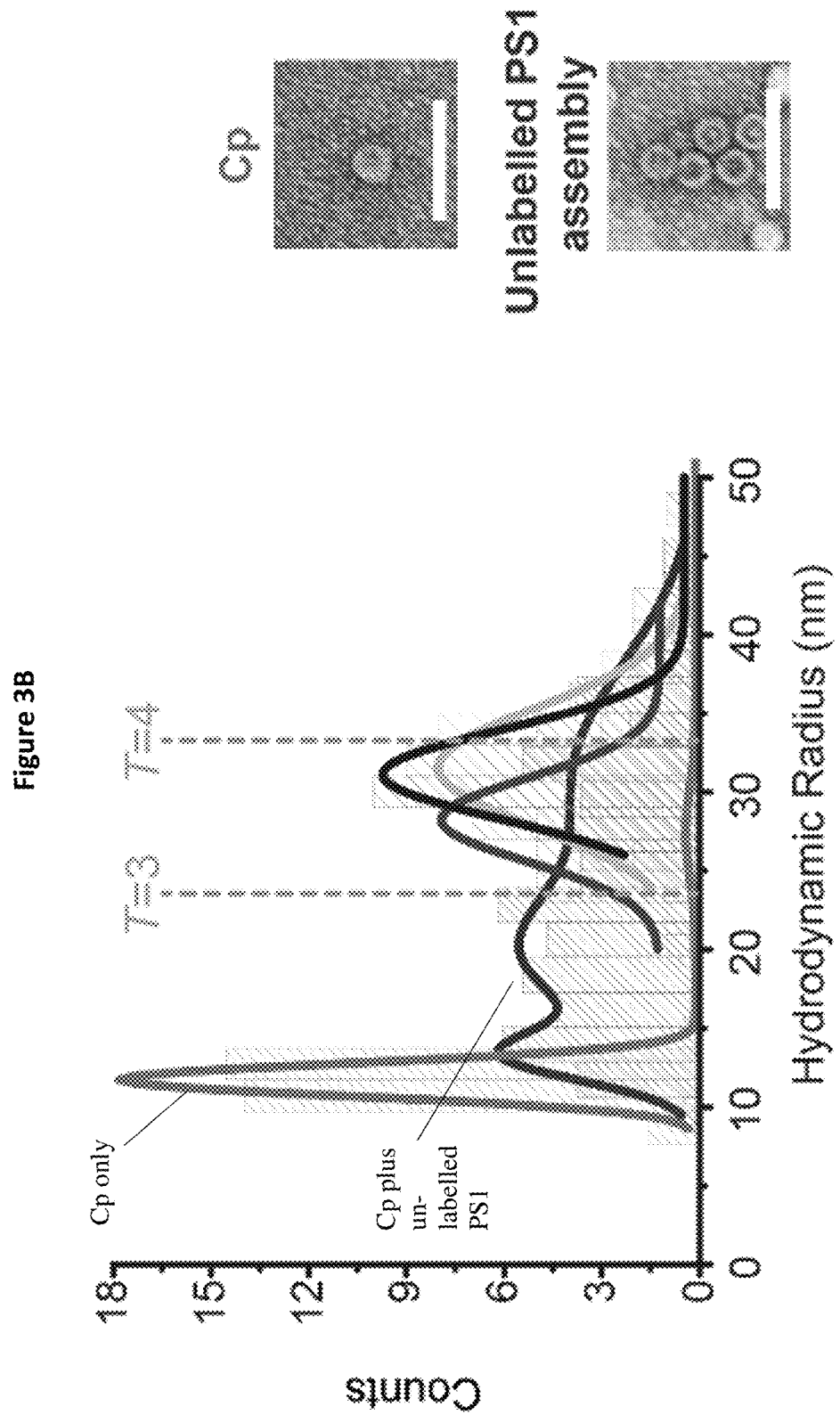

Figure 4A
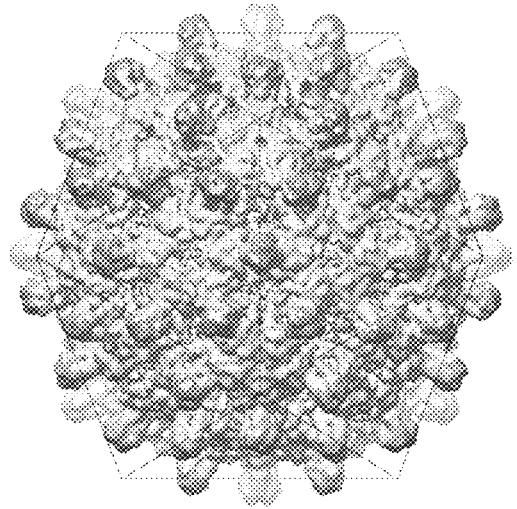
T=3 @ 5.6 Å
Figure 4B
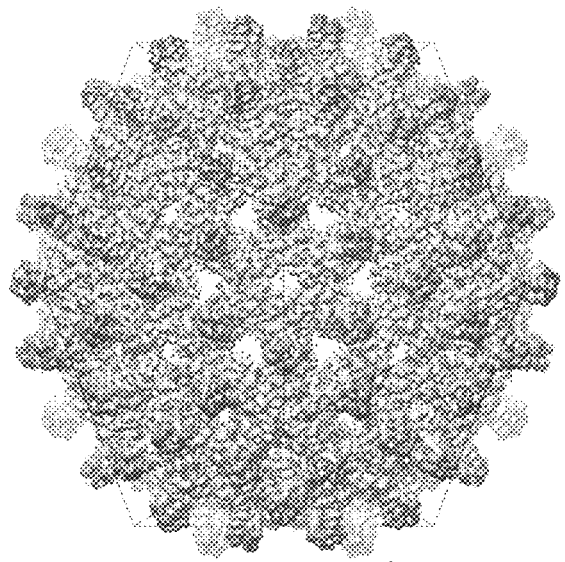
T=4 @ 4.7Å
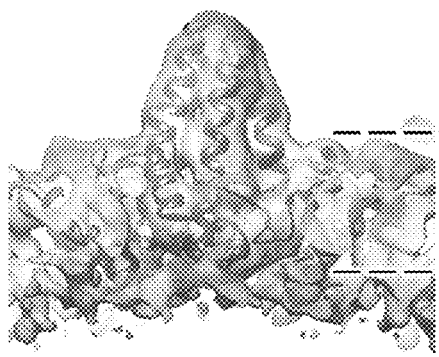
Figure 4C
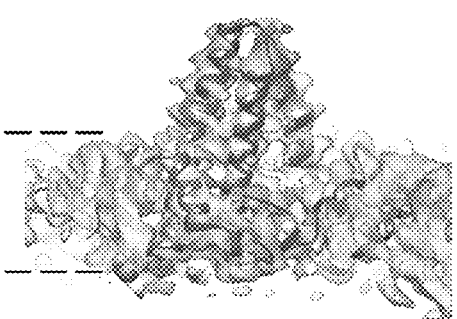
Figure 4D

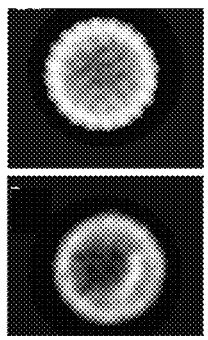
Figure 5A
Figure 5B
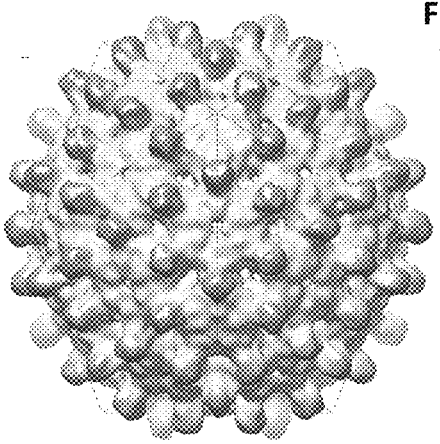
Figure 5C
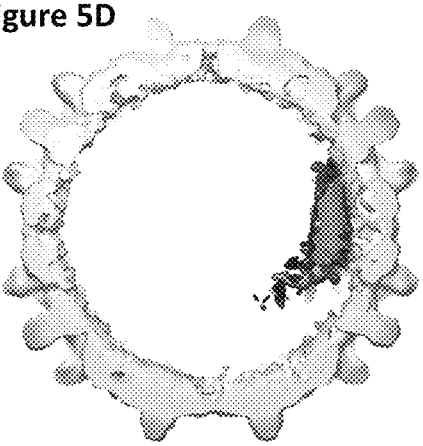
Figure 5D
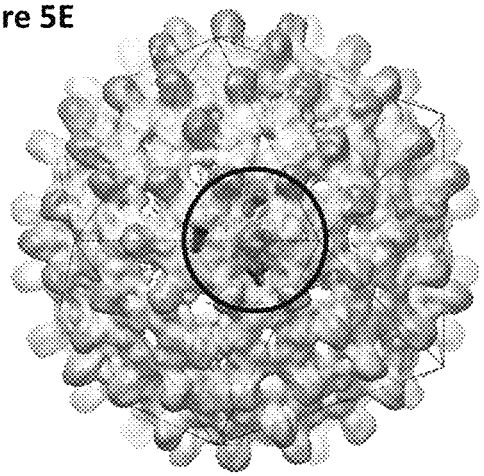
Figure 5E
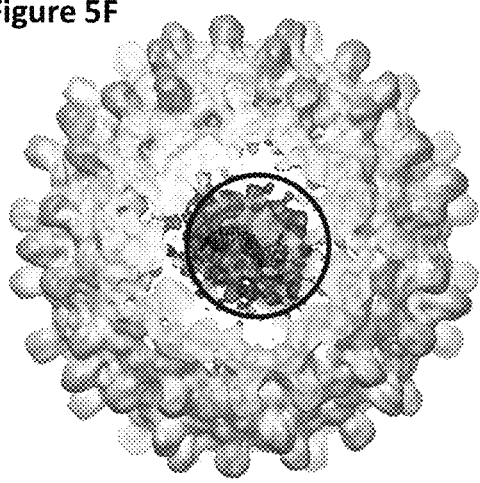
Figure 5F
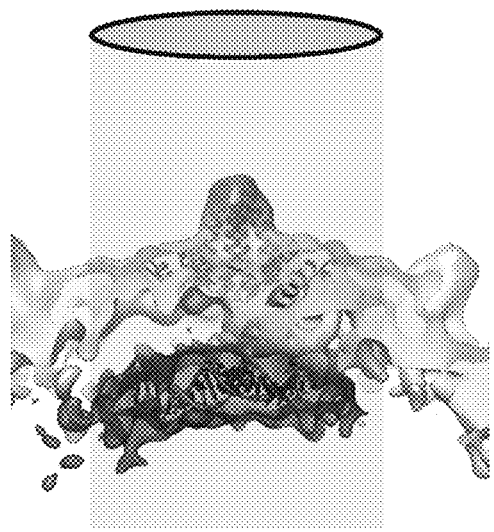
Figure 5G
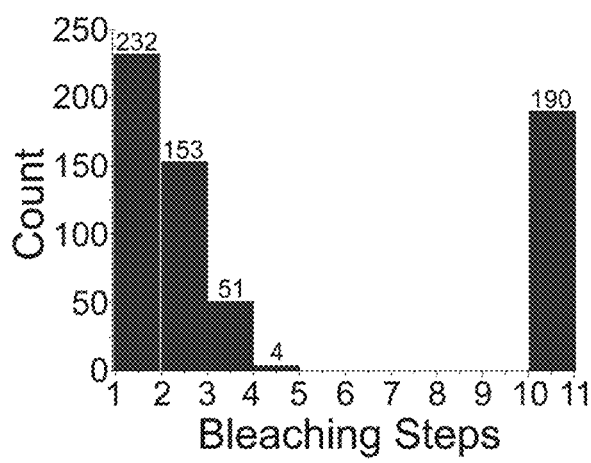
Figure 5H

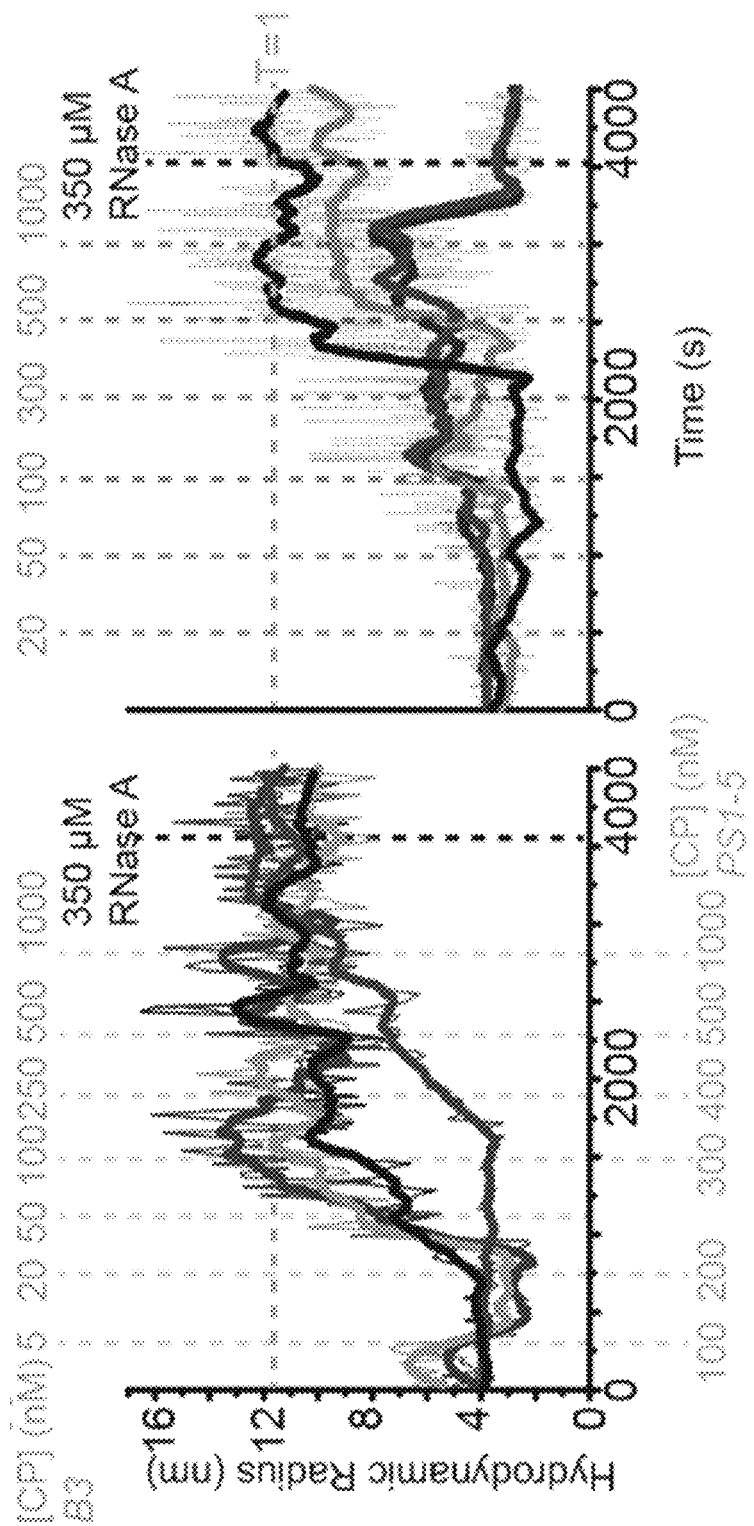

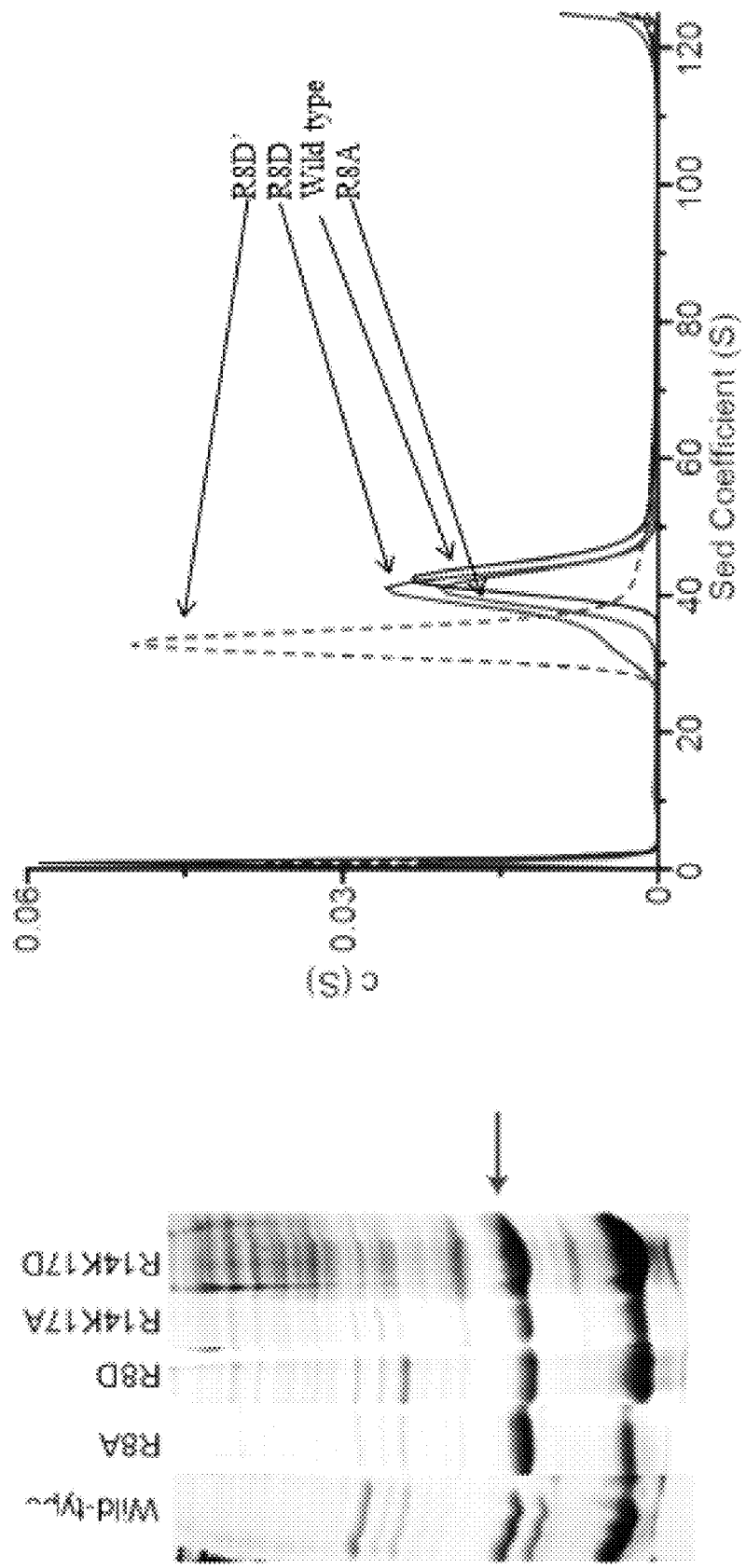

Figure 19A
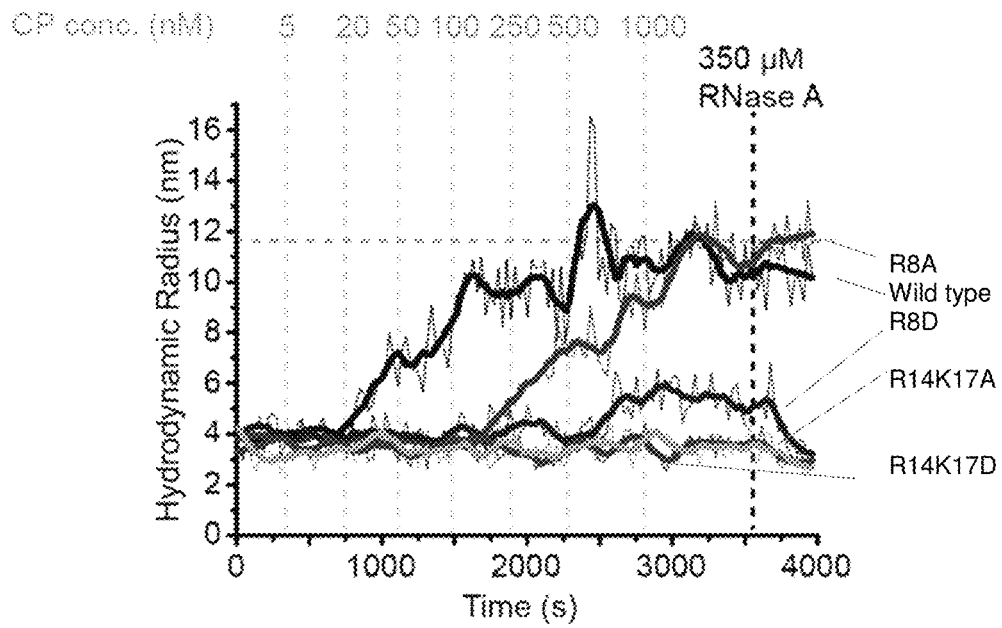
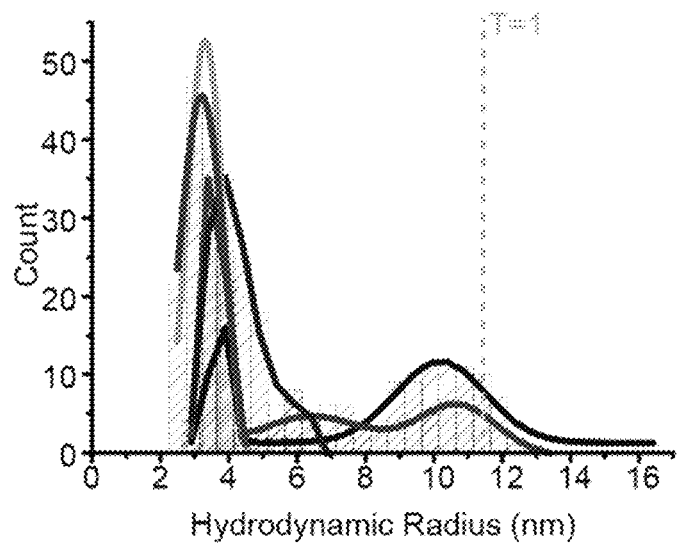
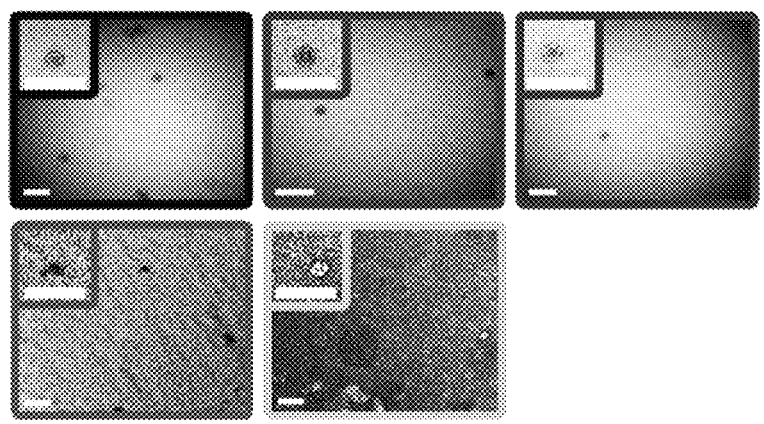

Figure 19B
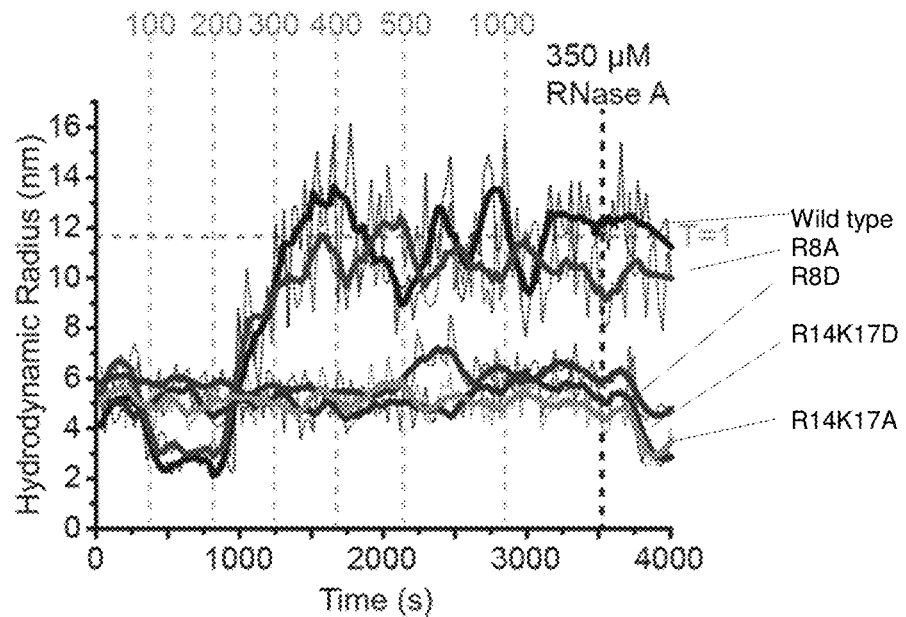
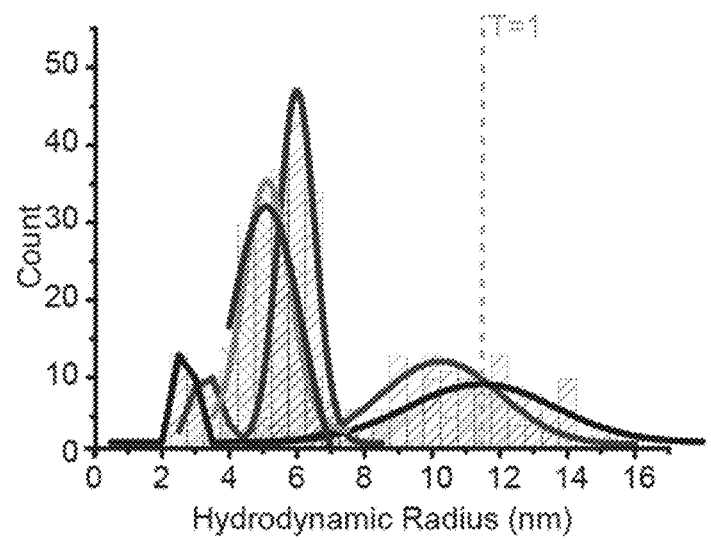
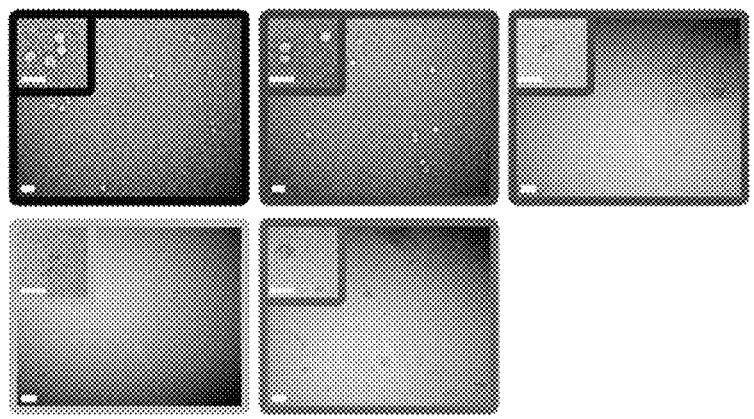

SEQUENCE LISTING

<160> NUMBER OF SEQ ID NOS: 72

<210> SEQ ID NO 1
<211> LENGTH: 35
<212> TYPE: RNA
<213> ORGANISM: artificial sequence
<220> FEATURE:
<223> OTHER INFORMATION: Packaging signal

<400> SEQUENCE: 1
guuuguuuaa agacugggag gaguuggggg aggag                              35

<210> SEQ ID NO 2
<211> LENGTH: 49
<212> TYPE: RNA
<213> ORGANISM: artificial sequence
<220> FEATURE:
<223> OTHER INFORMATION: Packaging signal

<400> SEQUENCE: 2
gggcccucug acaguuaaug aaaaaaggag auuaaaauua auuaugccu               49

<210> SEQ ID NO 3
<211> LENGTH: 34

-continued

```
<212> TYPE: RNA
<213> ORGANISM: artificial sequence
<220> FEATURE:
<223> OTHER INFORMATION: Packaging signal

<400> SEQUENCE: 3
ggcuggcauu cuauauaaga gagaaacuac acgc                              34

<210> SEQ ID NO 4
<211> LENGTH: 59
<212> TYPE: RNA
<213> ORGANISM: artificial sequence
<220> FEATURE:
<223> OTHER INFORMATION: Packaging signal

<400> SEQUENCE: 4
cugggaggag uuggggagg agauuagguu aaaggucuuu guacuaggag gcuguaggc    59

<210> SEQ ID NO 5
<211> LENGTH: 135
<212> TYPE: RNA
<213> ORGANISM: artificial sequence
<220> FEATURE:
<223> OTHER INFORMATION: Packaging signal

<400> SEQUENCE: 5
gggcugcccu caaggaccag ggcagaaaag aggaaaagaa aagugacaga acacuuauaa  60
ggaaaaaacg uacaaacguu uuaaggaaaa aaggaagcug caauagcgca aggaauccga  120
aaauucggaa aggaa                                                  135

<210> SEQ ID NO 6
<211> LENGTH: 129
<212> TYPE: RNA
<213> ORGANISM: artificial sequence
<220> FEATURE:
<223> OTHER INFORMATION: Packaging signal

<400> SEQUENCE: 6
gggcugcccu caaggaccag ggcagaaaag aggaaaagaa aagugacaga acacuuauaa  60
ggaaccacac aagugaagg aaaaaaggaa gcugcaauag cgcaaggaau ccgaaaauuc   120
ggaaaggaa                                                         129

<210> SEQ ID NO 7
<211> LENGTH: 129
<212> TYPE: RNA
<213> ORGANISM: artificial sequence
<220> FEATURE:
<223> OTHER INFORMATION: Packaging signal

<400> SEQUENCE: 7
gggcugcccu caaggaccag ggcagaaaag aggaaaagaa aagugacaga acacuuauaa  60
ggaaccacac aaguauaagg aaaaaaggaa gcugcaauag cgcaaggaau ccgaaaauuc  120
ggaaaggaa                                                         129

<210> SEQ ID NO 8
<211> LENGTH: 140
<212> TYPE: RNA
<213> ORGANISM: artificial sequence
<220> FEATURE:
<223> OTHER INFORMATION: Packaging signal

<400> SEQUENCE: 8
```

```
gggcccccgca acaaugcggg gaaggaagga aggaagaaaa cguacaaacg uuuuaaggaa    60
caacgcaaca augcguugaa ggaaggaagg aagggggcgua caaacgcccc aaggaauuuu   120
gcaacaaugc aaaaaaggaa                                                140
```

<210> SEQ ID NO 9
<211> LENGTH: 11
<212> TYPE: RNA
<213> ORGANISM: artificial sequence
<220> FEATURE:
<223> OTHER INFORMATION: nucleotide binding motif

<400> SEQUENCE: 9

```
gaaaaaagga g                                                          11
```

<210> SEQ ID NO 10
<211> LENGTH: 18
<212> TYPE: RNA
<213> ORGANISM: artificial sequence
<220> FEATURE:
<223> OTHER INFORMATION: B3 sequence variants

<400> SEQUENCE: 10

```
acaugcaaca augcacac                                                   18
```

<210> SEQ ID NO 11
<211> LENGTH: 18
<212> TYPE: RNA
<213> ORGANISM: artificial sequence
<220> FEATURE:
<223> OTHER INFORMATION: B3 sequence variants

<400> SEQUENCE: 11

```
acaugcaauu uugcacac                                                   18
```

<210> SEQ ID NO 12
<211> LENGTH: 18
<212> TYPE: RNA
<213> ORGANISM: artificial sequence
<220> FEATURE:
<223> OTHER INFORMATION: B3 sequence variants

<400> SEQUENCE: 12

```
acaugcauuu augcacac                                                   18
```

<210> SEQ ID NO 13
<211> LENGTH: 18
<212> TYPE: RNA
<213> ORGANISM: artificial sequence
<220> FEATURE:
<223> OTHER INFORMATION: B3 sequence variants

<400> SEQUENCE: 13

```
acaugcaguu uugcacac                                                   18
```

<210> SEQ ID NO 14
<211> LENGTH: 18
<212> TYPE: RNA
<213> ORGANISM: artificial sequence
<220> FEATURE:
<223> OTHER INFORMATION: B3 sequence variants

<400> SEQUENCE: 14

```
acaugcauuu gugcacac                                                   18
```

```
<210> SEQ ID NO 15
<211> LENGTH: 18
<212> TYPE: RNA
<213> ORGANISM: artificial sequence
<220> FEATURE:
<223> OTHER INFORMATION: B3 sequence variants

<400> SEQUENCE: 15
acaugcaauu gugcacac                                                   18

<210> SEQ ID NO 16
<211> LENGTH: 18
<212> TYPE: RNA
<213> ORGANISM: artificial sequence
<220> FEATURE:
<223> OTHER INFORMATION: B3 sequence variants

<400> SEQUENCE: 16
acaugcaguu augcacac                                                   18

<210> SEQ ID NO 17
<211> LENGTH: 18
<212> TYPE: RNA
<213> ORGANISM: artificial sequence
<220> FEATURE:
<223> OTHER INFORMATION: B3 sequence variants

<400> SEQUENCE: 17
acaugcaguu gugcacac                                                   18

<210> SEQ ID NO 18
<211> LENGTH: 18
<212> TYPE: RNA
<213> ORGANISM: artificial sequence
<220> FEATURE:
<223> OTHER INFORMATION: B3 sequence variants

<400> SEQUENCE: 18
acaugcaauu augcacac                                                   18

<210> SEQ ID NO 19
<211> LENGTH: 32
<212> TYPE: DNA
<213> ORGANISM: artificial sequence
<220> FEATURE:
<223> OTHER INFORMATION: Primer

<400> SEQUENCE: 19
gacattaata cgactcacta tagggacatg ca                                   32

<210> SEQ ID NO 20
<211> LENGTH: 33
<212> TYPE: DNA
<213> ORGANISM: artificial sequence
<220> FEATURE:
<223> OTHER INFORMATION: Primer

<400> SEQUENCE: 20
gtgtgcataa ttgcatgtcc ctatagtgag tcg                                  33

<210> SEQ ID NO 21
<211> LENGTH: 33
<212> TYPE: DNA
<213> ORGANISM: artificial sequence
<220> FEATURE:
<223> OTHER INFORMATION: Primer
```

```
<400> SEQUENCE: 21
gtgtgcacaa ctgcatgtcc ctatagtgag tcg                           33

<210> SEQ ID NO 22
<211> LENGTH: 33
<212> TYPE: DNA
<213> ORGANISM: artificial sequence
<220> FEATURE:
<223> OTHER INFORMATION: Primer

<400> SEQUENCE: 22
gtgtgcacaa ttgcatgtcc ctatagtgag tcg                           33

<210> SEQ ID NO 23
<211> LENGTH: 33
<212> TYPE: DNA
<213> ORGANISM: artificial sequence
<220> FEATURE:
<223> OTHER INFORMATION: Primer

<400> SEQUENCE: 23
gtgtgcataa ctgcatgtcc ctatagtgag tcg                           33

<210> SEQ ID NO 24
<211> LENGTH: 33
<212> TYPE: DNA
<213> ORGANISM: artificial sequence
<220> FEATURE:
<223> OTHER INFORMATION: Primer

<400> SEQUENCE: 24
gtgtgcataa atgcatgtcc ctatagtgag tcg                           33

<210> SEQ ID NO 25
<211> LENGTH: 33
<212> TYPE: DNA
<213> ORGANISM: artificial sequence
<220> FEATURE:
<223> OTHER INFORMATION: Primer

<400> SEQUENCE: 25
gtgtgcaaaa ttgcatgtcc ctatagtgag tcg                           33

<210> SEQ ID NO 26
<211> LENGTH: 33
<212> TYPE: DNA
<213> ORGANISM: artificial sequence
<220> FEATURE:
<223> OTHER INFORMATION: Primer

<400> SEQUENCE: 26
gtgtgcaaaa ctgcatgtcc ctatagtgag tcg                           33

<210> SEQ ID NO 27
<211> LENGTH: 33
<212> TYPE: DNA
<213> ORGANISM: artificial sequence
<220> FEATURE:
<223> OTHER INFORMATION: Primer

<400> SEQUENCE: 27
gtgtgcacaa atgcatgtcc ctatagtgag tcg                           33

<210> SEQ ID NO 28
<211> LENGTH: 33
```

```
<212> TYPE: DNA
<213> ORGANISM: artificial sequence
<220> FEATURE:
<223> OTHER INFORMATION: Primer

<400> SEQUENCE: 28
gtgtgcatgg ttgcatgtcc ctatagtgag tcg                            33

<210> SEQ ID NO 29
<211> LENGTH: 33
<212> TYPE: DNA
<213> ORGANISM: artificial sequence
<220> FEATURE:
<223> OTHER INFORMATION: Primer

<400> SEQUENCE: 29
gtgtgcattt ttgcatgtcc ctatagtgag tcg                            33

<210> SEQ ID NO 30
<211> LENGTH: 33
<212> TYPE: DNA
<213> ORGANISM: artificial sequence
<220> FEATURE:
<223> OTHER INFORMATION: Primer

<400> SEQUENCE: 30
gtgtgcatcc ttgcatgtcc ctatagtgag tcg                            33

<210> SEQ ID NO 31
<211> LENGTH: 33
<212> TYPE: DNA
<213> ORGANISM: artificial sequence
<220> FEATURE:
<223> OTHER INFORMATION: Primer

<400> SEQUENCE: 31
gtgtgcatca ttgcatgtcc ctatagtgag tcg                            33

<210> SEQ ID NO 32
<211> LENGTH: 33
<212> TYPE: DNA
<213> ORGANISM: artificial sequence
<220> FEATURE:
<223> OTHER INFORMATION: Primer

<400> SEQUENCE: 32
gtgtgcatac ttgcatgtcc ctatagtgag tcg                            33

<210> SEQ ID NO 33
<211> LENGTH: 62
<212> TYPE: DNA
<213> ORGANISM: artificial sequence
<220> FEATURE:
<223> OTHER INFORMATION: Primer

<400> SEQUENCE: 33
agtaatacga ctcactatag gggggctgcc ctcaaggacc agggcagaaa agaggaaaag    60
aa                                                                  62

<210> SEQ ID NO 34
<211> LENGTH: 89
<212> TYPE: DNA
<213> ORGANISM: artificial sequence
<220> FEATURE:
<223> OTHER INFORMATION: Primer
```

<400> SEQUENCE: 34
ggcagaaaag aggaaaagaa aagtgacaga acacttataa ggaaatacac aagtataagg     60
aaaaaaggaa gctgcaatag cgcaaggaa                                       89

<210> SEQ ID NO 35
<211> LENGTH: 41
<212> TYPE: DNA
<213> ORGANISM: artificial sequence
<220> FEATURE:
<223> OTHER INFORMATION: Primer

<400> SEQUENCE: 35
ttcctttccg aattttcgga ttccttgcgc tattgcagct t                         41

<210> SEQ ID NO 36
<211> LENGTH: 54
<212> TYPE: DNA
<213> ORGANISM: artificial sequence
<220> FEATURE:
<223> OTHER INFORMATION: Primer

<400> SEQUENCE: 36 gggcccgca acaatgcggg gaaggaagga aggaagaaaa cgtacaaacg tttt            54

<210> SEQ ID NO 37
<211> LENGTH: 86
<212> TYPE: DNA
<213> ORGANISM: artificial sequence
<220> FEATURE:
<223> OTHER INFORMATION: Primer

<400> SEQUENCE: 37
agaaaacgta caaacgtttt aaggaacaac gcaacaatgc gttgaaggaa ggaaggaagg     60
ggcgtacaaa cgccccaagg aatttt                                          86

<210> SEQ ID NO 38
<211> LENGTH: 45
<212> TYPE: DNA
<213> ORGANISM: artificial sequence
<220> FEATURE:
<223> OTHER INFORMATION: Primer

<400> SEQUENCE: 38 ttccttttt gcattgttgc aaaattcctt ggggcgtttg tacgc                      45

<210> SEQ ID NO 39
<211> LENGTH: 89
<212> TYPE: DNA
<213> ORGANISM: artificial sequence
<220> FEATURE:
<223> OTHER INFORMATION: Primer

<400> SEQUENCE: 39
ggcagaaaag aggaaaagaa aagtgacaga acacttataa ggaaccacac aagtggaagg     60
aaaaaaggaa gctgcaatag cgcaaggaa                                       89

<210> SEQ ID NO 40
<211> LENGTH: 95
<212> TYPE: DNA
<213> ORGANISM: artificial sequence
<220> FEATURE:
<223> OTHER INFORMATION: Primer

<400> SEQUENCE: 40

```
ggcagaaaag aggaaaagaa aagtgacaga acacttataa ggaaaaaacg uacaaacguu    60
uuaaggaaaa aaggaagctg caatagcgca aggaa                              95
```

<210> SEQ ID NO 41
<211> LENGTH: 61
<212> TYPE: DNA
<213> ORGANISM: artificial sequence
<220> FEATURE:
<223> OTHER INFORMATION: Primer

<400> SEQUENCE: 41

```
agtaatacga ctcactatag ggagtaaaga caggaaactt tactgactaa catggcaaaa    60
c                                                                   61
```

<210> SEQ ID NO 42
<211> LENGTH: 80
<212> TYPE: DNA
<213> ORGANISM: artificial sequence
<220> FEATURE:
<223> OTHER INFORMATION: Primer

<400> SEQUENCE: 42

```
actgactaac atggcaaaac aacagaacaa caggcgaaaa tccgcaacaa tgcgtgcagt    60
gaagcgcatg ataaatacac                                               80
```

<210> SEQ ID NO 43
<211> LENGTH: 45
<212> TYPE: DNA
<213> ORGANISM: artificial sequence
<220> FEATURE:
<223> OTHER INFORMATION: Primer

<400> SEQUENCE: 43

```
tcagtgcaaa cctttatgc tccaagtgtg tatttatcat gcgct                    45
```

<210> SEQ ID NO 44
<211> LENGTH: 61
<212> TYPE: DNA
<213> ORGANISM: artificial sequence
<220> FEATURE:
<223> OTHER INFORMATION: Primer

<400> SEQUENCE: 44

```
agtaatacga ctcactatag ggagtaaaga caggaaactt tactgactaa catggcaaaa    60
c                                                                   61
```

<210> SEQ ID NO 45
<211> LENGTH: 41
<212> TYPE: DNA
<213> ORGANISM: artificial sequence
<220> FEATURE:
<223> OTHER INFORMATION: Primer

<400> SEQUENCE: 45

```
actgactaac atggcaaaac aacagaacaa caggcgaaaa t                       41
```

<210> SEQ ID NO 46
<211> LENGTH: 28
<212> TYPE: DNA
<213> ORGANISM: artificial sequence
<220> FEATURE:
<223> OTHER INFORMATION: Primer

<400> SEQUENCE: 46
cgcattgttg cggattttcg cctgttgt                                    28

<210> SEQ ID NO 47
<211> LENGTH: 52
<212> TYPE: DNA
<213> ORGANISM: artificial sequence
<220> FEATURE:
<223> OTHER INFORMATION: Primer

<400> SEQUENCE: 47
agtaatacga ctcactatag ggtggcaaaa caacagaaca acaggcgaaa at         52

<210> SEQ ID NO 48
<211> LENGTH: 57
<212> TYPE: DNA
<213> ORGANISM: artificial sequence
<220> FEATURE:
<223> OTHER INFORMATION: Primer

<400> SEQUENCE: 48
aacagaacaa caggcgaaaa tccgcaacaa tgcgtgcagt gaagcgcatg ataaata    57

<210> SEQ ID NO 49
<211> LENGTH: 45
<212> TYPE: DNA
<213> ORGANISM: artificial sequence
<220> FEATURE:
<223> OTHER INFORMATION: Primer

<400> SEQUENCE: 49
ccaagtgtgt atttatcatg cgcttcactg cacgcattgt tgcgg                 45

<210> SEQ ID NO 50
<211> LENGTH: 35
<212> TYPE: DNA
<213> ORGANISM: artificial sequence
<220> FEATURE:
<223> OTHER INFORMATION: Primer

<400> SEQUENCE: 50
agtaatacga ctcactatag ggccgcaaca atgcg                            35

<210> SEQ ID NO 51
<211> LENGTH: 39
<212> TYPE: DNA
<213> ORGANISM: artificial sequence
<220> FEATURE:
<223> OTHER INFORMATION: Primer

<400> SEQUENCE: 51
ccgcaacaat gcgtgcagtg aagcgcatga taaatacac                        39

<210> SEQ ID NO 52
<211> LENGTH: 45
<212> TYPE: DNA
<213> ORGANISM: artificial sequence
<220> FEATURE:
<223> OTHER INFORMATION: Primer

<400> SEQUENCE: 52
tcagtgcaaa cctttatgc tccaagtgtg tatttatcat gcgct                  45

<210> SEQ ID NO 53
<211> LENGTH: 56

```
<212> TYPE: PRT
<213> ORGANISM: artificial sequence
<220> FEATURE:
<223> OTHER INFORMATION: HBV CP

<400> SEQUENCE: 53

Pro Ala Tyr Arg Pro Pro Asn Ala Pro Ile Leu Ser Thr Leu Pro Glu
1               5                   10                  15

Thr Thr Val Val Arg Arg Arg Asp Arg Gly Arg Ser Pro Arg Arg Arg
            20                  25                  30

Thr Pro Ser Pro Arg Arg Arg Arg Ser Gln Ser Pro Arg Arg Arg Arg
        35                  40                  45

Ser Gln Ser Arg Glu Ser Gln Cys
    50                  55

<210> SEQ ID NO 54
<211> LENGTH: 10
<212> TYPE: RNA
<213> ORGANISM: artificial sequence
<220> FEATURE:
<223> OTHER INFORMATION: loop sequences

<400> SEQUENCE: 54
agguaggagc                                                              10

<210> SEQ ID NO 55
<211> LENGTH: 47
<212> TYPE: RNA
<213> ORGANISM: artificial sequence
<220> FEATURE:
<223> OTHER INFORMATION: HBV PS-PS1

<400> SEQUENCE: 55
ggguuuuggg uuuguuuaaa gacuggagga guuggggag gagcccc                       47

<210> SEQ ID NO 56
<211> LENGTH: 47
<212> TYPE: RNA
<213> ORGANISM: artificial sequence
<220> FEATURE:
<223> OTHER INFORMATION: HBV PS-PS2

<400> SEQUENCE: 56
ggguuuuggg gugacaguua augaaaaaag gagauuaaaa uuacccc                      47

<210> SEQ ID NO 57
<211> LENGTH: 47
<212> TYPE: RNA
<213> ORGANISM: artificial sequence
<220> FEATURE:
<223> OTHER INFORMATION: HBV PS-PS3

<400> SEQUENCE: 57
ggguuuuggg gcuggcauuc uauauaagag agaaacuaca cgccccc                      47

<210> SEQ ID NO 58
<211> LENGTH: 61
<212> TYPE: RNA
<213> ORGANISM: artificial sequence
<220> FEATURE:
<223> OTHER INFORMATION: HBV PS-Epsilon

<400> SEQUENCE: 58
uguucauguc cuacuguuca agccuccaag cugugccuug gguggcuuug gggcauggac        60
``` a                                                               61

<210> SEQ ID NO 59
<211> LENGTH: 25
<212> TYPE: PRT
<213> ORGANISM: artificial sequence
<220> FEATURE:
<223> OTHER INFORMATION: STNV CP

<400> SEQUENCE: 59

Glu Leu His Thr Asn Ile Met Arg Lys Val Ala Arg Met Thr Ala Ser
1               5                   10                  15

Lys Arg Arg Asn Asn Gln Gln Lys Ala
            20                  25

<210> SEQ ID NO 60
<211> LENGTH: 30
<212> TYPE: RNA
<213> ORGANISM: artificial sequence
<220> FEATURE:
<223> OTHER INFORMATION: B3

<400> SEQUENCE: 60
ccuuuucaag acaugcaaca augcacacag                                30

<210> SEQ ID NO 61
<211> LENGTH: 127
<212> TYPE: RNA
<213> ORGANISM: artificial sequence
<220> FEATURE:
<223> OTHER INFORMATION: PS1-5

<400> SEQUENCE: 61
gaguaaagac aggaaacuuu acugacuaac auggcaaaac aacagaacaa caggcgaaaa     60
uccgcaacaa ugcgugcagu gaagcgcaug auaaauacac acuuggagca uaaaagguuu    120
gcacuga                                                             127

<210> SEQ ID NO 62
<211> LENGTH: 129
<212> TYPE: RNA
<213> ORGANISM: artificial sequence
<220> FEATURE:
<223> OTHER INFORMATION: stable PS3

<400> SEQUENCE: 62
gggcugcccu caaggaccag ggcagaaaag aggaaaagaa aagugacaga acacuuauaa     60
ggaaccacac aaguggaagg aaaaaaggaa gcugcaauag cgcaaggaau ccgaaaauuc    120
ggaaaggaa                                                           129

<210> SEQ ID NO 63
<211> LENGTH: 140
<212> TYPE: RNA
<213> ORGANISM: artificial sequence
<220> FEATURE:
<223> OTHER INFORMATION: all PS3

<400> SEQUENCE: 63 gggcccccgca acaaugcggg gaaggaagga aggaagaaaa cguacaaacg uuuuaaggaa     60
caacgcaaca augcguugaa ggaaggaagg aaggggcgua caaacgcccc aaggaauuuu    120
gcaacaaugc aaaaaaggaa                                                140

```
<210> SEQ ID NO 64
<211> LENGTH: 18
<212> TYPE: RNA
<213> ORGANISM: artificial sequence
<220> FEATURE:
<223> OTHER INFORMATION: inner variants

<400> SEQUENCE: 64
acaugcaacc augcacac                                                     18

<210> SEQ ID NO 65
<211> LENGTH: 18
<212> TYPE: RNA
<213> ORGANISM: artificial sequence
<220> FEATURE:
<223> OTHER INFORMATION: inner variants

<400> SEQUENCE: 65
acaugcaaaa augcacac                                                     18

<210> SEQ ID NO 66
<211> LENGTH: 18
<212> TYPE: RNA
<213> ORGANISM: artificial sequence
<220> FEATURE:
<223> OTHER INFORMATION: inner variants

<400> SEQUENCE: 66
acaugcaagg augcacac                                                     18

<210> SEQ ID NO 67
<211> LENGTH: 18
<212> TYPE: RNA
<213> ORGANISM: artificial sequence
<220> FEATURE:
<223> OTHER INFORMATION: inner variants

<400> SEQUENCE: 67
acaugcaaug augcacac                                                     18

<210> SEQ ID NO 68
<211> LENGTH: 18
<212> TYPE: RNA
<213> ORGANISM: artificial sequence
<220> FEATURE:
<223> OTHER INFORMATION: inner variants

<400> SEQUENCE: 68
acaugcaagu augcacac                                                     18

<210> SEQ ID NO 69
<211> LENGTH: 73
<212> TYPE: RNA
<213> ORGANISM: artificial sequence
<220> FEATURE:
<223> OTHER INFORMATION: PS1-3

<400> SEQUENCE: 69
aguaaagaca ggaaacuuua cugacuaaca uggcaaaaca acagaacaac aggcgaaaau       60
ccgcaacaau gcg                                                          73

<210> SEQ ID NO 70
<211> LENGTH: 65
<212> TYPE: RNA
<213> ORGANISM: artificial sequence
<220> FEATURE:
```

-continued

```
<223> OTHER INFORMATION: PS2-4

<400> SEQUENCE: 70
aacaacagaa caacaggcga aaauccgcaa caaugcgugc agugaagcgc augauaaaua    60
cacac                                                                65

<210> SEQ ID NO 71
<211> LENGTH: 66
<212> TYPE: RNA
<213> ORGANISM: artificial sequence
<220> FEATURE:
<223> OTHER INFORMATION: PS3-5

<400> SEQUENCE: 71
ccgcaacaau gcgugcagug aagcgcauga uaaauacaca cuuggagcau aaaagguuug    60
cacuga                                                               66

<210> SEQ ID NO 72
<211> LENGTH: 129
<212> TYPE: RNA
<213> ORGANISM: artificial sequence
<220> FEATURE:
<223> OTHER INFORMATION: unstable PS3

<400> SEQUENCE: 72
gggcugcccu caaggaccag ggcagaaaag aggaaaagaa aagugacaga acacuuauaa    60
ggaaccacac aaguauaagg aaaaaaggaa gcugcaauag cgcaaggaau ccgaaaauuc   120
ggaaaggaa                                                           129
```

VIRUS LIKE PARTICLE

CROSS REFERENCE TO RELATED APPLICATIONS

This is the U.S. National Stage of International Application No. PCT/GB2018/051475, filed May 31, 2018, which was published in English under PCT Article 21(2), which in turn claims the benefit of Great Britain Application No. 1708709.9, filed Jun. 1, 2017.

FIELD OF THE INVENTION

The disclosure relates to the assembly of Virus Like Particles [VLPs] using native and artificial nucleic acid packaging signals and their use in vaccines, immunological and pharmaceutical compositions; methods of vaccination or immunisation against human and animal viral pathogens and also as a delivery vehicle for therapeutic agents such as pharmaceutical proteins, siRNAs or gene therapy vectors or diagnostic agents.

BACKGROUND OF THE INVENTION

Viruses cause various debilitating diseases in humans and animals with often detrimental effects or even death. Viral infections cause a huge financial burden to the healthcare systems around the world, and also result in vast losses of animal related products, such as in the meat or dairy industries.

In contrast to bacterial infections which can be treated with antibiotic agents after the infections starts, prevention of viral infections is typically the preferred route as there are often no effective anti-viral drug options available. Vaccination is the most effective form of disease prevention and has been successfully developed for some viral diseases such as influenza, polio, measles and Human Papilloma Virus [HPV]. Vaccination is the administration of antigenic material to stimulate an individual's immune system to develop adaptive immunity to a pathogen. The active agent of a vaccine may be, for example, an inactivated form of the pathogen, a highly immunogenic component of the pathogen or in the form of a weakened so called attenuated virus. However, all these different types of vaccines vary in their effectiveness and safety record and moreover can often be unsuitable for administration to immune compromised subjects, pregnant women or children.

Inactivated vaccines are made from viruses which have been killed through physical or chemical processes. These types of vaccines are very safe, as they cannot cause disease because they lack infectious genetic material, and are therefore suitable for immune compromised subjects. However, such inactivated vaccines are often ineffective in inducing an appropriate or long lasting immune response, and therefore frequently require multiple administration steps. Vaccines containing highly immunogenic components of the pathogen, so called subunit vaccines, provide similar benefits to the inactivated vaccines such as a high safety record as they do not contain live components of the virus which can cause disease. However, effective immune responses are not guaranteed, and even if a response is elicited, immunological memory, providing protection against the desired pathogen for a prolonged period, may not be achieved.

Alternatively, live attenuated vaccines can be used. Live attenuated vaccines comprise weakened pathogens which although still capable of replication in the host organism cause no or a very mild disease. Vaccinations using an attenuated virus result in excellent protection; however, they are intrinsically less safe when compared to inactivated or subunit vaccines since they can revert to their original more virulent form and cause disease. Therefore attenuated vaccines are unsuitable for subjects with compromised immune systems, can harm the unborn child when given during pregnancy and have an increased potential for immunisation errors by health professionals such as e.g. reconstitution errors of lyophilised attenuated pathogens which, when given in a higher dose, are more potent. Moreover, attenuated vaccines are less stable than inactivated vaccines and require sophisticated logistics to maintain cold storage and transport to maintain the, although weakened, activity. This is of particular concern in third world countries with a less established health system.

Attenuated vaccines are common and are available for a variety of diseases such as measles, mumps, rubella, chicken pox, smallpox and polio. Most of the live attenuated vaccines in use today are derived from serial passage in cultured cells such as for example fibroblasts or and chicken embryos, resulting in a gradual loss of virulence. This method relies on the random accumulation of point mutations to confer avirulence and is time consuming and inefficient. Other methods to produce attenuated viral strains are based on genetic engineering and are disclosed in application WO2005/012535.

Virus-like particles (VLPs) comprise multiple capsid proteins that mimic the conformation of native viruses but lack the viral DNA or RNA and thus are unable to replicate in a host cell. The use of VLPs as a tool for the production of safe and efficient vaccines has been recognised and some VPL-based vaccines against human papilloma virus have been developed. U.S. Pat. No. 8,062,642 discloses the production of papillomavirus capsid proteins and VLPs with antigenic characteristics similar to those of native infectious virus. Similarly, WO9913056 discloses methods of disassembly of papilloma VLPs.

Despite the enormous success of the types of vaccines listed above they are in general very difficult to prepare/formulate with the desired properties and in many viruses their natural antigenic variation across circulating populations means that these strategies are not viable in these cases.

The present disclosure relates to the formation of VLPs using nucleic acid packaging signals derived from viruses and the design of nucleic acid cassettes comprising native and/or artificial packaging signals that provide a substrate for artificial VLP assembly and the use of artificial VLPs as vaccines and in the delivery of agents to cells, for example therapeutic or diagnostic agents. The knowledge of the RNA packaging signal-mediated assembly mechanisms of positive-sense, single-stranded (ss) RNA viruses has enabled the identification of the critical properties of their genomic RNA molecules with respect to being assembly substrates, allowing the production of artificial, efficient RNA substrates for the efficient assembly of VLPs. The latter have similar properties to the natural virions formed by viruses. In particular, artificial VLP capsids retain the native immunological properties of those viruses as well as their cell tropism. They also retain many of the stability and mechanical properties of the original virus particle. VLPs have utility in a wide range of applications in relation to the cell specific delivery of agents and as safe, attenuated vaccines and vectors for targeted delivery of drugs and in gene therapy.

STATEMENTS OF THE INVENTION

According to an aspect of the invention there is provided an artificial nucleic acid cassette for use in the assembly of a virus like particle comprising: one or more packaging signals, wherein the more than one packaging signals are arranged in series and separated by nucleic acid, said packaging signals composed of a nucleic acid loop domain comprising a nucleotide binding motif for cognate viral capsid protein(s), and a nucleic acid stem domain consisting of a double stranded region by intramolecular base pairing, wherein said artificial nucleic acid cassette, when contacted with a plurality of cognate viral capsid proteins, assembles said cognate viral capsid proteins into a VLP that protects said nucleic acid packaging signals contained within said VLP from ribonuclease digestion.

In a preferred embodiment of the invention said artificial nucleic acid cassette is a non-replicating nucleic acid.

In a preferred embodiment of the invention said VLP provokes an immune response similar to an immune response of the native virus particle when administered to an animal subject.

In a further preferred embodiment of the invention said artificial nucleic acid cassette is not a native virus particle.

In a preferred embodiment of the invention said artificial nucleic acid cassette does not comprise protein encoding nucleic acid.

In a preferred embodiment of the invention said artificial nucleic acid cassette comprises at least two nucleic acid packaging signals.

Preferably, said artificial nucleic acid cassette comprises at least 2, 3, 4, 5, 6, 7, 8, 9 or at least 10 nucleic acid packaging signals.

In a preferred embodiment of the invention said artificial nucleic acid cassette comprises at least 1 nucleic acid packaging signal.

In a preferred embodiment of the invention said artificial nucleic acid cassette comprises at least 2 nucleic acid packaging signals.

In a preferred embodiment of the invention said artificial nucleic acid cassette comprises at least 3 nucleic acid packaging signals.

In a preferred embodiment of the invention said artificial nucleic acid cassette comprises at least 4 nucleic acid packaging signals In an alternative preferred embodiment of the invention said artificial nucleic acid cassette comprises at least 5 nucleic acid packaging signals.

In a preferred embodiment of the invention said non-coding viral nucleic acid separating said nucleic acid packaging signals is at least 5 nucleotides in length.

In a preferred embodiment of the invention said non-coding viral nucleic acid separating said nucleic acid packaging signals is at least between 5 and 50 nucleotides in length. Preferably, greater than 50 nucleotides.

In a preferred embodiment of the invention said loop domain comprising said capsid binding motif is at least 4 nucleotides in length. Preferably, said loop domain is at least 5, 6, 7 or 8 nucleotides in length.

In a preferred embodiment of the invention said stem domain is at least 4 base pairs (bp) in length. Preferably said stem domain is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 61, 62, 63, 64, 65, 66, 67, 68, 69, or at least 70 bp in length.

In a preferred embodiment of the invention said artificial nucleic acid cassette is at least 50 nucleotides in length. Preferably said nucleic acid cassette is between 50 and 1000 nucleotides in length.

In a preferred embodiment of the invention said artificial nucleic acid cassette is at least 50, 60, 70, 80, 90, 100, 110, 120, 130, 140, 150, 200, 250, 300, 350, 400, 450, 500, 550, 600, 650, 700, 750, 800, 850, 900, 950 or at least 1000 or nucleotides in length.

In a preferred embodiment of the invention said nucleic acid packaging signal is isolated from an RNA virus; preferably said RNA virus is a human pathogen.

Preferably said packaging signal is a modified packaging signal that retains the characteristic nucleotide recognition motif and spacing between packaging signals but alters stability of/stabilises individual packaging signals.

Several diseases in humans, animals and plants are caused by so called RNA viruses. Single-stranded RNA viruses are divided into three groups: Positive-sense ssRNA viruses (Group IV), negative-sense ssRNA viruses (Group V) and retroviruses (Group VI). On infection, the viral RNA enters the host cells and, dependent on the type of virus, RNA is directly translated (Group IV) into the viral proteins necessary for replication or is, prior to translation, transcribed into a more suitable form of RNA by an RNA-dependent RNA polymerase (Group V). Group VI RNA viruses utilise a virally encoded reverse transcriptase to produce DNA from the RNA genome, which is often integrated into the host genome and so replicated and transcribed by the host. Non-limiting examples of positive-sense ssRNA viruses include hepatitis C, West Nile virus, Dengue virus, Zika virus, SARS and MERS coronavirus and rhinovirus. Negative sense ssRNA viruses include, by example, Ebola virus, measles, mumps, influenza and hepatitis D virus. Retroviruses of the genus Lentivirus include Human Immune deficiency virus I and II and Hepatitis B virus. Examples of zoonotic viral pathogens include Ebola virus, Rabies virus and influenza A virus. Non-limiting examples of plant ssRNA viruses include Turnip Crinkle Virus, Cowpea Chlorotic Mottle Virus 1, 2 and 3, Brome Mosaic Virus 1, 2 and 3, and Satellite Tobacco Necrosis Virus. In our co-pending application U.S. Ser. No. 14/916,945, the content of which is incorporated by reference in its entirety, and in particular the packaging signals and mimetic aptamers disclosed therein, are disclosed packaging signals for a range of ssRNA viruses.

In a preferred embodiment of the invention said RNA virus is a positive sense single stranded RNA virus.

In a preferred embodiment of the invention said nucleic acid packaging signal RNA virus is isolated from Hepatitis B virus.

In a preferred embodiment of the invention said Hepatitis B virus packaging signal comprises a nucleotide binding motif wherein said nucleotide binding motif comprises the nucleotide sequence RGAG wherein R is either G or A.

In a preferred embodiment of the invention said artificial nucleic acid cassette comprises at least one, two or three Hepatitis B virus packaging signals wherein one or more of said nucleic acid packaging signals includes the nucleotide binding motif RGAG.

In a preferred embodiment of the invention said nucleic acid cassette comprises at least one of the PSs identified for Hepatitis B wherein each of said nucleic acid packaging signals includes the binding motif RGAG.

In a preferred embodiment of the invention said artificial nucleic acid cassette comprises a nucleotide sequence selected from the group consisting of:

i) a nucleic acid molecule comprising a nucleotide sequence GUUUGUUUAAAGACUGGGAG-GAGUUGGGGGAGGAG [SEQ ID NO: 1];

ii) a nucleic acid molecule comprising a nucleotide sequence that is at least 25% identical to the nucleotide sequence set forth in SEQ ID NO: 1 and that comprises a nucleotide binding motif GGGAGG.

In a further preferred embodiment of the invention said artificial nucleic acid cassette comprises a nucleotide sequence selected from the group:
i) a nucleic acid molecule comprising a nucleotide sequence GGGCCCUCUGACAGUUAAUGAAAAAGGAGAUUAAA AUUAAUUAUGCCU [SEQ ID NO: 2];
ii) a nucleic acid molecule comprising a nucleotide sequence that is at least 25% identical to the nucleotide sequence set forth in SEQ ID NO: 2 and that comprises a nucleotide binding motif GAAAAAAGGAG (SEQ ID NO 9).

In a further preferred embodiment of the invention said artificial nucleic acid cassette comprises a nucleotide sequence selected from the group:
i) a nucleic acid molecule comprising a nucleotide sequence GGCUGGCAUUCUAUAUAAGAGAGAAACUACACGC [SEQ ID NO: 3];
ii) a nucleic acid molecule comprising a nucleotide sequence that is at least 25% identical to the nucleotide sequence set forth in SEQ ID NO: 3 and that comprises a nucleotide binding motif AUAUAAGAG.

In a preferred embodiment of the invention said artificial nucleic acid cassette comprises a nucleotide sequence that is at least 30%, 35%, 40%, 45%, 55%, 60%, 70%, 75%, 80%, 85%, 90%, 95%, 96%, 97%, 98% or 99% identical to the nucleotide sequence set forth in SEQ ID NO: 1 and/or SEQ ID NO: 2 and/or SEQ ID NO: 3.

In a preferred embodiment of the invention said artificial nucleic acid cassette comprises a nucleotide sequence comprising SEQ ID NO: 1 and/or SEQ ID NO: 2 and/or SEQ ID NO: 3.

In a preferred embodiment of the invention said artificial nucleic acid cassette comprises a nucleotide sequence comprising SEQ ID 4: CUGGGAGGAGUUGGGGGAGGAGAUUAGGUUAAAGGUCUUUGUACUAGGAGGCUGU AGGC In an alternative embodiment of the invention said RNA virus is a zoonotic species that infects of a human subject.

In a further alternative embodiment of the invention said RNA virus is a species that infects a veterinary animal subject.

In a further alternative embodiment of the invention said RNA virus is a species that infects a plant cell or plant.

In a preferred embodiment of the invention said RNA virus is Satellite Tobacco Necrosis Virus.

In a preferred embodiment of the invention said nucleic acid cassette comprises at least one nucleic acid packaging signal isolated from Satellite Tobacco Necrosis Virus.

In a preferred embodiment of the invention said nucleic acid cassette comprises at least one nucleic acid packaging signal wherein said nucleic acid packaging signal comprises the nucleotide binding motif AXXA or AXXXA wherein X is any nucleotide base.

In a preferred embodiment of the invention said artificial nucleic acid cassette comprises a nucleotide sequence selected from the group:
i) a nucleic acid molecule comprising a nucleotide sequence set forth in SEQ ID NO: 5;
ii) a nucleic acid molecule comprising a nucleotide sequence that is at least 25% identical to the nucleotide sequence set forth in SEQ ID NO: 5 [GGGCUGCCCUCAAGGACCAGGGCAGAAAAGAGGAAAAGAAAAGUGACAGAACACUUAUAAGGAAAAAA CGUACAAACGUUUUAAGGAAAAAAGGAAGCUGCAAUAGCGCAAGGAAUCCGAAAAUUCGGAAAGGAA] and that comprises a nucleotide binding motif AXXA.

In a preferred embodiment of the invention said artificial nucleic acid cassette comprises a nucleotide sequence selected from the group:
i) a nucleic acid molecule comprising a nucleotide sequence set forth in SEQ ID NO: 6 [GGGCUGCCCUCAAGGACCAGGGCAGAAAAGAGGAAAAGAAAAGUGACAGAACACUUAUAAGGAACCACACAAGUGGAAGGAAAAAAGGAAGCUGCAAUAGCGCAAGGAAUCCGAA AAUUCGGAAAGGAA]
ii) a nucleic acid molecule comprising a nucleotide sequence that is at least 25% identical to the nucleotide sequence set forth in SEQ ID NO: 6 and that comprises a nucleotide binding motif AXXA.

In a preferred embodiment of the invention said artificial nucleic acid cassette comprises a nucleotide sequence selected from the group:
i) a nucleic acid molecule comprising a nucleotide sequence set forth in SEQ ID NO: 7 [GGGCUGCCCUCAAGGACCAGGGCAGAAAAGAGGAAAAGAAAAGUGACAGAACACUUAUAAGGAACCACACAAGUAUAAGGAAAAAAGGAAGCUGCAAUAGCGCAAGGAAUCCGAA AAUUCGGAAAGGAA]
ii) a nucleic acid molecule comprising a nucleotide sequence that is at least 25% identical to the nucleotide sequence set forth in SEQ ID NO: 7 and that comprises a nucleotide binding motif AXXA.

In a preferred embodiment of the invention said artificial nucleic acid cassette comprises a nucleotide sequence selected from the group:
i) a nucleic acid molecule comprising a nucleotide sequence set forth in SEQ ID NO: 8 [GGGCCCCGCAACAAUGCGGGGAAGGAAGGAAGGAAGAAAACGUACAAACGUUUUAAG GAACAACGCAACAAUGCGUUGAAGGAAGGAAGGAAGGGGCGUACAAACGCCCCAAGGAAUUUUGCAACAAUGCAAAAAAGGAA]
ii) a nucleic acid molecule comprising a nucleotide sequence that is at least 25% identical to the nucleotide sequence set forth in SEQ ID NO: 8 and that comprises a nucleotide binding motif AXXA.

In a preferred embodiment of the invention said artificial nucleic acid cassette comprises a nucleotide sequence that is at least 30%, 35%, 40%, 45%, 55%, 60%, 70%, 75%, 80%, 85%, 90%, 95%, 96%, 97%, 98% or 99% identical to the nucleotide sequence set forth in SEQ ID NO: 5, SEQ ID NO: 6, SEQ ID NO: 7 or SEQ ID NO: 8.

In a preferred embodiment of the invention said artificial nucleic acid cassette further comprises a transcription cassette comprising a nucleic acid molecule adapted to transcribe a nucleic acid encoding a polypeptide or a functional RNA.

In a preferred embodiment of the invention said adaptation is the provision of a promoter sequence and termination sequence to enable expression of said nucleic acid molecule encoding said polypeptide or functional RNA.

In a preferred embodiment of the invention said polypeptide is a therapeutic polypeptide, for example an antibody or antibody fragment.

Antibody fragments include nucleic acids encoding single chain antibody fragments. Antibodies include nucleic acid molecules encoding humanised and chimeric antibodies, prepared according to conventional methodology. Chimeric antibodies are recombinant antibodies in which all of the V-regions of a mouse or rat antibody are combined with human antibody C-regions. Humanised antibodies are recombinant hybrid antibodies which fuse the complementarity determining regions from a rodent antibody V-region with the framework regions from the human antibody V-regions. The C-regions from the human antibody are also used. The complementarity determining regions (CDRs) are the regions within the N-terminal domain of both the heavy and light chain of the antibody to where the majority of the variation of the V-region is restricted. These regions form loops at the surface of the antibody molecule. These loops provide the binding surface between the antibody and antigen.

In an alternative embodiment of the invention said functional nucleic acid is an mRNA encoding a therapeutic polypeptide, an antisense oligonucleotide or a siRNA.

A technique to specifically ablate gene function which has broad acceptance is through the introduction of double-stranded RNA, also referred to as small inhibitory or interfering RNA (siRNA), into a cell which results in the destruction of mRNA complementary to the sequence included in the siRNA molecule. The siRNA molecule comprises two complementary strands of RNA (a sense strand and an antisense strand) annealed to each other to form a double-stranded RNA molecule. The siRNA molecule is typically derived from exons of the gene which is to be ablated. Many organisms respond to the presence of double-stranded RNA by activating a cascade that leads to the formation of siRNA. The presence of double-stranded RNA activates a protein complex comprising RNase III which processes the double-stranded RNA into smaller fragments (siRNAs, approximately 21-29 nucleotides in length) which become part of a ribonucleoprotein complex. The siRNA acts as a guide for the RNase complex to cleave mRNA complementary to the antisense strand of the siRNA thereby resulting in destruction of the mRNA.

According to a further aspect of the invention there is provided a virus like particle comprising an artificial nucleic acid cassette according to the invention.

In a preferred embodiment of the invention said virus like particle is immunogenic when administered to a subject. Preferably said virus like particle provokes an immune response similar to an immune response to the cognate native virus.

In a preferred embodiment of the invention said immune response is induction of an antibody response wherein said antibody response induces antibodies that specifically bind native virus particles.

In a preferred embodiment of the invention said virus like particle retains or has enhanced cell tropism when compared to native virus particles.

According to a further aspect of the invention there is provided a vaccine or immunogenic composition comprising a virus like particle according to the invention.

In a preferred embodiment of the invention said vaccine or immunogenic composition further comprises an adjuvant and/or carrier.

Adjuvants (immune potentiators or immunomodulators) have been used for decades to improve the immune response to vaccine antigens. The incorporation of adjuvants into vaccine formulations is aimed at enhancing, accelerating and prolonging the specific immune response to vaccine antigens. Advantages of adjuvants include the enhancement of the immunogenicity of weaker antigens, the reduction of the antigen amount needed for a successful immunisation, the reduction of the frequency of booster immunisations needed and an improved immune response in elderly and immunocompromised vaccinees. Selectively, adjuvants can also be employed to optimise a desired immune response, e.g. with respect to immunoglobulin classes and induction of cytotoxic or helper T lymphocyte responses. In addition, certain adjuvants can be used to promote antibody responses at mucosal surfaces. Aluminium hydroxide and aluminium or calcium phosphate have been used routinely in human vaccines. More recently, antigens incorporated into IRIV's (immunostimulating reconstituted influenza virosomes) and vaccines containing the emulsion-based adjuvant MF59 have been licensed in countries. Adjuvants can be classified according to their source, mechanism of action and physical or chemical properties. The most commonly described adjuvant classes are gel-type, microbial, oil-emulsion and emulsifier-based, particulate, synthetic and cytokines. More than one adjuvant may be present in the final vaccine product. They may be combined together with a single antigen or all antigens present in the vaccine, or each adjuvant may be combined with one particular antigen. The origin and nature of the adjuvants currently being used or developed is highly diverse. For example, aluminium based adjuvants consist of simple inorganic compounds, PLG is a polymeric carbohydrate, virosomes can be derived from disparate viral particles, MDP is derived from bacterial cell walls; saponins are of plant origin, squalene is derived from shark liver and recombinant endogenous immunomodulators are derived from recombinant bacterial, yeast or mammalian cells. There are several adjuvants licensed for veterinary vaccines, such as mineral oil emulsions that are too reactive for human use. Similarly, complete Freund's adjuvant, although being one of the most powerful adjuvants known, is not suitable for human use.

The term carrier is construed in the following manner. A carrier is an immunogenic molecule which, when bound to a second molecule augments immune responses to the latter. Some antigens are not intrinsically immunogenic yet may be capable of generating antibody responses when associated with a foreign protein molecule such as keyhole-limpet haemocyanin or tetanus toxoid. Such antigens contain B-cell epitopes but no T cell epitopes. The protein moiety of such a conjugate (the "carrier" protein) provides T-cell epitopes which stimulate helper T-cells that in turn stimulate antigen-specific B-cells to differentiate into plasma cells and produce antibody against the antigen.

According to a further aspect of the invention there is provided a pharmaceutical composition comprising a virus like particle according to the invention and including a pharmaceutically acceptable excipient.

When administered the compositions of the present invention are administered in pharmaceutically acceptable preparations. Such preparations may routinely contain pharmaceutically acceptable concentrations of salt, buffering agents, preservatives, compatible carriers and supplementary therapeutic agents'. The compositions of the invention can be administered by any conventional route, including injection or by gradual infusion over time. The administration may, for example, intravenous, intraperitoneal, intramuscular, intracavity, subcutaneous, transdermal or transepithelial.

The compositions of the invention are administered in effective amounts. An "effective amount" is that amount of an agent that alone, or together with further doses, produces the desired response. In the case of treating a disease, the desired response is inhibiting the progression of the disease. This may involve only slowing the progression of the disease temporarily, although more preferably, it involves halting the progression of the disease permanently. This can be monitored by routine methods. Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The compositions used in the foregoing methods preferably are sterile and contain an effective amount of an agent according to the invention for producing the desired response in a unit of weight or volume suitable for administration to a patient. The doses of agent administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, doses of nucleic acid therapeutics such as siRNA and antisense RNA are between 1 nM-1 mM. Preferably doses can range from 1 nM-500 nM, 5 nM-200 nM, and 10 nM-100 nM.

Other protocols for the administration of compositions will be known to one of ordinary skill in the art, in which the dose amount, schedule of injections, sites of injections, mode of administration and the like vary from the foregoing. The administration of compositions to mammals other than humans, (e.g. for testing purposes or veterinary therapeutic purposes), is carried out under substantially the same conditions as described above. A subject, as used herein, is a mammal, preferably a human, and including a non-human primate, cow, horse, pig, sheep, goat, dog, cat or rodent.

When administered, the compositions of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents' (e.g. those typically used in the treatment of the specific disease indication). When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The pharmaceutical compositions containing agents according to the invention may contain suitable buffering agents, including: acetic acid in a salt; citric acid in a salt; boric acid in a salt; and phosphoric acid in a salt. The pharmaceutical compositions also may contain, optionally, suitable preservatives, such as: benzalkonium chloride; chlorobutanol; parabens and thimerosal.

The compositions may conveniently be presented in unit dosage form and may be prepared by any of the methods well-known in the art of pharmacy. All methods include the step of bringing the active agent into association with a carrier which constitutes one or more accessory ingredients. Compositions containing agents according to the invention may be administered as aerosols and inhaled. Compositions suitable for parenteral administration conveniently comprise a sterile aqueous or non-aqueous preparation of agent, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butanediol. Among the acceptable solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, PA.

According to a further aspect of the invention there is provided a virus like particle according to the invention for use in the delivery of an agent to a cell.

According to an aspect of the invention there is provided a method to vaccinate or immunise a subject to prevent or treat a viral infection comprising administering an effective amount of a virus like particle according to the invention.

Throughout the description and claims of this specification, the words "comprise" and "contain" and variations of the words, for example "comprising" and "comprises", means "including but not limited to", and is not intended to (and does not) exclude other moieties, additives, components, integers or steps. "Consisting essentially" means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Figures 1B, 1C:
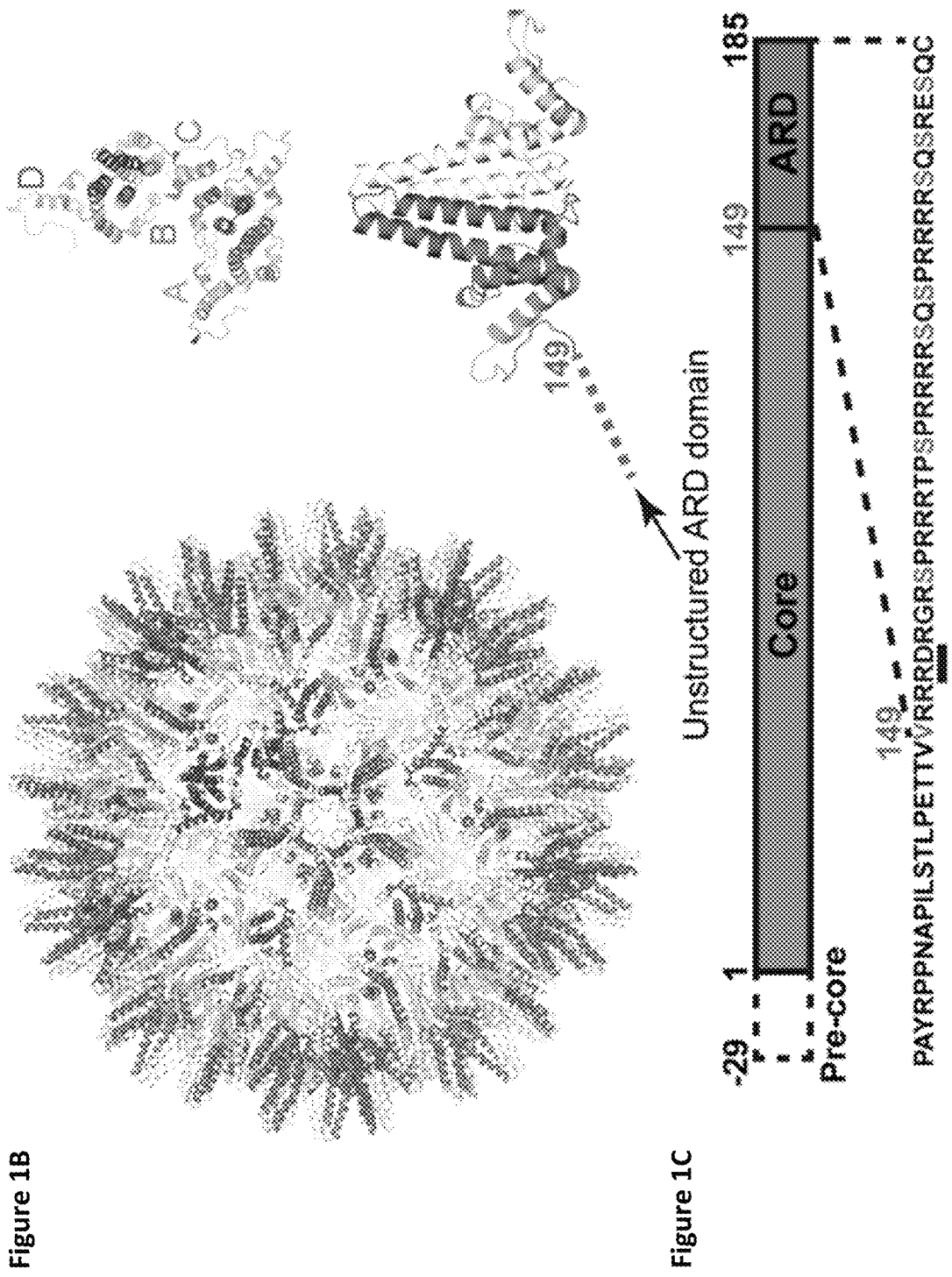

An embodiment of the invention will now be described by example only and with reference to the following figures:

FIG. 1A-1C The Hepatitis B Virus

Figure 2A:
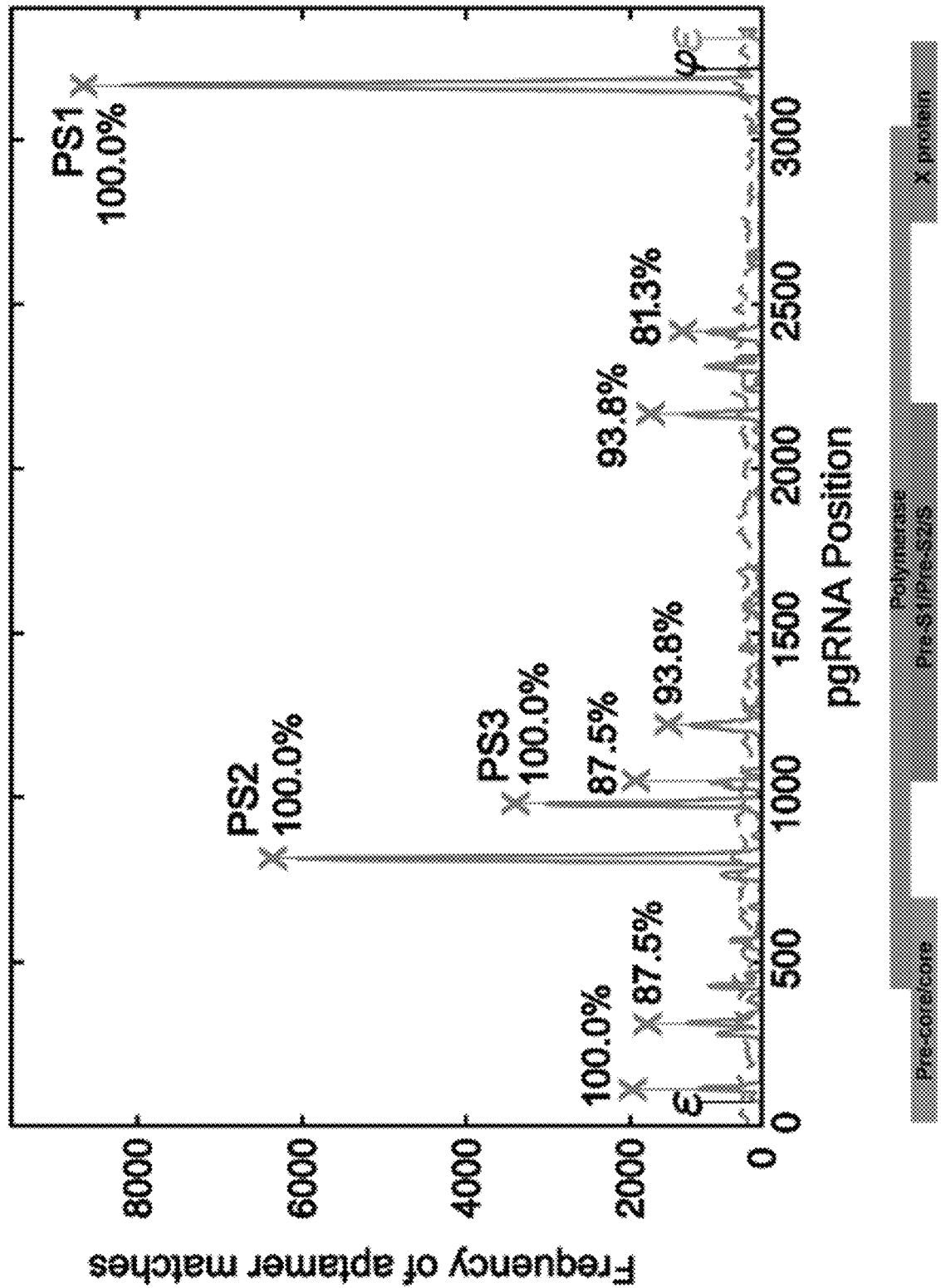
Figure 2B:
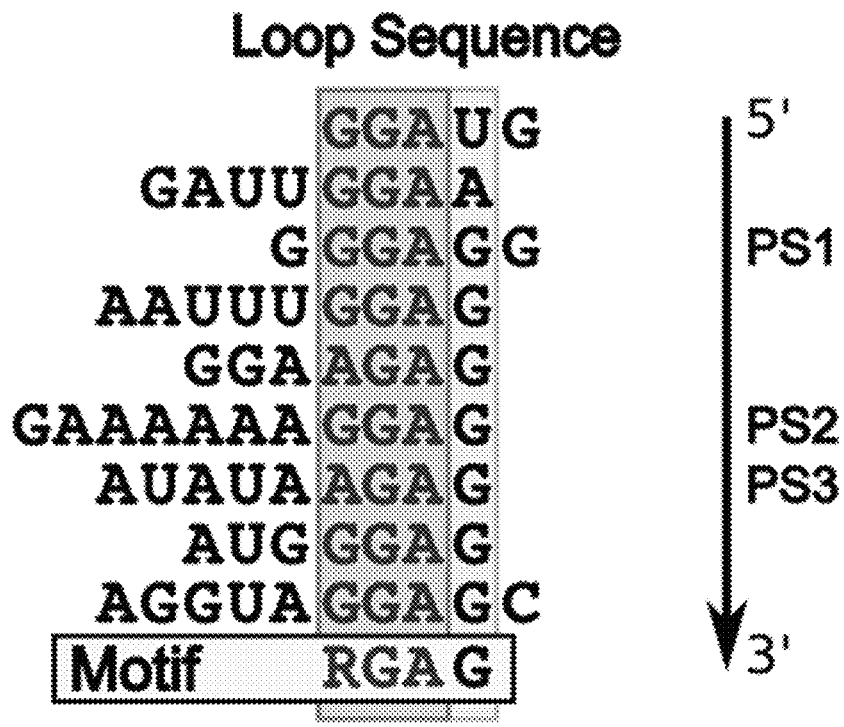
Figure 2C:
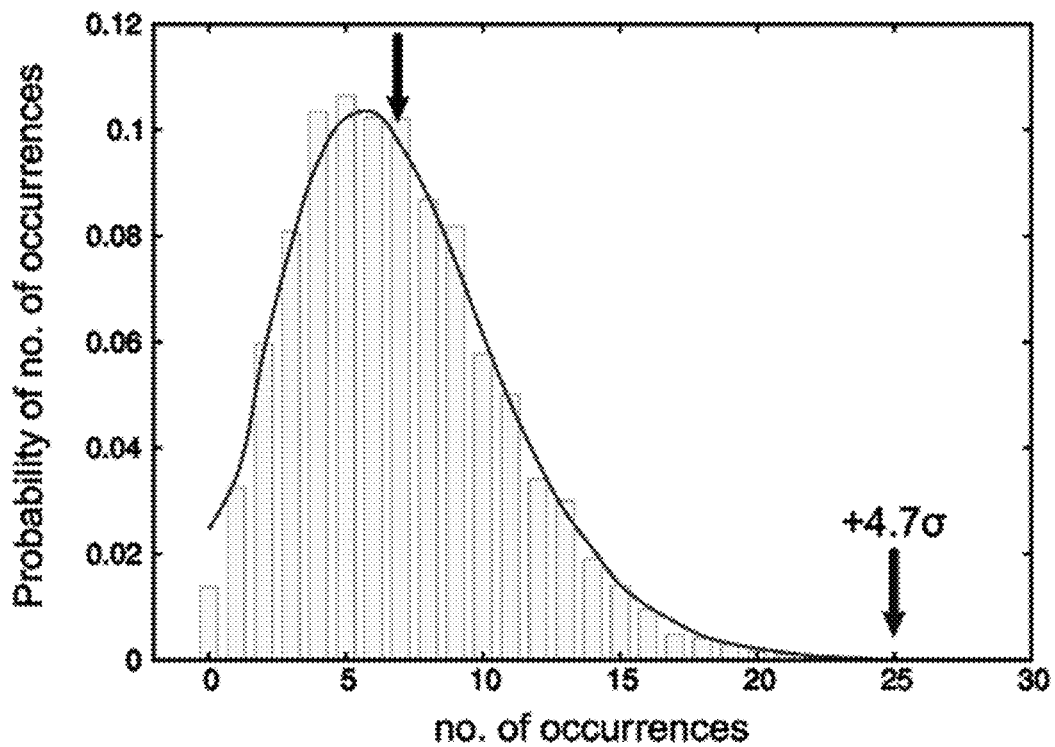

FIG. 1A The genetic map of HBV showing the partially dsDNA genome and the four open reading frames of the virally encoded proteins: Pre-core/core (Cp), which forms the nucleocapsid (NC) shell; Pre S1/PreS2/S, the envelope embedded HBV antigen (HbsAg); X (which plays a role in numerous aspects of the HBV life-cycle within the cell); the polymerase, (P) and the pgRNA with the positions of the 5' ε, the redundant 3' ε (grey circle), φ and the preferred sites (PSs) studied here, highlighted by circles. FIG. 1B The HBV NC (left) comprises either 90 (T=3) or 120 Cp dimers (T=4 shown). Cp dimers form characteristic four-helix bundles, two from each monomer, that appear as spikes on the surface (right bottom). The two conformers of the HBV Cp dimer (A/B & C/D) that are needed to create the T=4 particle are also shown (right top). HBV capsid and protein dimer were obtained from PDB (3J2V)(1) FIG. 1C The Cp of the isolate used here is 185 amino acids long (RD dipeptide insertion underlined), with an alpha-helical rich region (149 amino acids long), and a C-terminal ARD (SEQ ID NO: 53). The 149$^{th}$ amino acid, V, is labelled light grey for clarity. ARD is rich in both basic amino acids and serines (S) are known sites for phosphorylation, which are thought to play roles in NC assembly;

FIGS. 2A-2C Identification of conserved PS motifs in the pgRNA

Figure 3A:
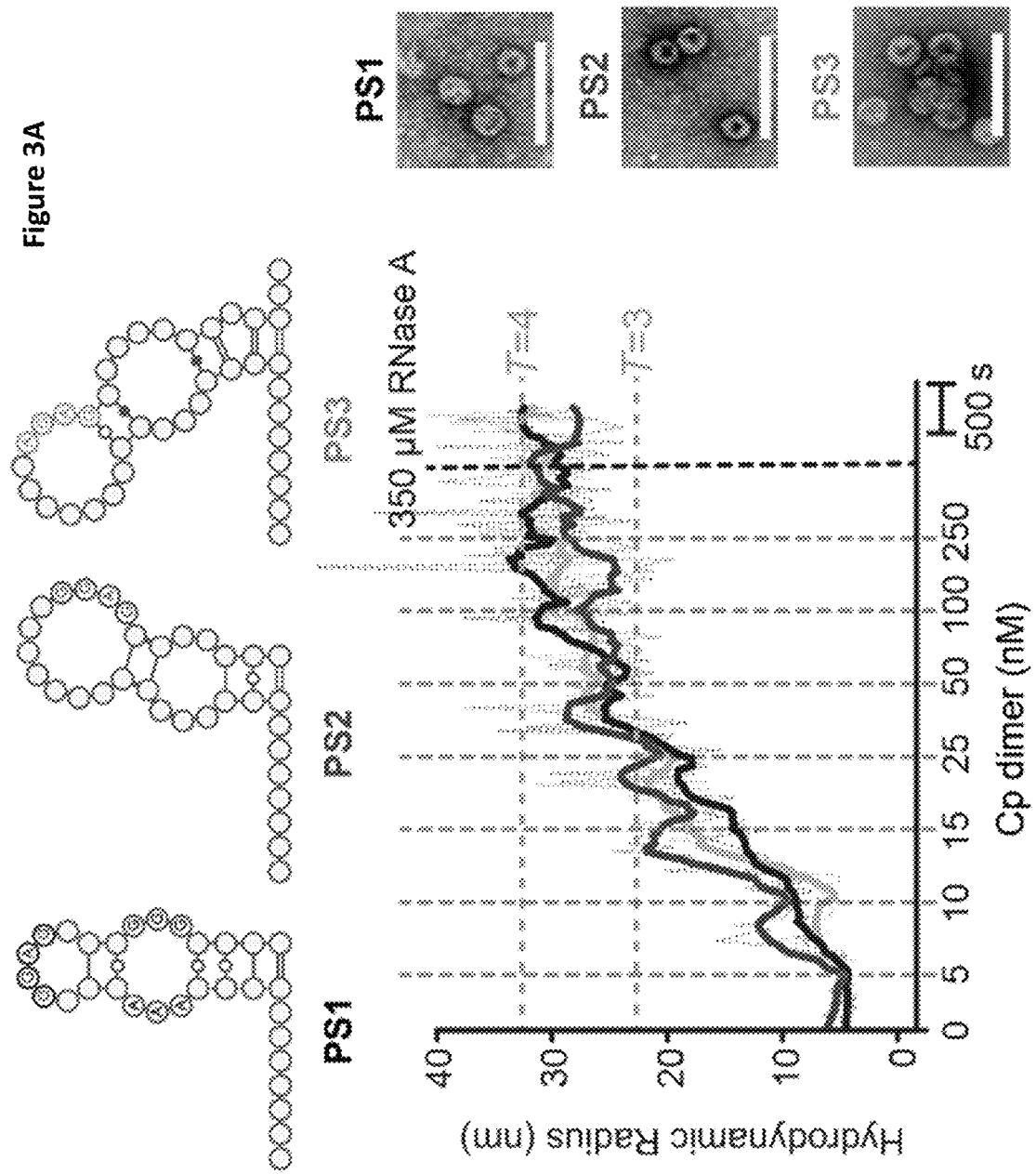

FIG. 2A The frequency of aptamer matches (Bernoulli score 12) from the selected (solid grey line) and naïve (grey dashed line) libraries against the reference strain (NC_003977.1). The peaks that occur in the majority of tested strains are marked with a X together with the percentage of strains with peaks in the same positions. The peaks with highest frequency and level of conservation between strains are labelled PS1, PS2 & PS3. FIG. 2B Alignment of loop sequences of stem-loops in the sequences surrounding the conserved nine Bernoulli peaks from FIG. 2A obtained using Mfold. The sequences all display an RGAG motif in a single-stranded loop. The 6$^{th}$ sequence from the top is SEQ ID NO: 9, and the 9$^{th}$ sequence from the top is SEQ ID NO: 54. FIG. 2C The probability of the number of occurrences of the motif RGAG in the loop portions of stem-loops across 10,000 randomised versions of five of the tested strains (see strains marked by an asterix in the Methods). The grey bars show this probability in the reference strain, whilst the black line is the equivalent across all five strains. The black arrow indicates the average number of occurrences in loops of RGAG in the randomised versions of the reference strain (=6.85). The arrow labelled +4.7σ indicates the number of occurrences in the reference strain (=25), which is 4.68 standard deviations from the average, and the other tested strains have similar levels of occurrence;

FIGS. 3A-3B PSs trigger sequence-specific VLP assembly

Figure 11:
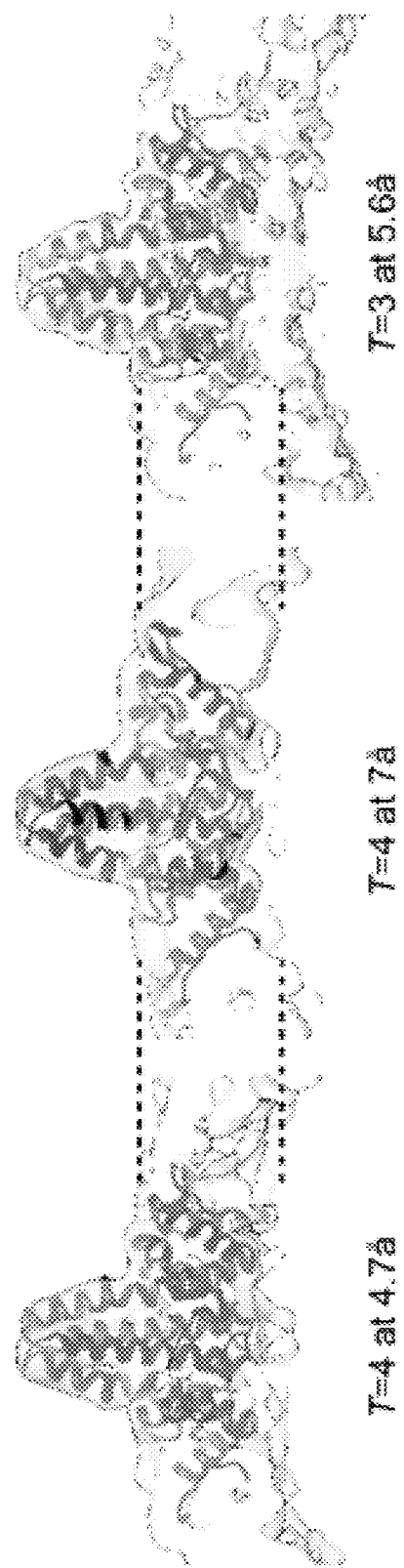

FIG. 3A Dye end-labelled RNA oligos encompassing PS1 (black), PS2 (dark grey) or PS3 (light grey) were each assessed for their ability to bind Cp and form VLPs at nanomolar concentrations using smFCS. All reactions contained 15 nM of RNA dye-labelled as described in Methods. Vertical dotted lines indicate points where Cp was added with the final concentrations shown in nM. Samples were allowed to equilibrate between additions. The faint trace represents real time, raw signal while the thick line represents smoothed data. EM images were recorded of the samples prior to RNase A addition (right). Scale bars represent 100 nm. FIG. 3B Hydrodynamic radial distributions of the reactions in FIG. 3A, taken following the last addition of Cp (here and throughout). The amount of Cp assembling beyond dimer in the absence and presence of RNA (unlabelled) was compared. At the end of these reactions, Cp was labelled with Alexa Fluor®-488 fluorophore (Methods) and the resulting $R_h$ distributions quantitated for the Cp only and Cp plus unlabelled PS1 scenarios. Note dye-labelling of the Cp dimer prevents it from assembling so this has to be an end-point measurement. A sample of each was taken for analysis by TEM. smFCS and TEM were repeated in triplicate;

FIGS. 4A-4D The structures of T=3 and T=4 HBV VLPs suggest a mechanism for the specification of their quasi-conformations The icosahedrally-averaged cryo-EM structures of FIG. 4A T=3 and FIG. 4B T=4 HBV VLPs at 5.6 Å and 4.7 Å resolution, respectively. A red icosahedron is included to assist interpretation of the two reconstructions, which are shown in the same orientation. FIGS. 4C and 4D show ~30 Å thick slabs through the structure of each particle, with a fitted Cp-dimer in each. The T=3 shell is thicker, indicating that density corresponding to the ARDs is resolved in the T=3, but not the T=4, structure. Rendering both structures at equivalent resolution does not change this interpretation (FIG. 11);

FIGS. 5A-5H Asymmetric RNA feature in T=4 HBV VLPs

Figure 6:
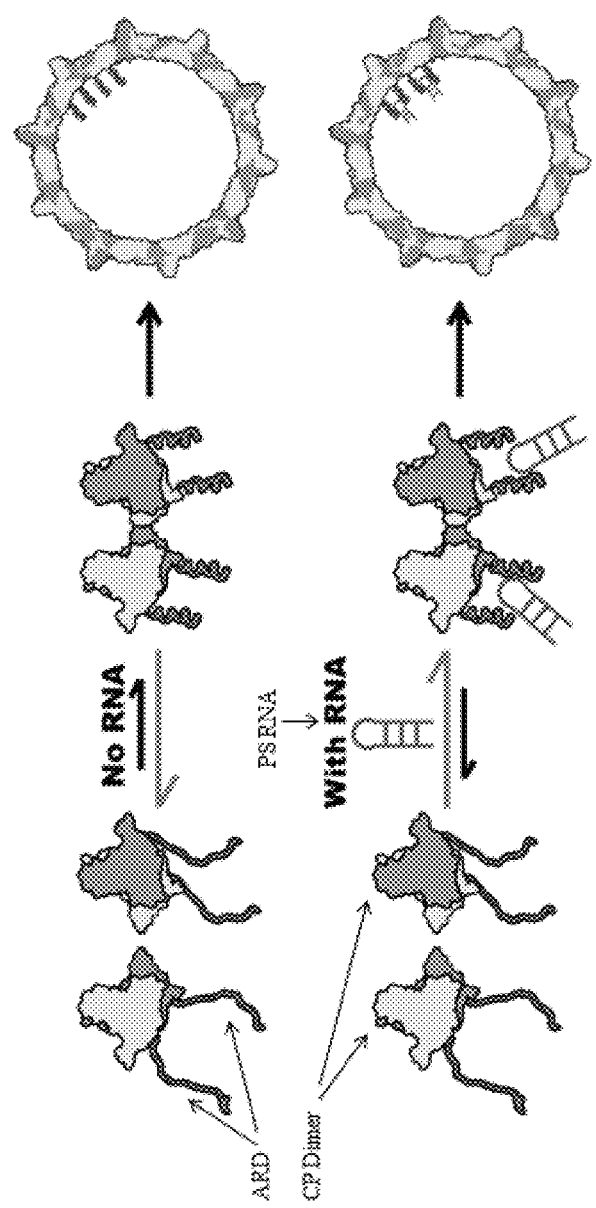

FIGS. 5A and 5B 2D views of 42,411 T=4 particles were calculated by maximum-likelihood-based classification in RELION. An asymmetric RNA feature is visible in a subset of these particles FIG. 5B. FIG. 5C An asymmetric 3D reconstruction at 11.5 Å resolution of 10,851 particles containing the asymmetric feature. The asymmetric density for the protein shell is icosahedral, despite the lack of any symmetry averaging. FIG. 5D An approximately 40 Å thick slab through the asymmetric HBV VLP reconstruction shows the asymmetric feature bound to one region of the Cp shell revealing density ascribed to RNA and ARDs within the protein shell (bright cerise, magenta and purple). The figures were rendered in a radial colour scheme (Blue=165 Å; Cyan=152 Å; Green=139 Å; Yellow=126 Å; Pink=113 Å) using USCF Chimera. FIG. 5E The asymmetric RNA density is centred beneath a Cp dimer surrounding one of the 5-fold vertices of the T=4 particle (indicated by the circle). A single Cp dimer is fitted as a ribbon diagram into the appropriate position using the 'Fit in map' function in UCSF Chimera. FIG. 5F As the front of the map is slabbed away, the density within is revealed. Shown and manually fitted is a single copy of PS1 as a ribbon diagram (modelled in RNA Composer). FIG. 5G Side-view of the same portion of the map, with the view oriented by the projected blue circle. Discrete fingers of density are visible between the Cp layer and RNA density, which is large enough to accommodate 2-4 RNA oligonucleotides. FIG. 5H Histogram of photobleaching steps from 630 individual fluorescent spots on a grid containing PS1 HBV VLPs. Spots containing >10 steps resulted from traces exhibiting exponential decay, which were assumed to be aggregates in which multiple bleaching steps occur simultaneously. Photobleaching was performed in duplicate;

FIG. 6 Proposed model of HBV NC assembly

Figure 7A:
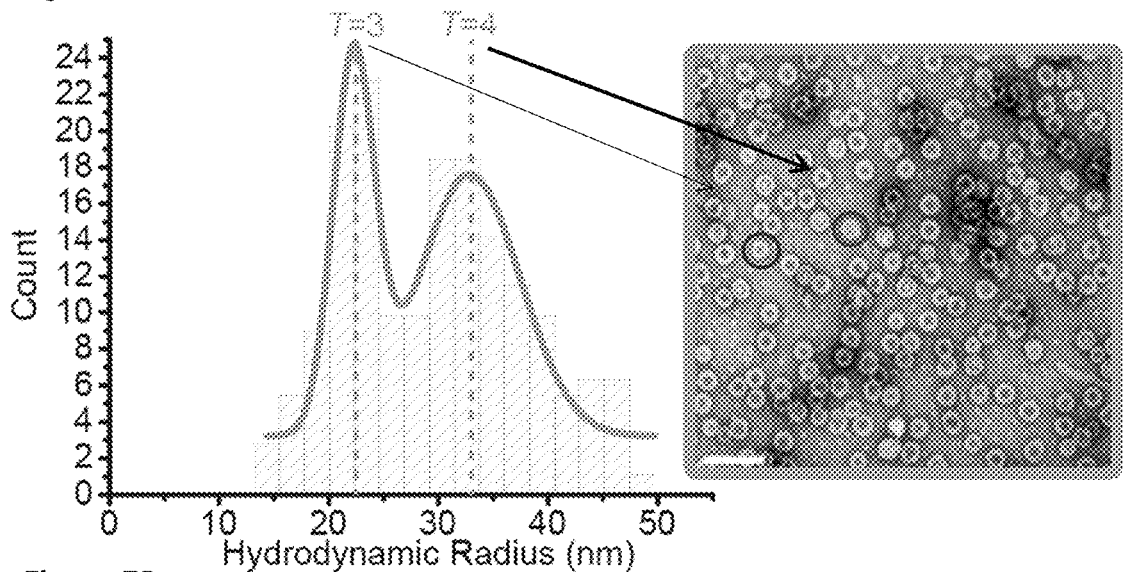
Figure 7B:
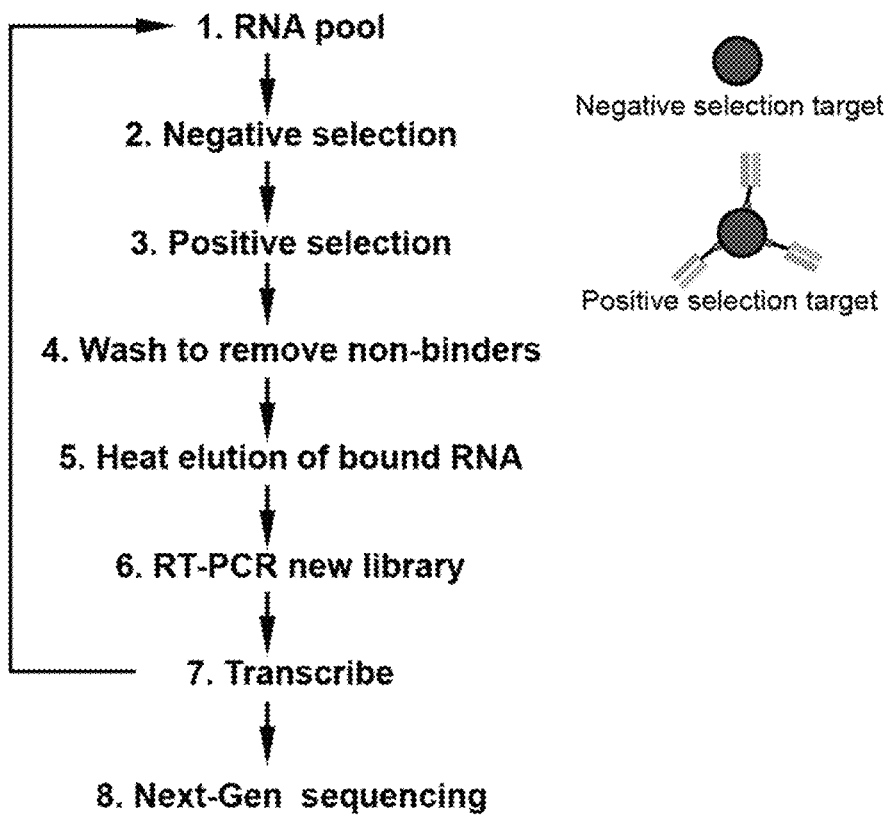

ARD within a Cp dimer inhibit formation of a dimer of dimers, the first intermediate on the pathway to NC assembly. Reducing the net charge on the ARD by phosphorylation or PS RNA binding allows this structure to form more easily, triggering NC formation. At concentrations higher than those mimicking in vivo conditions as used here, the unmodified dimer of dimers forms and particles self-assemble without RNA or will bind RNA non-specifically to produce the same outcome;

FIGS. 7A-7B Characterising HBV VLPs from *E. coli* and SELEX protocol

Figure 8A:
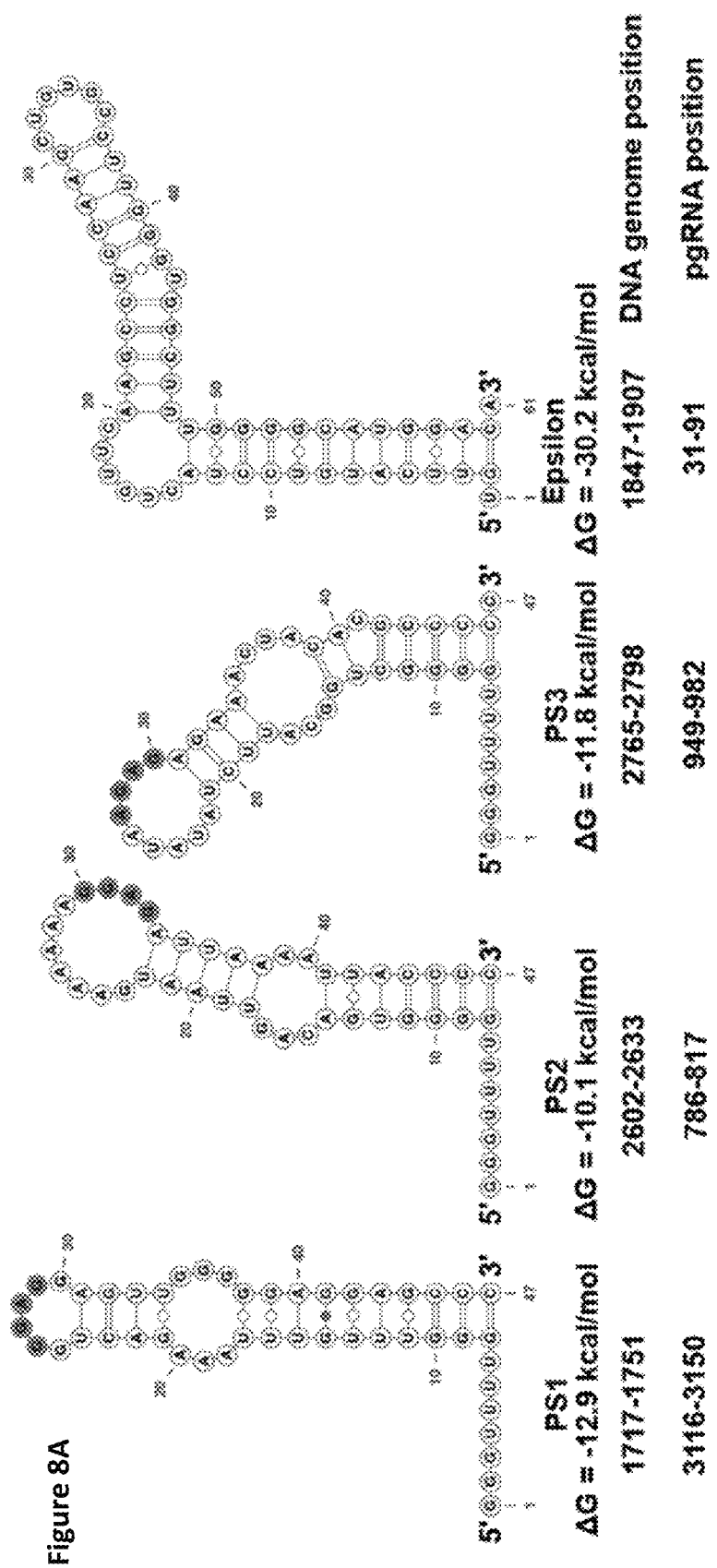
Figure 8B:
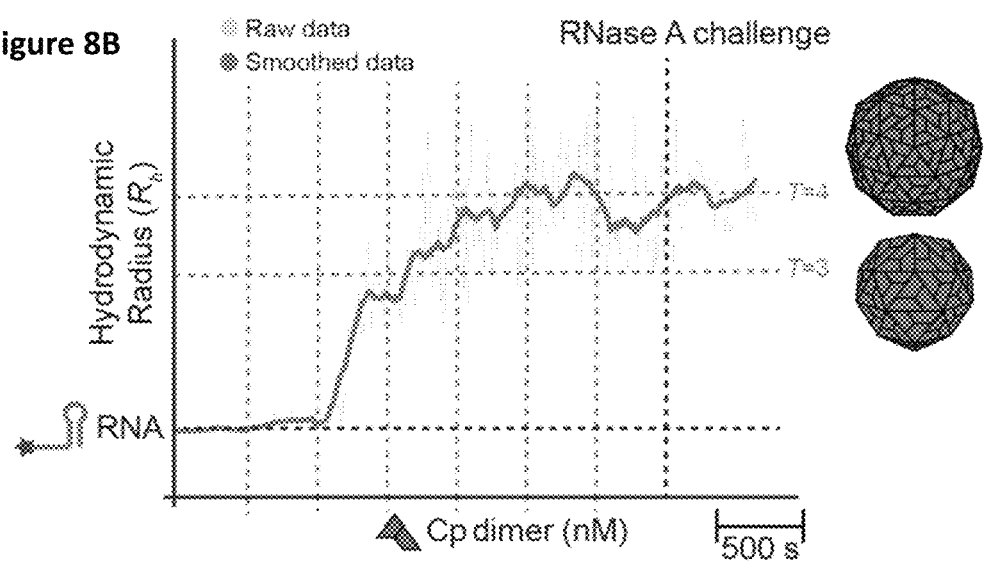
Figure 8C:
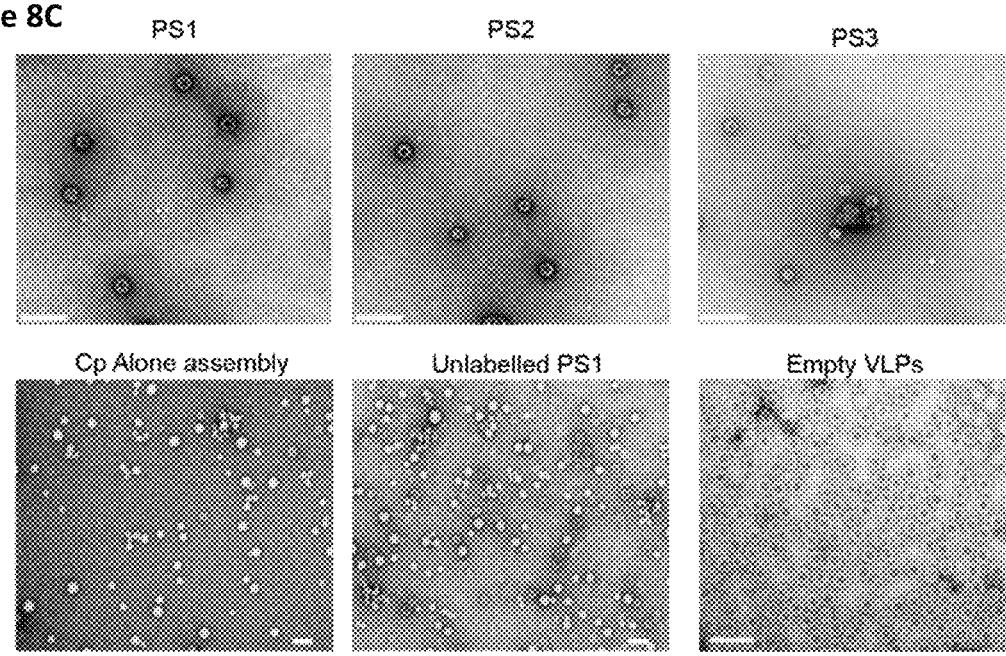

FIG. 7A Hydrodynamic radial distribution and negative stain EM image of Alexa Fluor®-488 fluorophore labelled HBV VLPs purified from *E. coli*. Integration of peak yields suggests a roughly 2:1 ratio of T=4 (circle, 63%) and T=3 (circle, 37%) VLPs. Scale bar represents 100 nm. FIG. 7B SELEX protocol showing selection for aptamers with high affinity to HBV 185 Cp. HBV VLPs were immobilised onto carboxylic magnetic beads (circles) and dissociated into Cp dimers (grey rectangles) using guanidinium chloride. An RNA pool encompassing a random region (40N) was enriched for sequences with affinity for Cp by repeated cycles of binding to these beads, partitioning and amplification. Negative selections at each round used carboxylic acid beads which had been treated with NHS-EDC and inactivated with Tris. Stringency was increased after round 5 by decreasing the number of positive beads by half and increasing the number of washes from 8 to 10. The reverse transcriptase-PCR products at the end of each round were analyzed by native PAGE to confirm the isolation of products for the next round of selection. The $10^{th}$ round products were converted to DNA and sequenced;

FIGS. 8A-8C PS oligo structures, example smFCS trace and EMs of PS containing VLPs FIG. 8A PS1-3 and ε secondary structures, made using VARNA software(2), were predicted in Mfold. Preferred sites were taken from the HBV genome, NC_003977.1, at positions: $PS1_{(1717-1751)}$, $PS2_{(2602-2633)}$ and $PS3_{(2765-2798)}$. In order to make them all the same length (47 nucleotides) to avoid effects of charge differences the following additions were made; PS1, 5'-GGGUUUUGG and CCC-3'; PS2, 5'-GGGUUUUGGGG (nt 1 to 11 of SEQ ID NO: 57) and CCCC-3'; PS3, 5'-GGGUUUUGG and CCCC-3'. The consensus motif RGAG is highlighted in red in each of the loops. The stability of each RNA fold, as predicted by Mfold, is shown below each structure.

FIG. 8B Example smFCS assay. $R_h$ values for, fluorescently labelled RNAs are determined before and after Cp is titrated in at fixed time points (vertical dashed lines), allowing the $R_h$ values to equilibrate after each step. The faint red trace represents real time, raw signal while the thick red line represents smoothed data. PS1 $R_h$ initially climbs slowly, until a threshold Cp concentration, which triggers rapid assembly into a T=3 or T=4 VLP ($R_h$ ~24-32 nm, orange dashed lines) as determined by measurements of Alexa-Flour 488 labelled HBV particles from *E. coli* (FIG. 7A). At the end of each titration, the complexes formed are challenged by addition of RNase A. An unchanged $R_h$ is assumed to mean that the test RNA has been encapsidated in a closed VLP. The time scale on which this occurs is indicated in the bottom right.

FIG. 8C TEMs from assembly reactions of PS1, 2, 3 and Cp alone and unlabelled PS1 in FIG. 3A. Large white particles in Cp alone and Unlabelled PS1 TEMs are latex beads. Also present is TEM from empty particle assembly described in Table 2. These empty HBV particles were assembled at much higher concentrations of Cp (1.5 µM) and in the absence of RNA. Scale bars represent 100 nm.

FIGS. 9A-9D smFCS assays of PS1 variants

Figure 9A:
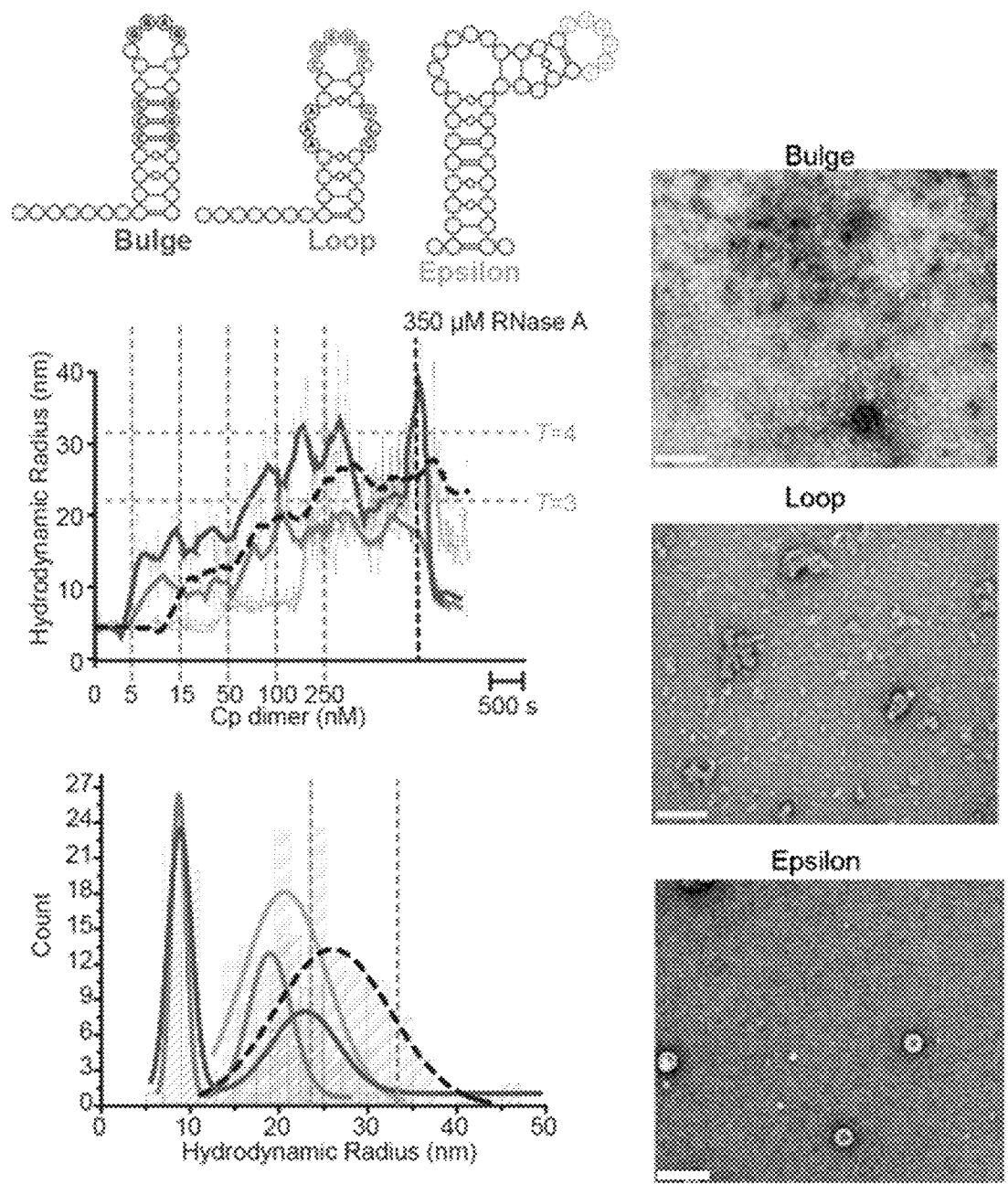
Figure 9B:
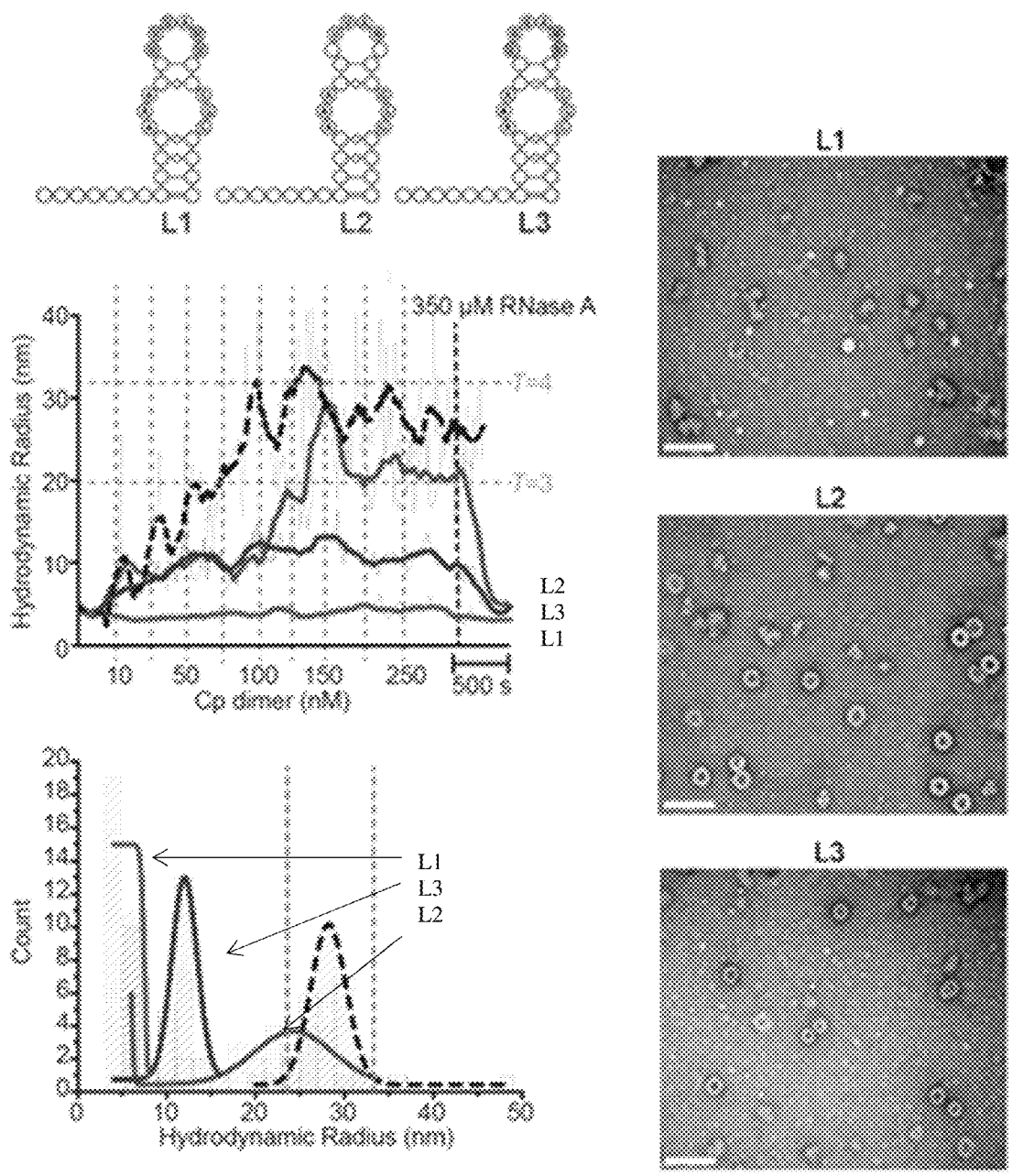
Figure 9C:
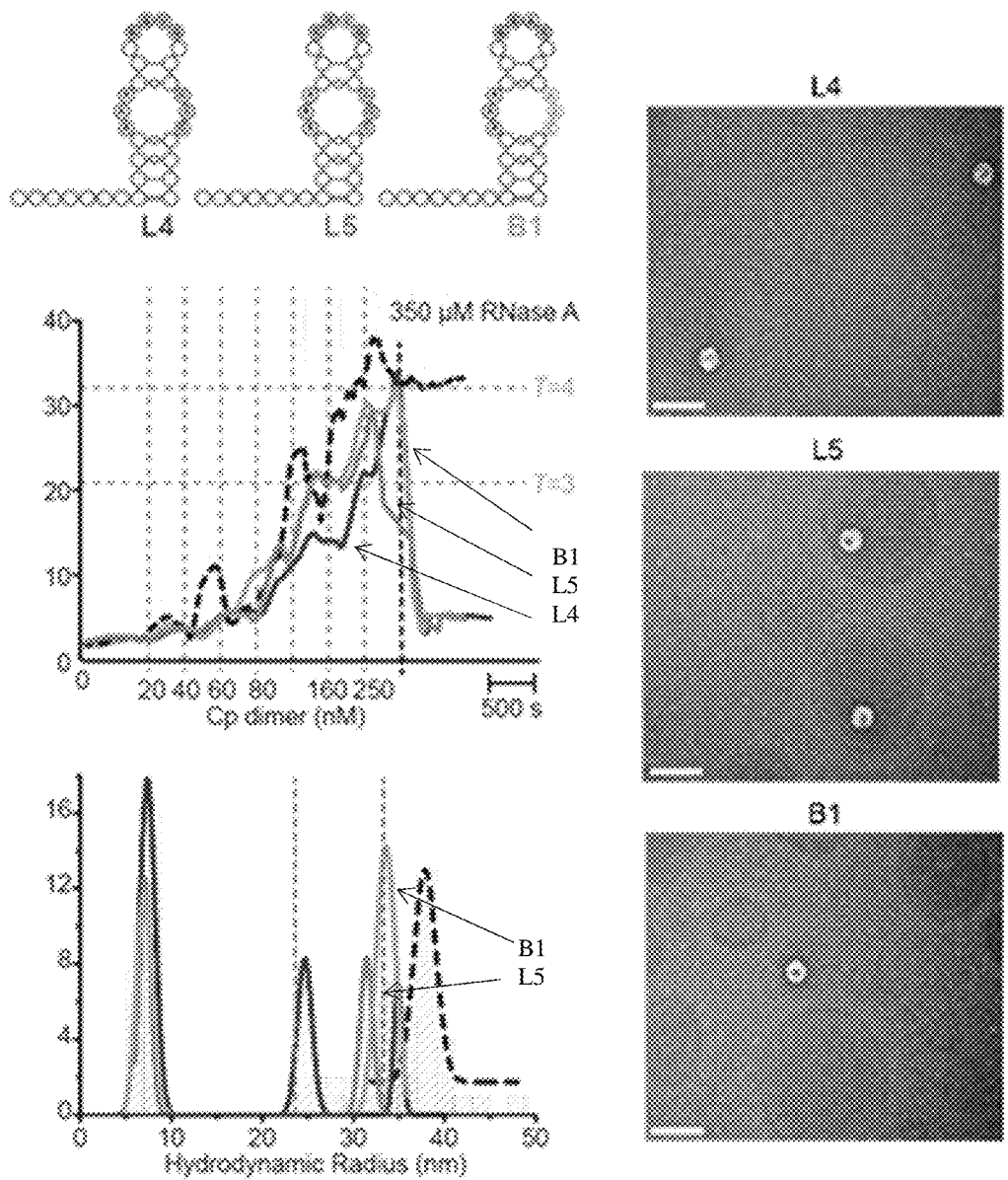
Figure 9D:
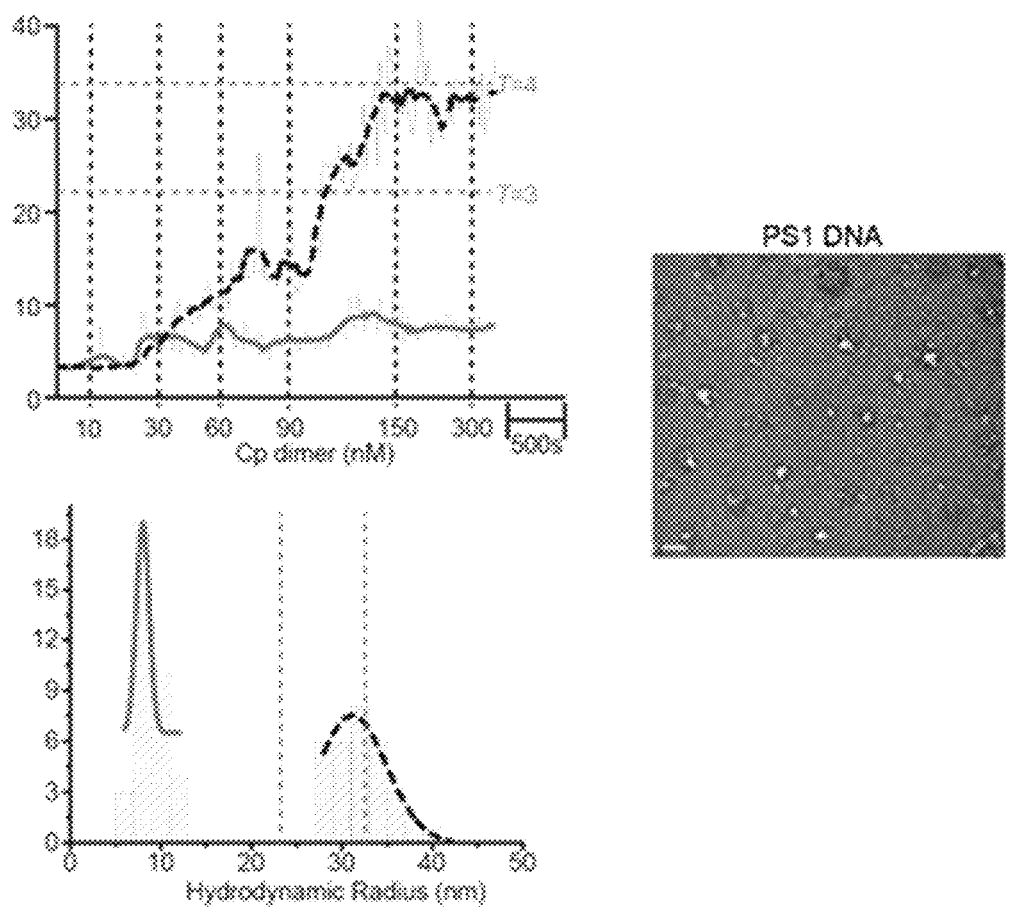

FIG. 9A smFCS assays of the PS1 variants (structures top left) and accompanying hydrodynamic radial distributions plotted in 2 nm bins and fitted with Gaussian peaks below, as colour coded in the key. 15 nM PS1 (black), PS1 loop mutant (grey) bulge mutant (dark grey) and epsilon (light grey) RNAs were tested for their ability to form VLPs under single molecule conditions. Vertical dotted lines indicate points of addition of Cp with the final concentrations shown in nM. Samples were allowed to equilibrate between additions. RNase A was added to check for correctly formed particles. Samples were taken prior to RNase A addition for analysis by TEM shown right, both here and throughout this figure. FIG. 9B—as FIG. 9A with RNA oligos PS1 (dashed black), L1, L2 and L3. FIG. 9C—as FIG. 9A with RNA oligos PS1 (dashed black), L4 (dark grey), L5 and B1 FIG. 9D as (a) with RNA oligos PS1 (dashed black) and DNA oligo PS1 (grey). Scale bars represent 100 nm. PS1 controls (dashed black) in each panel were repeated for individual batches of purified Cp, accounting for the variations in assembly efficiency seen. smFCS and TEM were repeated in triplicate.

Figure 10A:
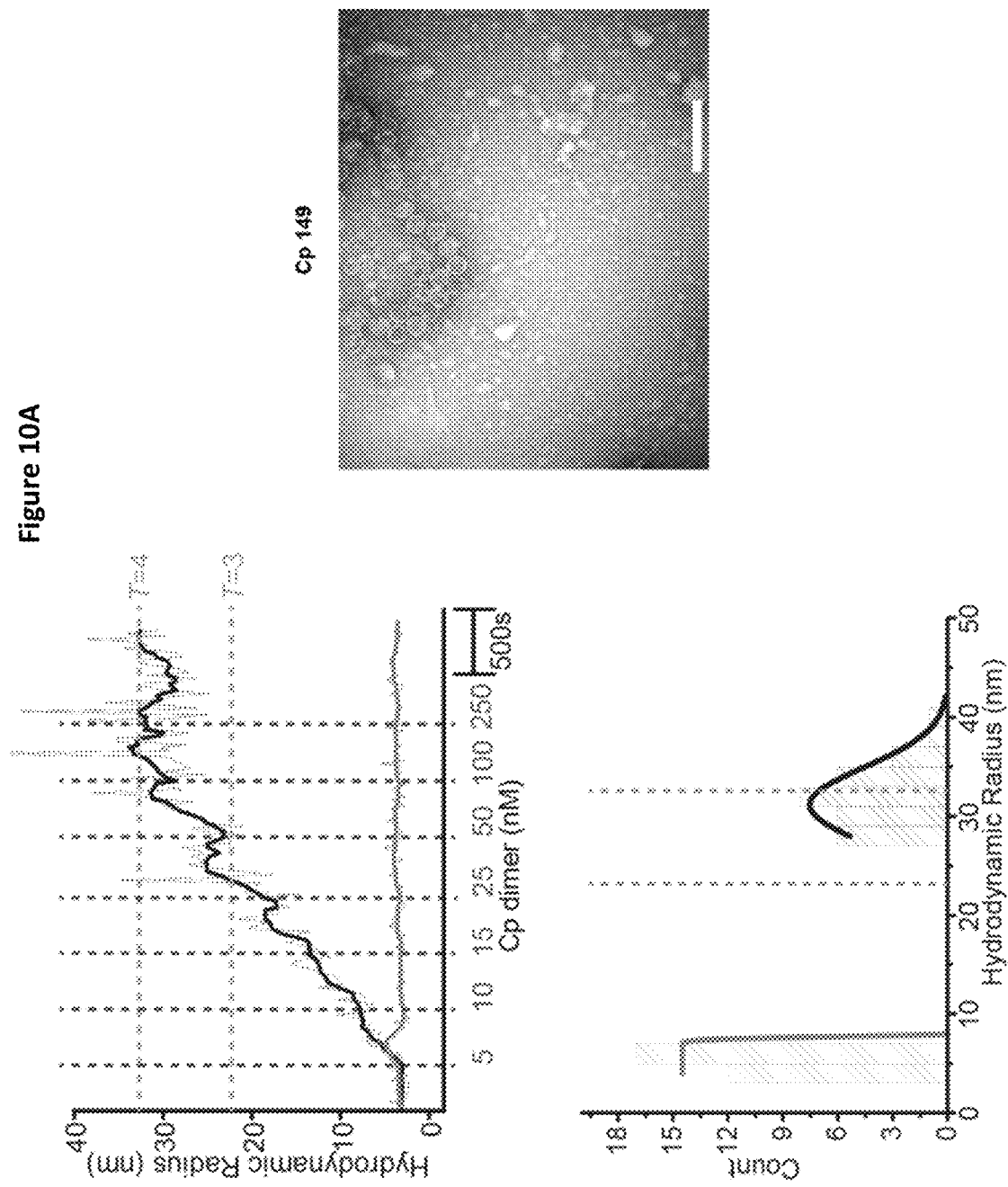
Figure 10B:
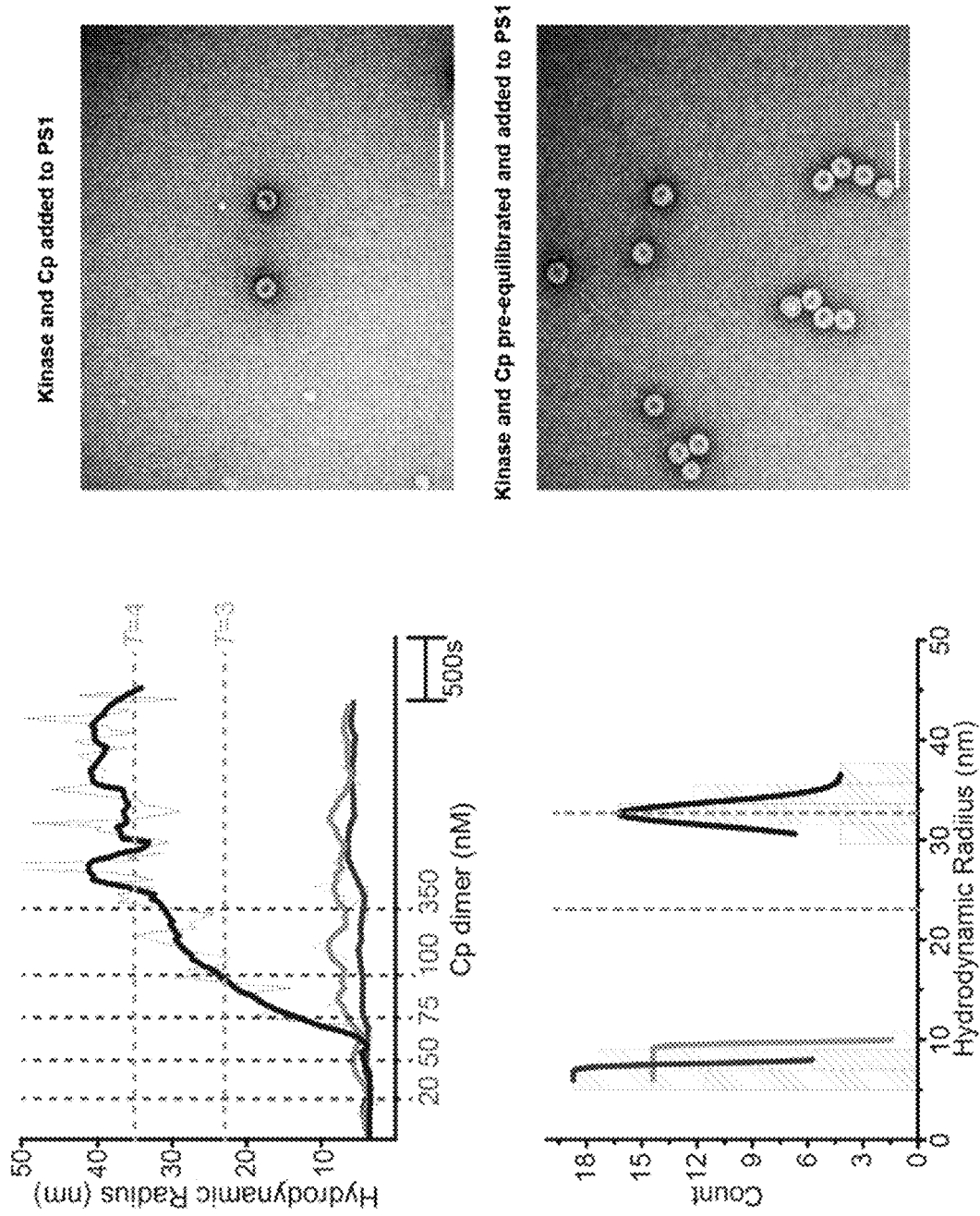

FIGS. 10A-10B Role(s) of ARD and its charge on assembly

FIG. 10 smFCS assays of 15 nM PS1 with Cp (light grey) and $Cp_{149}$ (grey) and accompanying hydrodynamic radial distributions plotted in 2 nm bins and fitted with Gaussian peaks below. EM images of particles are shown (right). FIG. 10B as FIG. 10A with PS1 and Cp (black), kinase and Cp pre equilibrated and added to PS1 (I grey) and PS1 and Cp with kinase added simultaneously (dark grey). TEMs are shown right. Scale bars represent 100 nm. PS1 controls (black) in each panel were repeated for individual batches of purified Cp, accounting for the variations in assembly efficiency seen. smFCS and TEM were repeated in triplicate.

FIG. 11 ARD structure in T=4 and T=3 VLPs.

Slabs (~30 Å thick) through the structures of the icosahedrally-averaged T=4 particle at 4.7 Å (left), the same T=4 structure low pass filtered to 7 Å (middle), and the T=3 particle at 5.6 Å (right). A Cp dimer is fitted into each. Even at a slightly lower resolution than the T=3 VLP, there is no equivalent density for the ARD in the T=4 VLP, confirming that it has different conformations in each particle.

Figure 12A:
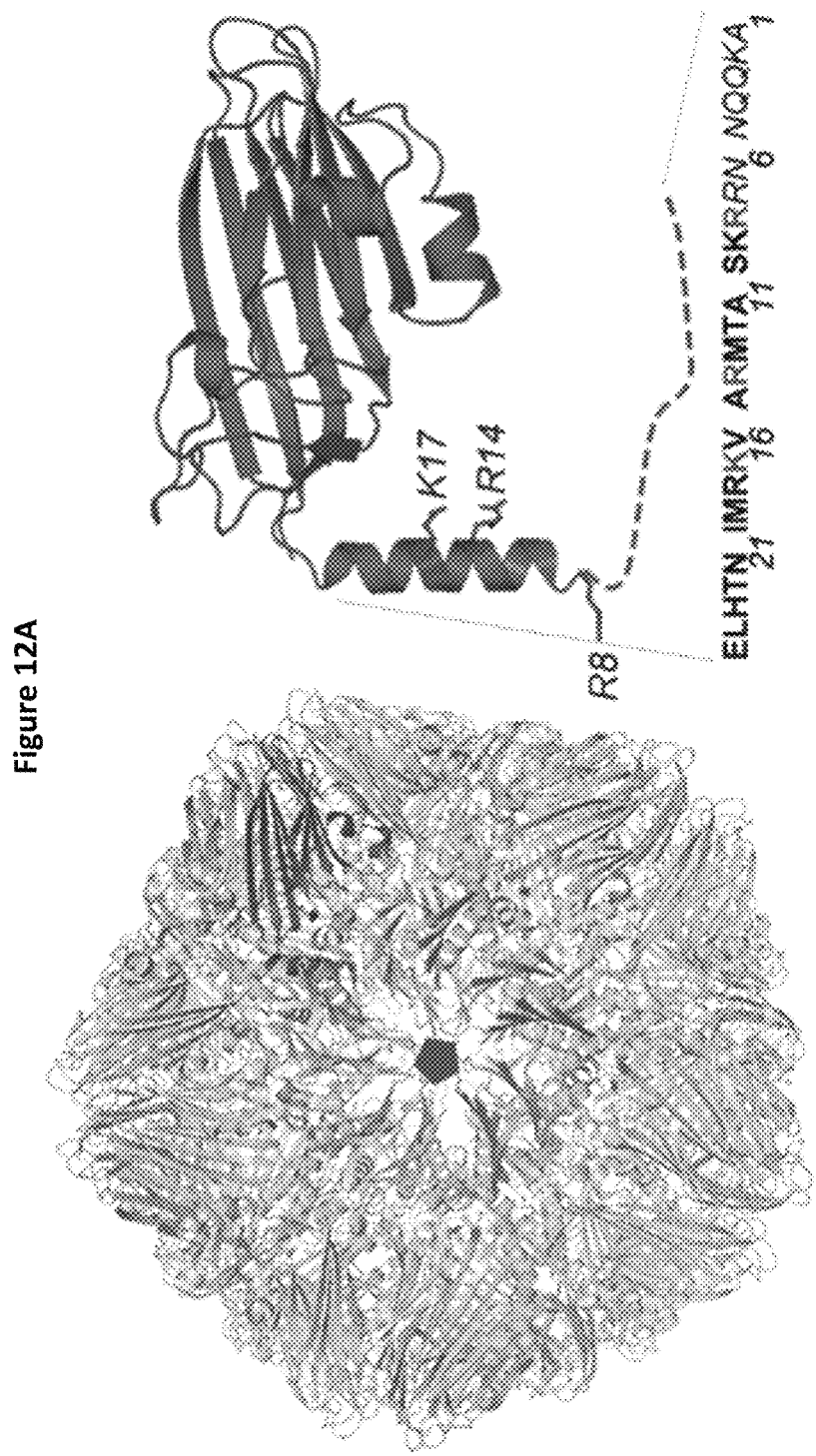
Figure 12B:
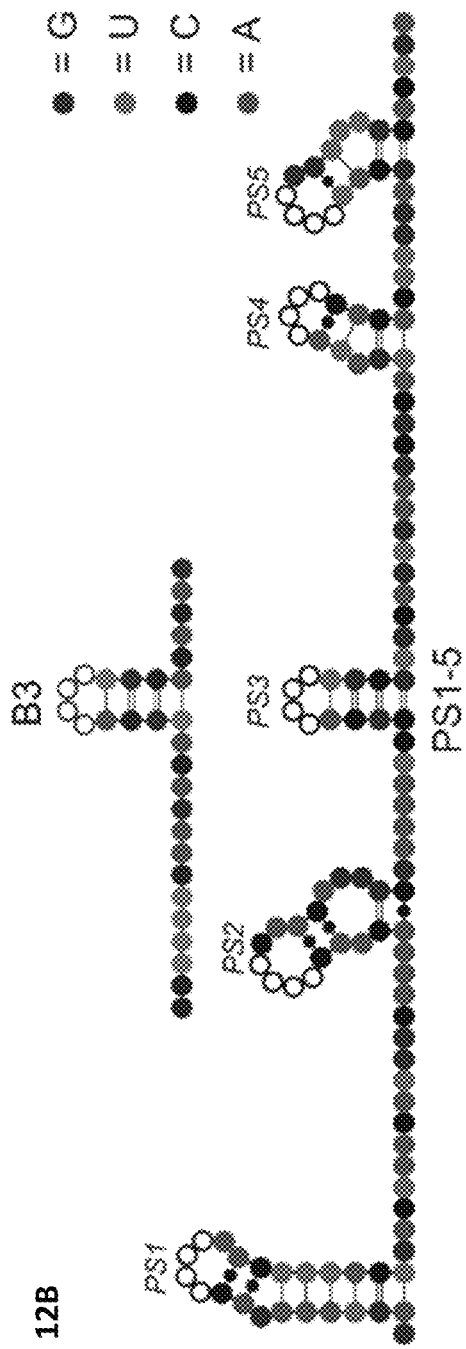
Figure 12C:
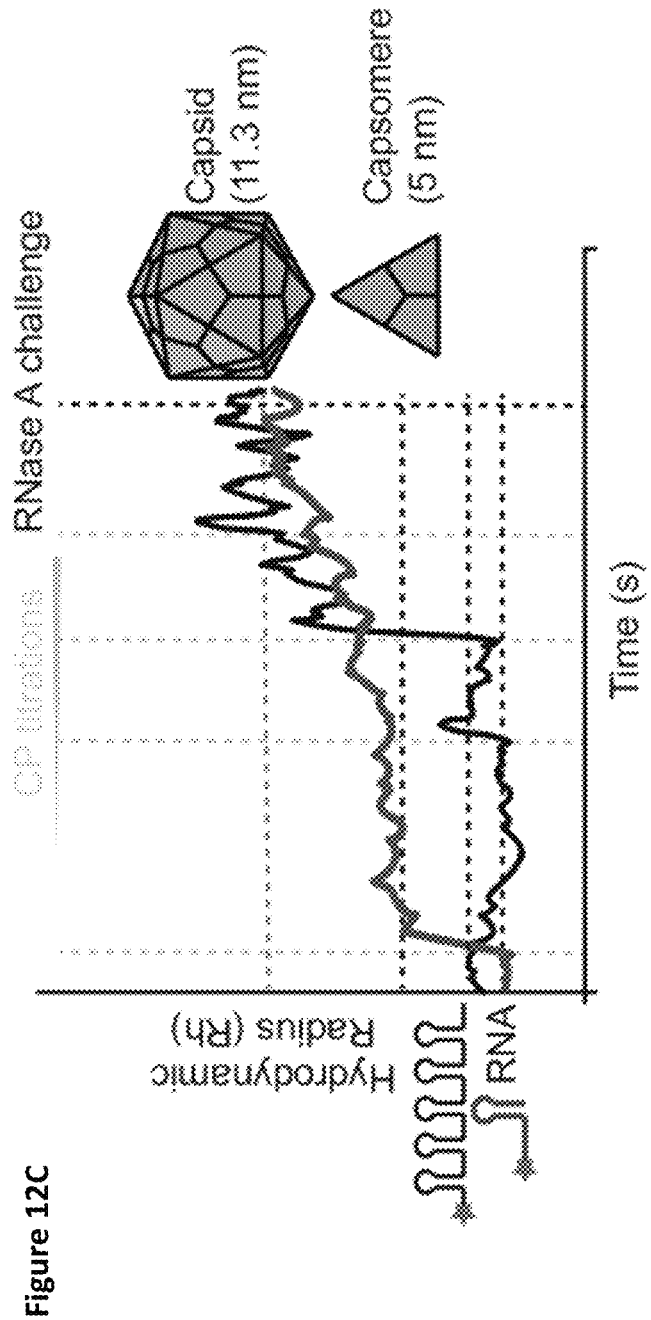
Figures 13A, 13C:
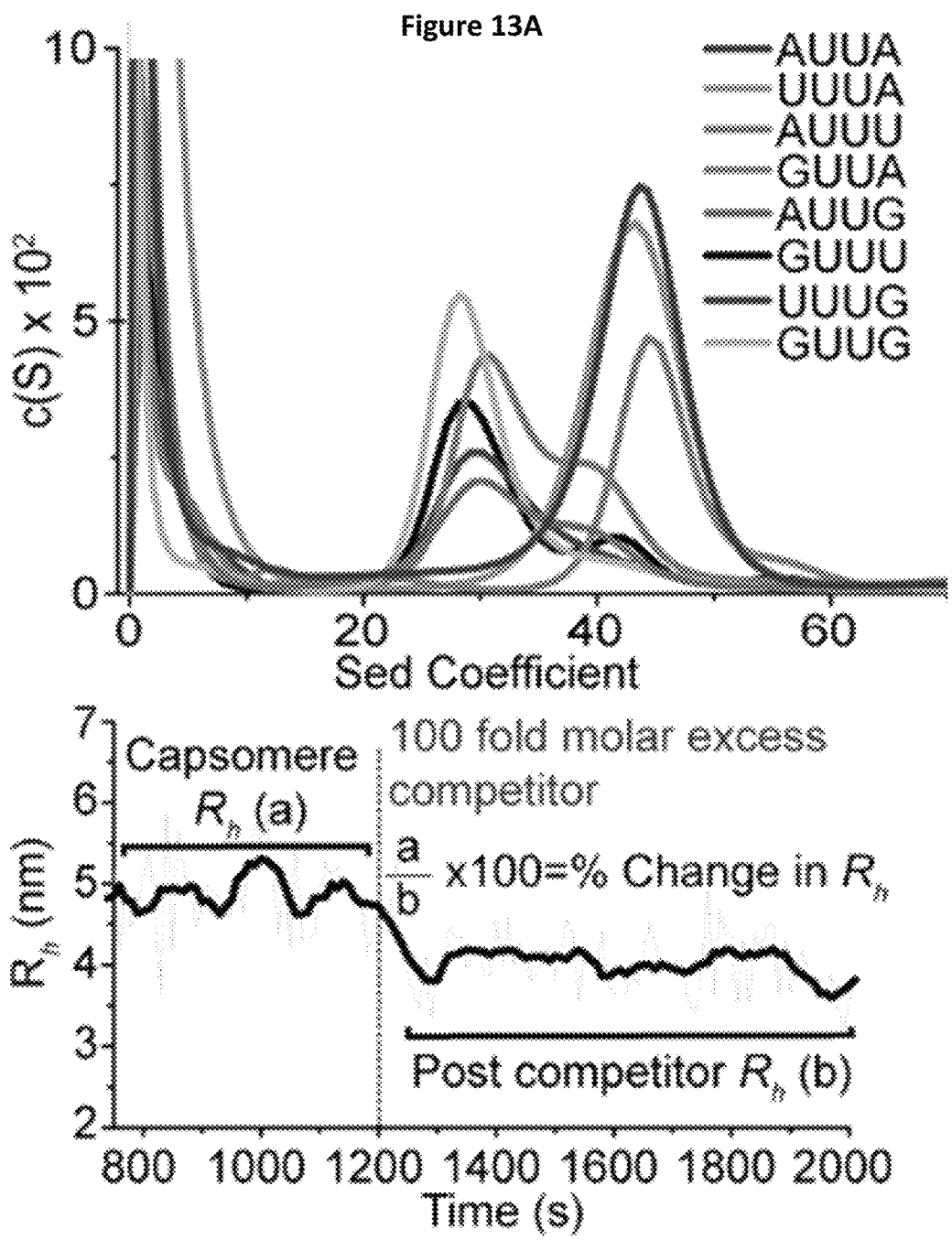
Figure 13B:
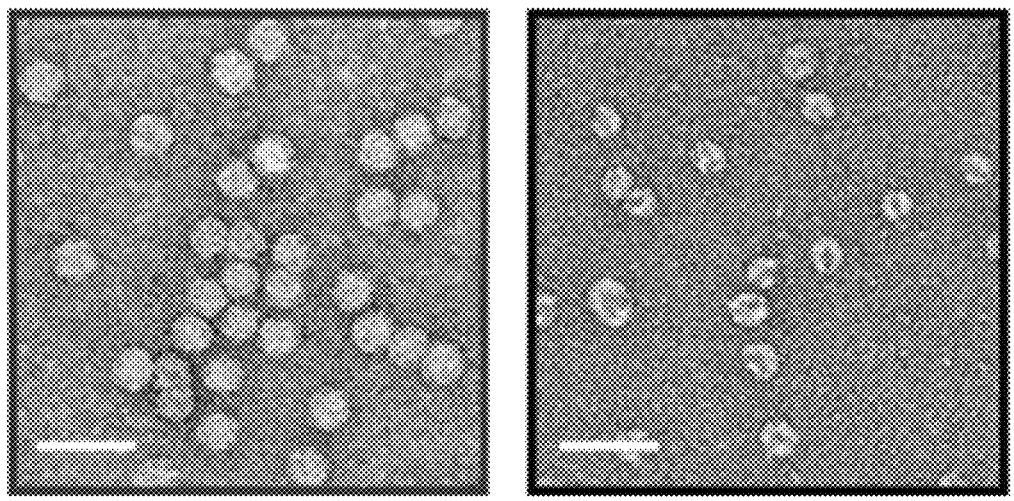
Figure 13D:
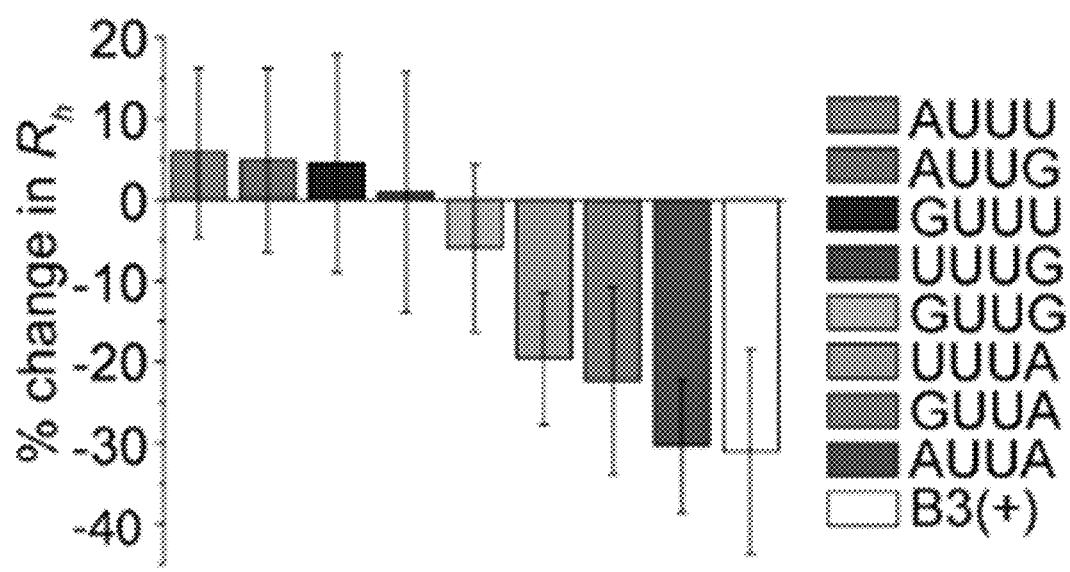
Figure 15A:
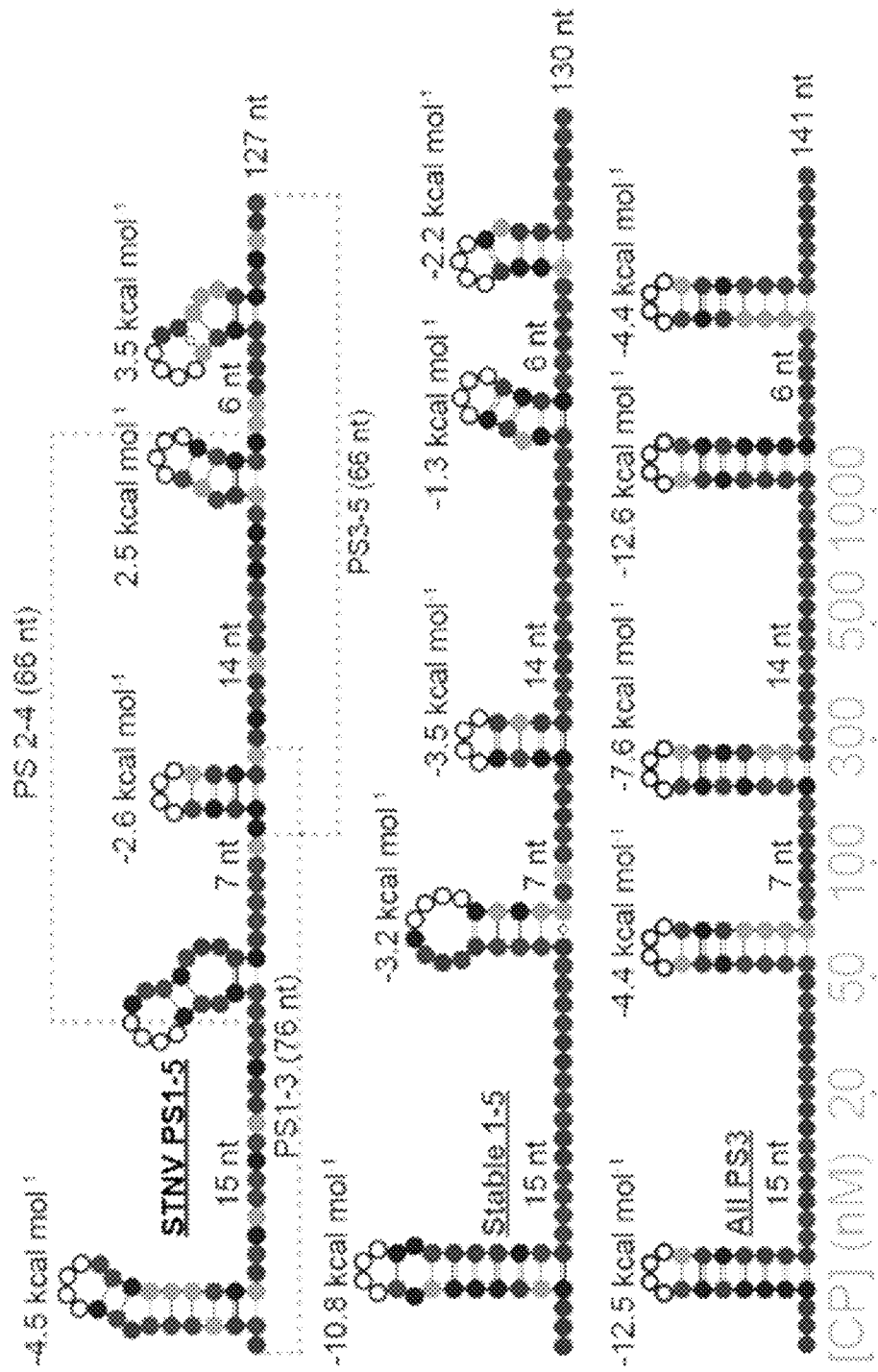
Figure 15B:
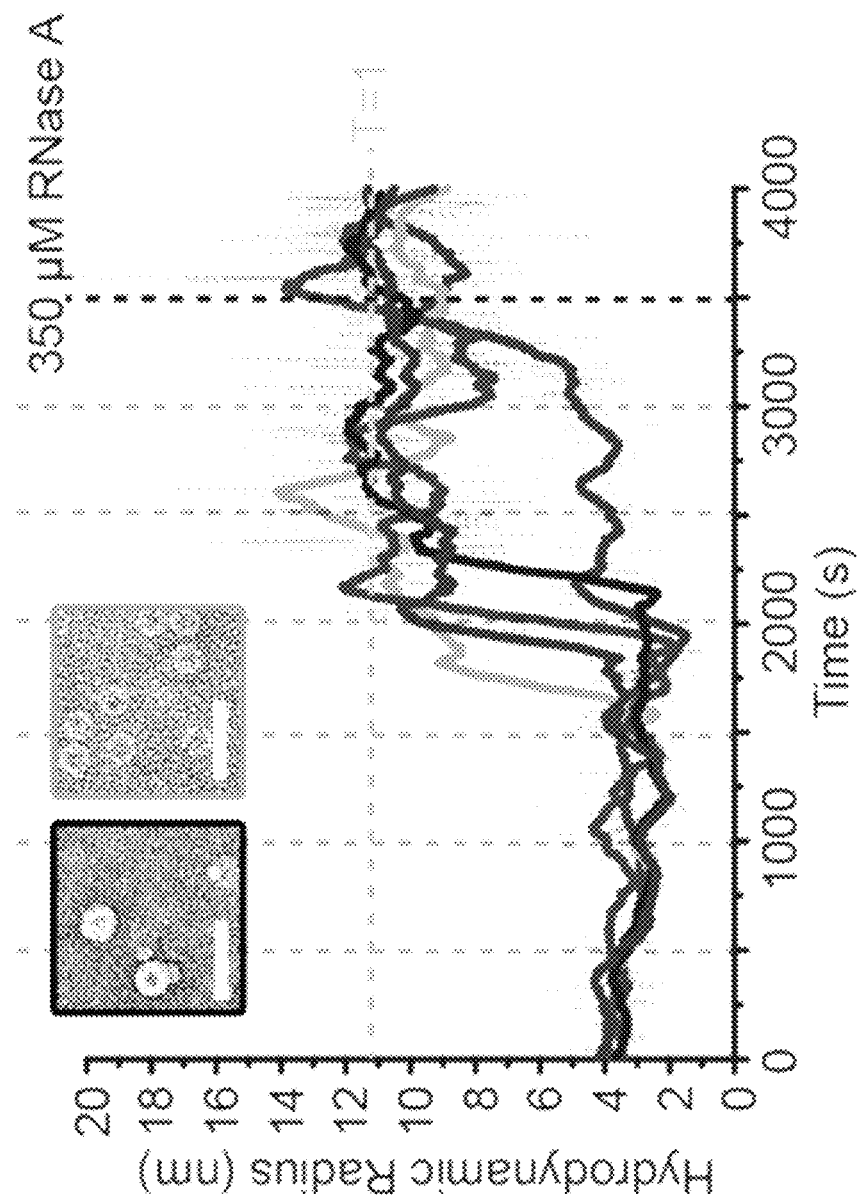
Figures 16A, 16B:
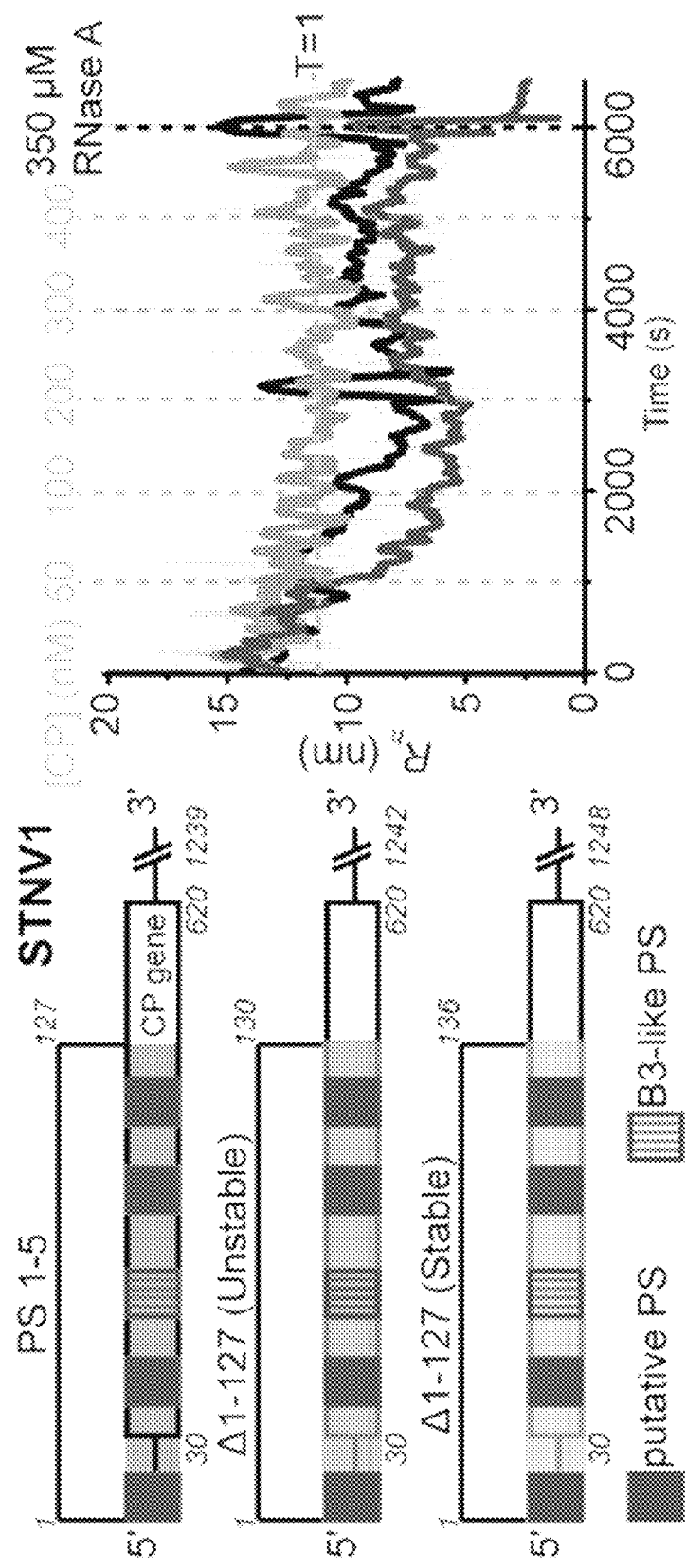
Figure 16D:
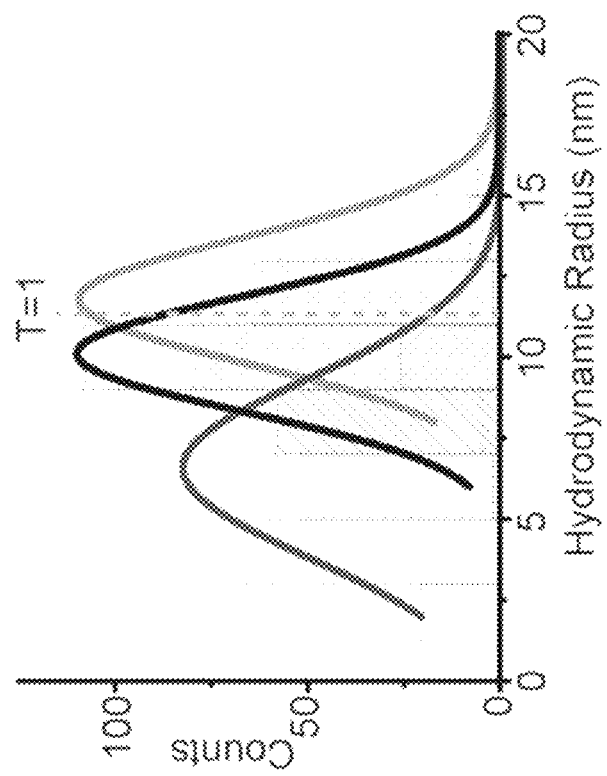
Figure 16C:
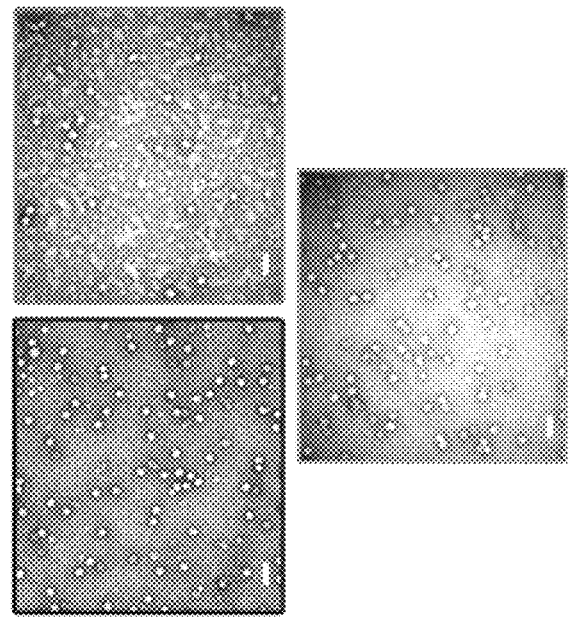
Figure 17A:
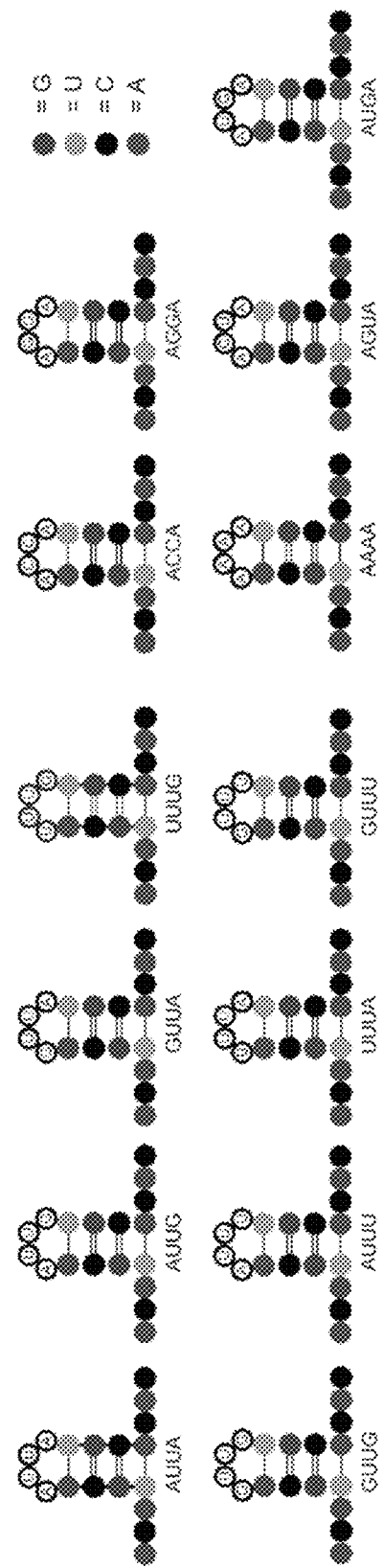
Figure 17B:
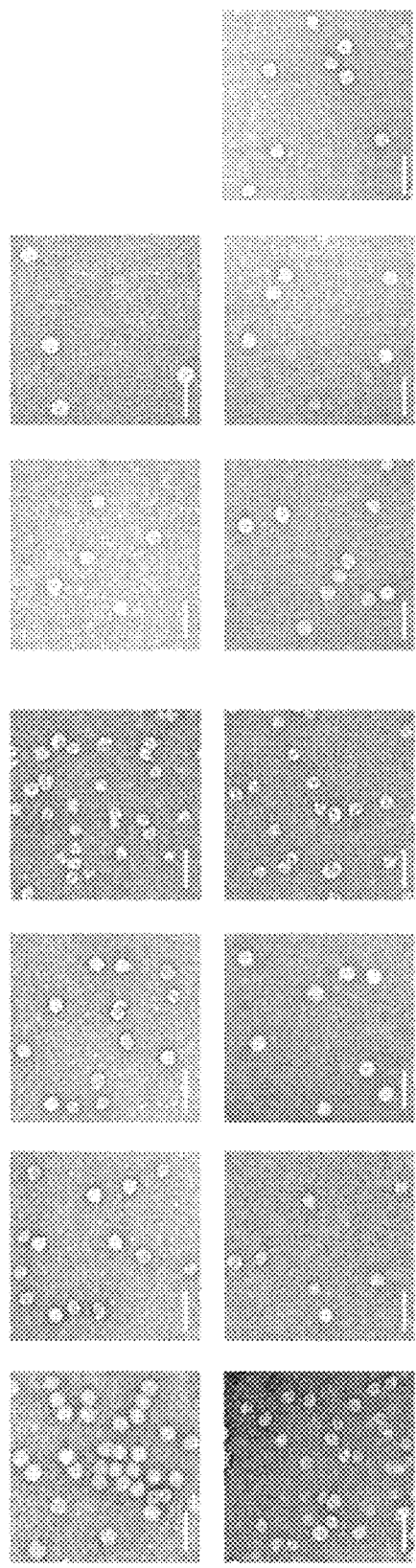
Figure 17C:
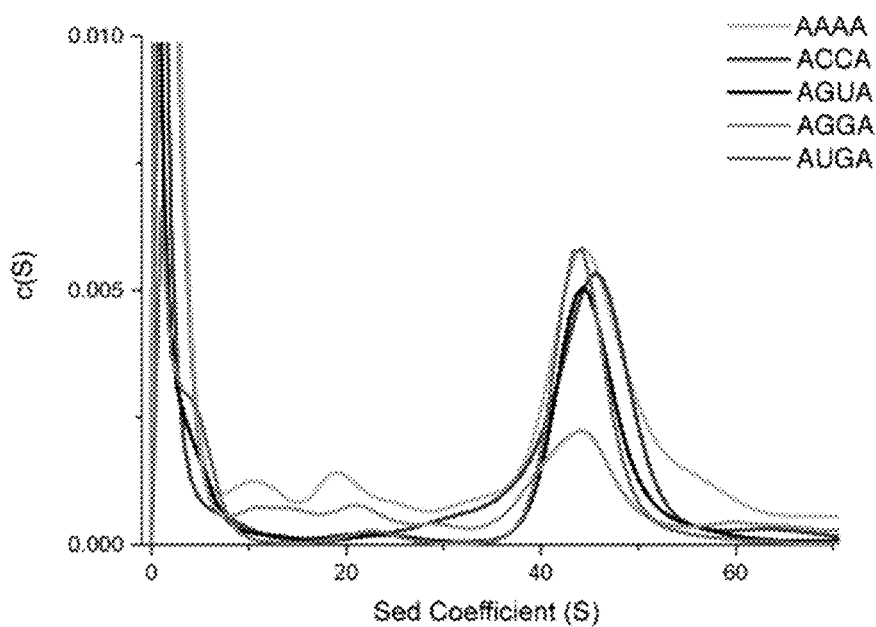
Figure 17D:
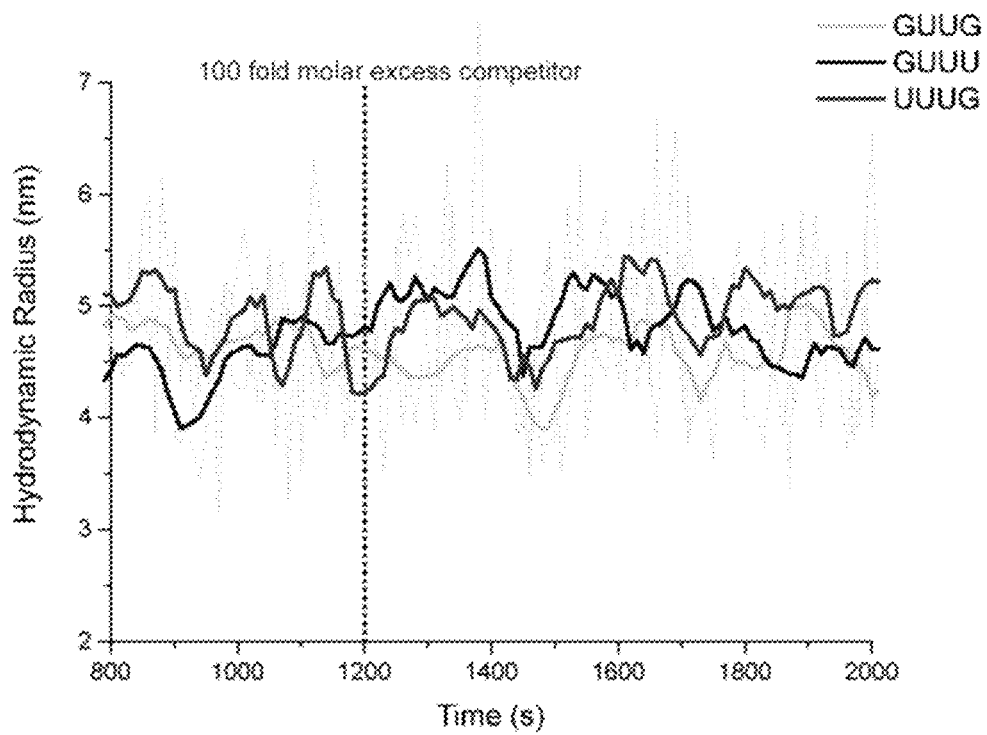
Figure 17E:
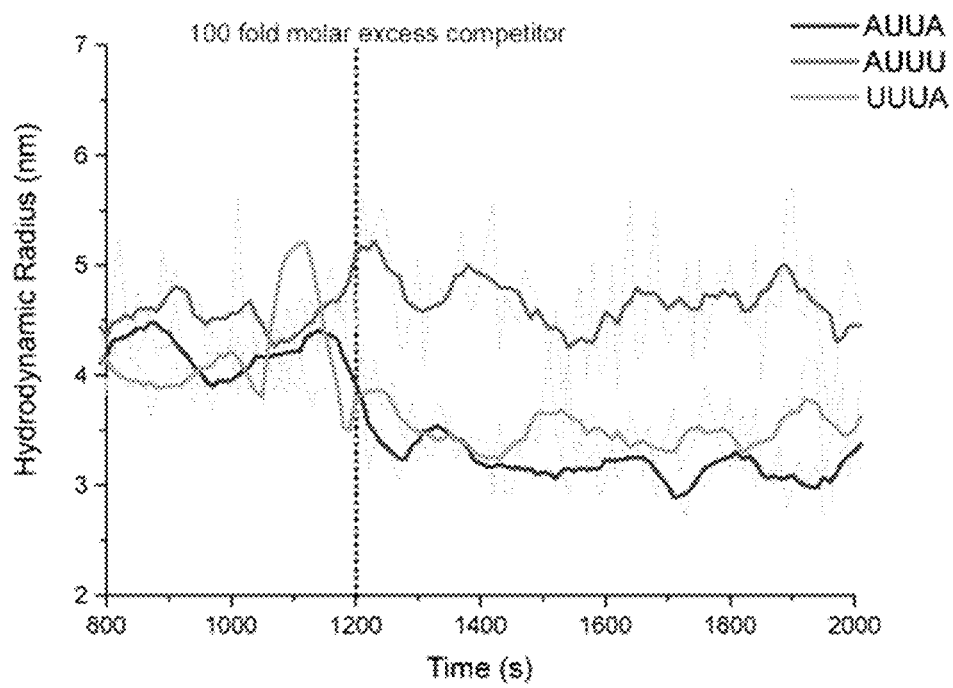
Figure 17F:
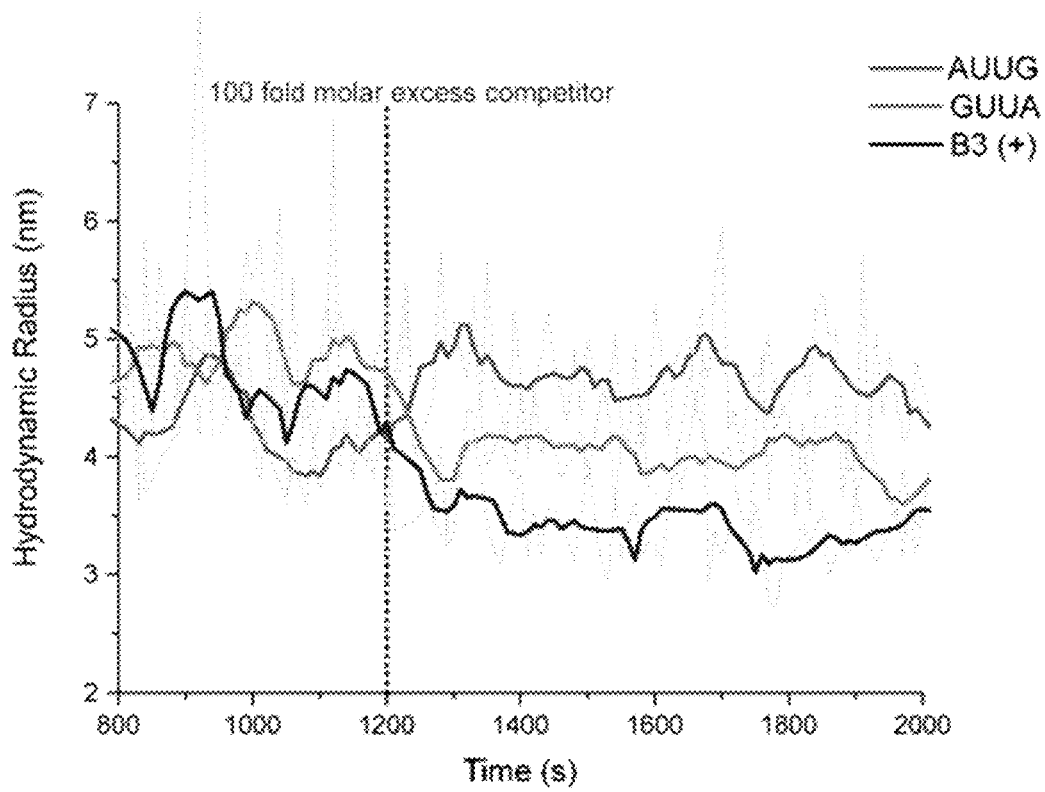
Figure 22A:
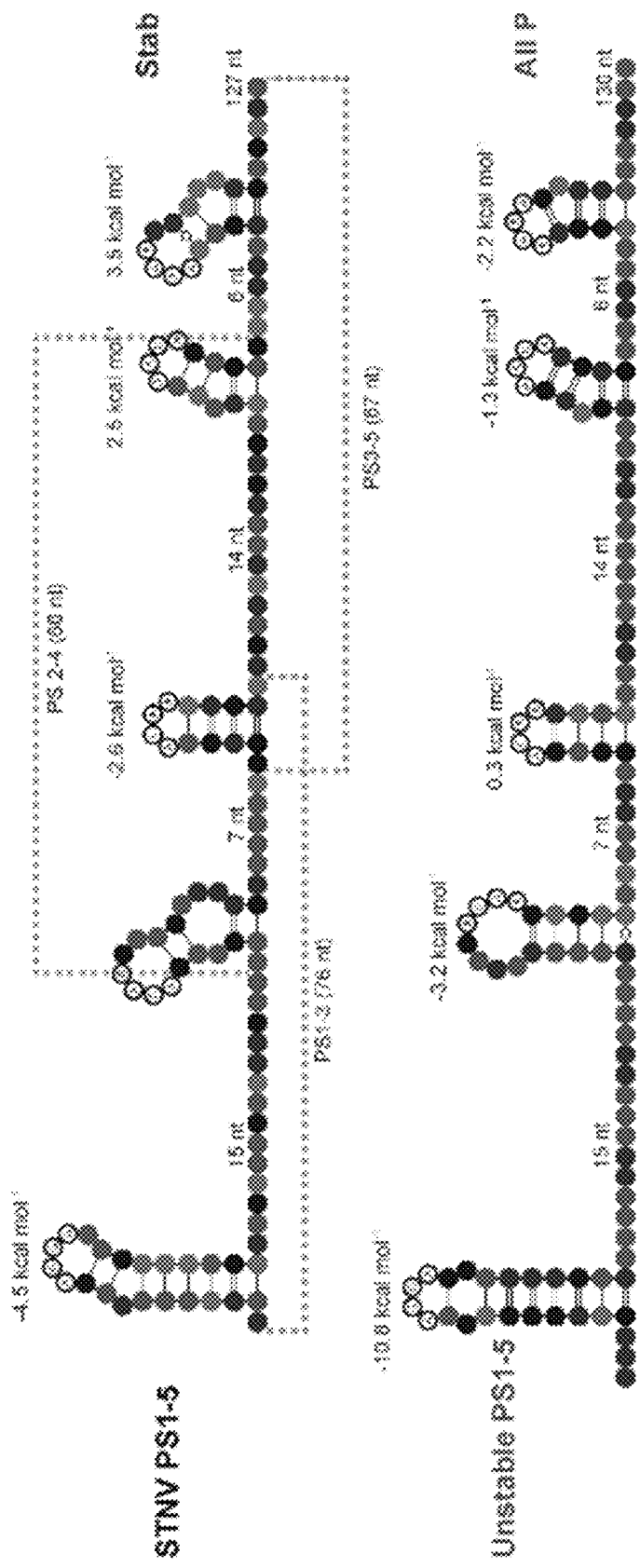
Figure 22B:
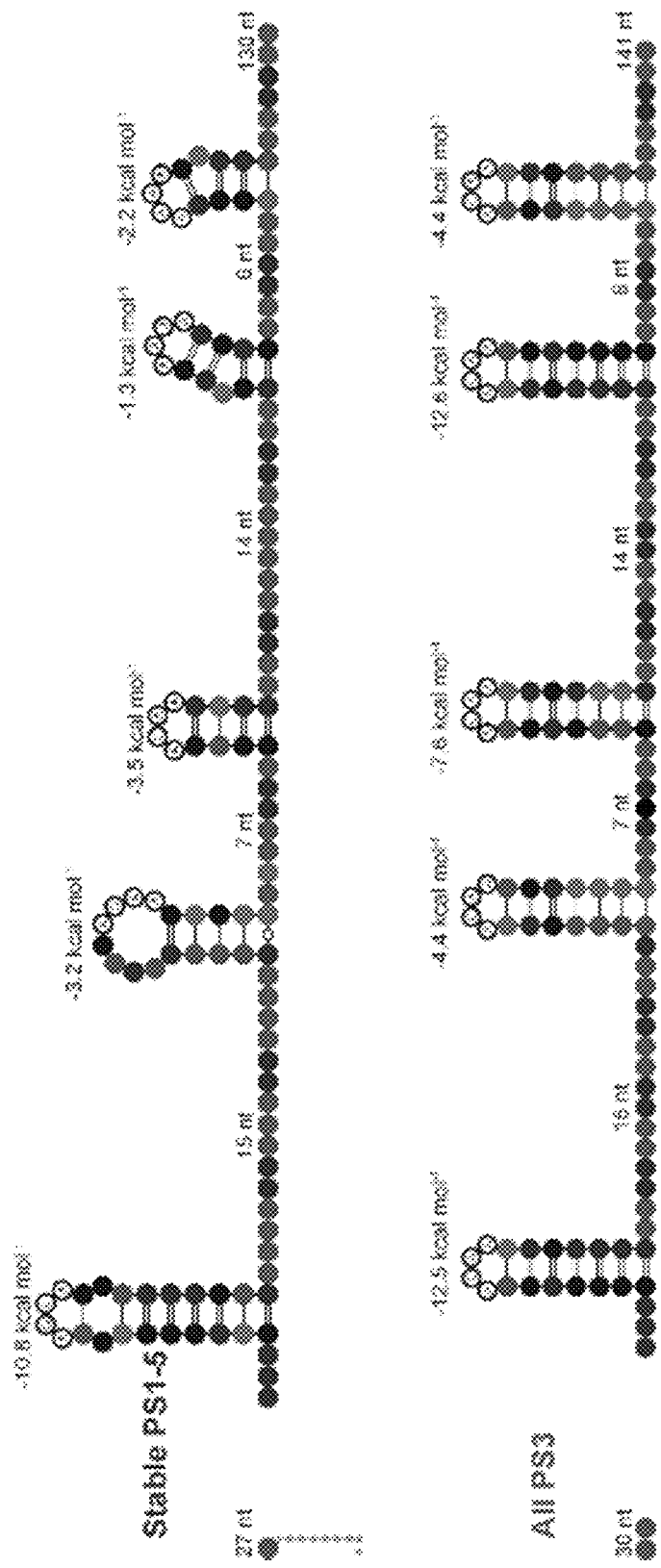
Figure 22C:
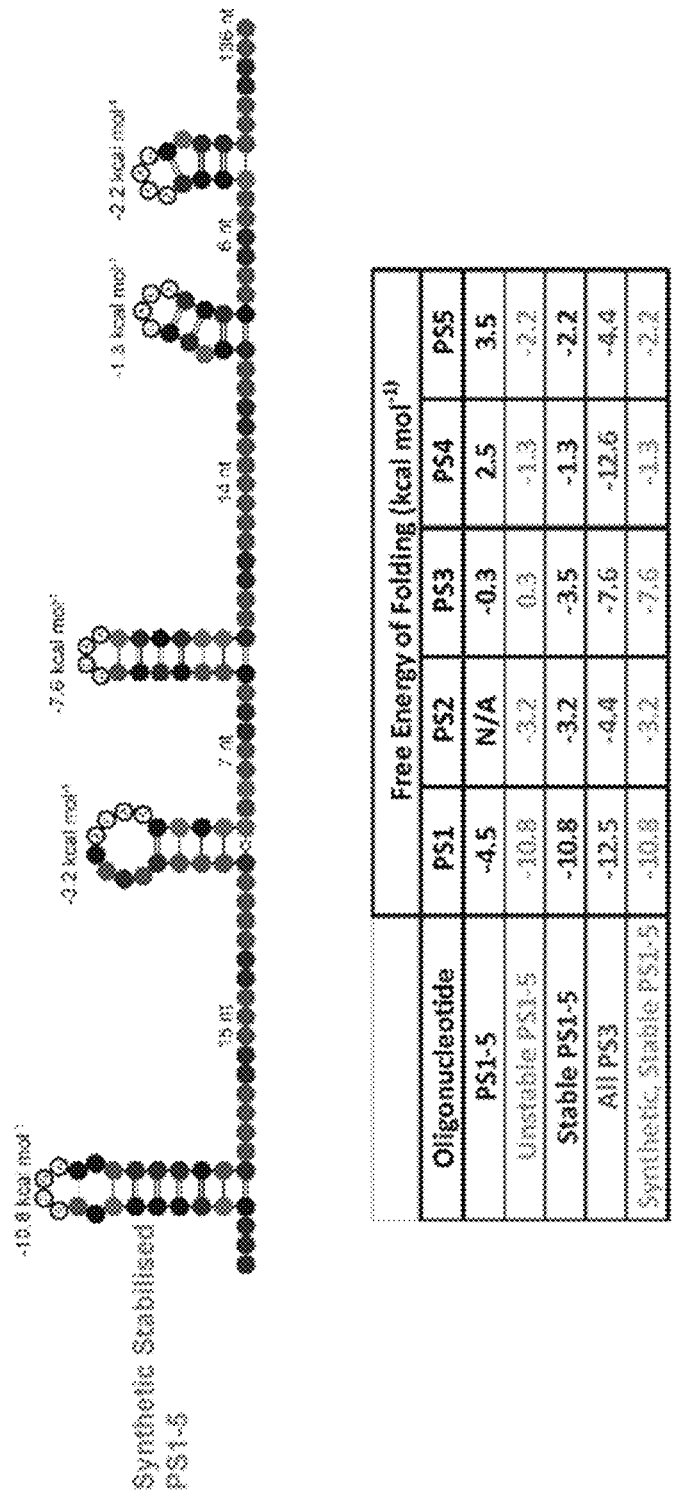

FIGS. 12A-12C: The STNV system. FIG. 12A Ribbon diagram of the STNV T=1 capsid (left, PDB 3S4G) viewed along a five-fold axis with a trimeric capsomer highlighted (dark grey) and right a CP monomer (dark grey, PDB 3S4G). Side-chains mutated here are shown and labelled. The disordered N-terminal amino acid sequence shown as a dashed line, next to the sequence of the first 25 amino acids. FIG. 12B Sequence and putative secondary structure of the 127 nt 5' STNV-1 genomic fragment showing the locations of the PS SLs, named 5' to 3' as PS1 to 5, respectively. Each contains the CP recognition motif, -A.X.X.A-, in their loops (white circles, black outline). The B3 aptamer is shown similarly above. Nucleotides are colour-coded as indicated, here and throughout (see also FIG. 22). FIG. 12C Example smFCS assays. $R_h$ values for CP-free, fluorescently-labelled RNAs (black line for PS1-5, red for B3) are determined before and during STNV CP titration at fixed time points (vertical dashed lines), allowing the $R_h$ values to equilibrate after each step. The PS1-5 $R_h$ initially collapses, by up to 30%, until the CP concentration reaches a threshold, triggering cooperative assembly to T=1 VLPs ($R_h$~11 nm). At the end of each titration, the complexes formed are challenged by addition of RNAse A. Unchanged $R_h$ values were assumed to indicate that the RNA is in a closed VLP;

FIGS. 13A-13D: Defining the CP recognition motif. FIG. 13A Ensemble reassembly efficiency of variant B3 RNAs, determined by sedimentation velocity (variant RNAs are colour-coded as inset). The expected T=1 VLP sediments at ~42 S. FIG. 13B EM images of representative assembly products, scale bar, here and throughout=50 nm, see also FIG. 17B. FIG. 13C Illustration of the variant RNA smFCS competition assay for results plotted in FIG. 13D. FIG. 13D Change in $R_h$ (in %) of a capsomer (~5 nm) formed with 1 nM AF488-labelled B3, following addition of 100-fold molar excess of competitor variant RNAs (loop sequences from top to bottom represent bars from left to right in the graph);

FIG. 14A: Electrostatic interactions and co-operativity of assembly. Wild-type or R8A CPs were titrated into B3 (1 nM) or PS1-5 (10 nM), and $R_h$ changes monitored. Titrations points are shown above (B3 in grey) and below (PS1-5), respectively. FIG. 14B Wild-type STNV CP was titrated into 10 nM of each of PS1-5, PS1-3, PS3-5 or PS2-4;

FIGS. 15A-15B: Assembly of synthetic cassettes. FIG. 15A Sequences, putative secondary structures and folding free energies of PS1-5, the Synthetic, stable PS1-5 and of the AII PS3 cassettes (FIG. 22). SLs with positive folding free energies cannot be folded by Mfold. FIG. 15B STNV CP titration of all variant PS1-5 constructs, conditions as in FIG. 14. Inset—EM images of the products with PS1-5 (black), Synthetic, stable PS3 (light grey) RNAs;

FIGS. 16A-16D: Assembly assays with genomic chimeras: FIG. 16A Schematics of the STNV-1 genome (black) and the modified variants, Synthetic, stabilised PS1-5+Δ1-127STNV-1 (bottom) and Unstable PS1-5+Δ1-127STNV-1 (middle). FIG. 16B STNV CP was titrated into 1 nM of STNV-1 (black), Synthetic, stabilised PS1-5+Δ1-127STNV-1 (light grey) or Unstable PS1-5+Δ1-127STNV-1 (dark grey), and the resulting $R_h$ was monitored using smFCS. The $R_h$ of the recombinant T=1 particle is indicated in orange. FIG. 16C The hydrodynamic radii from the data on the titration plot FIG. 16B between 4000 and 6500 secs is plotted as a distribution. FIG. 16D EM images of the products from FIG. 16B;

FIGS. 17A-17C: Assembly behaviour of B3 variants. FIG. 17A MFold structures of all B3 variants; loop sequences are given under each structure. FIG. 17B EM images of the B3 variant assemblies at 4.3 μM concentration. The scale bar shown is 100 nm. Panel positions in B correspond with the SL in the equivalent position in A. FIG. 17C Comparison of STNV CP reassembly efficiency using B3 inner variant RNAs via svAUC. Reassembly reactions were carried out at a 1:3 RNA:CP ratio with final CP concentration of 4.5 μM.

FIGS. 17D-17F: B3 Variant-capsomer competition assays. FIG. 17D 15 nM STNV CP and 5 nM Alexa Fluor® 488 fluorophore labelled B3 were used to form a capsomer of ~5 nm $R_h$. This was measured via smFCS for 1200 s. At this point 100-fold molar excess of B3 variant GUUG (light grey), GUUU (black) or UUUG (dark grey) was added and the resulting $R_h$ change tracked for 1800 s. The raw data were then used to compute the percentage change in the $R_h$ (FIGS. 13C & D). FIG. 17E as in FIG. 17D with B3 variant AUUA (dark grey), AUUU (grey) or UUUA (light grey). FIG. 17F as in FIG. 17D with B3 variant AUUG (dark grey), GUUA (light grey) or unlabeled B3 (black)

FIGS. 18A-18B: Characterisation of the STNV CP charge-change mutants: FIG. 18A SDS PAGE of charge-change mutants expressed in *E. coli*, red arrow indicates the STNV CP band. FIG. 18B svAUC of charge-change mutants purified from *E. coli*. Only mutants that produce enough VLPs (wild type, R8A and R8D (dashed [termed R8D'])) were analysed;

FIGS. 19A-19B: Assembly behaviour of STNV CP charge-change mutants with single or multiple packaging signals. FIG. 19A Top: Wild-type, R8A, R8D R14K17A or R14K17D titrated into 1 nM B3 and the resulting hydrodynamic radius monitored as described in FIG. 14. Middle: $R_h$ values from the upper chart shown as a distribution, with 0.5 nm bin sizes, were fitted with Gaussian peaks to highlight the heterogeneity present in solution throughout the reaction. The $R_h$ of a T=1 particle is indicated by the orange dashed line. Bottom: EM images of the above reactions (from left top to right bottom; Wild-type, R8A, R8D R14K17D, R14K17A. FIG. 19B(B) As in FIG. 19A but with CP titrated into 10 nM PS1-5; (from left top to right bottom; Wild-type, R8A, R8D R14K17A, R14K17D), FIG. 20: Assembly behaviour of three PS fragments. Top: $R_h$ values corresponding to 3000-4000 secs of reactions between STNV CP and PS 1-5 (black), PS 1-3 (dark grey, left), PS 3-5 (black, left) and PS 2-4 (light grey) from FIG. 14B, plotted as a distribution, with 2 nm bin sizes and fitted with Gaussian peaks. Bottom: EM images of the reactions from FIG. 14;

FIG. 21: Stable structures of the three PS fragments. Most stable structures of PS1-3, PS2-4 and PS3-5 as predicted by Mfold. Colour coding is as seen in FIG. 12 and throughout. The two main PS1-3 folds predominantly present two -A.X.X.A- SLs, however these appear to be too distant for cooperative assembly. PS2-4 presents two SLs, one with an -A.X.X.A- motif, and another one at a distance of 4 nts away from the other. The two main folds of PS3-5 also present two SLs, but whilst these SLs are in close proximity (10-12 nt), only one presents an -A.X.X.A- motif, 6% of the time;

FIGS. 22A-22C: 127-mer cassette structures. Top: sequences, putative secondary structures and folding free energies as determined by Mfold of the STNV wild-type PS 1-5 gene fragment and its synthetic counterparts. Bottom: table comparing the relative folding free energies of each SL as determined by Mfold. Oligos are colour-coded as in FIG. 12B;

FIGS. 23A-23B: Interrogation of the structure and stability of the 127-mer assembly cassettes. FIG. 23A Molar ellipticity of RNA oligonucleotides WT PS1-5 (squares), Stable PS1-5 (circles), Unstable PS1-5 (triangles), AII PS3 (inverted triangles) and Synthetic, stable PS1-5 (diamonds) at 260 nm with increasing $Ca^{2+}$ concentration. FIG. 23B Molar ellipticity at 260 nm during thermal melts of the RNA oligonucleotides, colour-coded as in FIG. 23A;

FIGS. 24A-24B: Assembly behaviour of the synthetic 127 mer cassettes. FIG. 24A The $R_h$ values between 3000-4000 secs of reactions containing STNV CP and PS 1-5 (black), stable PS 1-5 (dark grey), unstable PS 1-5 (grey), all PS3 (red) or synthetic, stable PS1-5 (light grey) from FIG. 15A, plotted as in FIG. 19. FIG. 24B EM images of the above reactions, colour coded as in FIG. 15A;

FIGS. 25A-25C: Assembly behaviour of the genomic chimeras. FIG. 25A smFCS reassembly using STNV-1 genomic RNA. $R_h$ values were measured before and during STNV CP titration (vertical dashed lines), allowing the $R_h$ values to equilibrate after each step. The STNV-1 genome initially collapses by up to ~30%, and then the $R_h$ recovers to a value corresponding to a T=1 VLP ($R_h$~11 nm). FIG. 25B QELS measured light scattering data of reassemblies between STNV-1 (black), Synthetic, stabilised PS1-5+Δ1-127STNV-1 (light grey) and Unstable PS1-5+Δ1-127STNV-1 (grey) with STNV CP eluting from a TSKgel G6000PWxl SEC column (Tosoh). Peak areas and the measured $R_h$ values are listed in Table 6. FIG. 25C EM images of the VLPs in the main peaks (~20 min).

TABLE 1

Masses of the different forms of Cp and kinase (SRPKΔ) used, as determined by ESI-MS mass spectrometry

|  | Expected mass (Da) | Observed mass (Da) |
|---|---|---|
| SRPKΔ Phosphorylated | 45615.4 | 45614.7 ± 1.37 |
| $Cp_{185}$ | 21995.4 | 21995 ± 0.71 |
| $Cp_{185}$ | 21395.3 | 21395.6 ± 0.86 |
| $Cp_{149}$ | 16852.3 | 16851.7 ± 0.06 |

TABLE 2

Association of Alexa-Fluor-488 labelled PS1 with Cp.

| Sample | Fluorescence Polarisation −RNase | Fluorescence Polarisation +RNase | Total Fluorescence −RNase | Total Fluorescence +RNase |
|---|---|---|---|---|
| PS1 oligo | 72 | 43.5 | 73637 | 74102 |
| PS1 VLP | 130 | 128 | 30187 | 33564 |
| PS1 + empty VLP | 52.8 | 15.5 | 69336 | 70672 |

Anisotropy was used to determine if 15 nM of Alexa-Fluor-488 labelled RNA PS oligos can bind to, or enter, 125 nM of preformed shells of Cp. The latter were formed by reassembly in the absence of RNA at high concentration(3) (FIG. 8c). Fluorescence polarisation values are influenced by the mass of the dye-labelled species(4). The polarisation value for PS1 oligo goes down following addition of RNase, as expected but remains unchanged when incorporated in VLPs assembled in the presence of the oligo. When labelled PS1 is added to the empty Cp VLP its fluorescence emission is unaffected, suggesting that it is not quenched, and it remains RNase sensitive confirming that it does not bind the outside of the protein shell or get internalised.

TABLE 3

Sequence changes and corresponding assembly behaviour of PS1 variant oligonucleotides, L1-5 and B1. Assembly behaviour is indicated as follows, the first "+" indicates RNA-Cp binding, the second signifies formation of T = 3/T = 4 sized species, and the third indicates RNase protection. "−" indicates failure in that assay.

| RNA Oligo | Loop | Bulge | Assembly behaviour | Comment |
|---|---|---|---|---|
| PS1 | GGGAGG | GGG | + + + | |
| L1 | UUUAUU | GGG | + − − | Loop G's are important |
| L2 | GUUAGG | GGG | + − − | Loop G's are important |
| L3 | UGGAUU | GGG | + + − | Loop G's are important |
| L4 | GGGUGG | GGG | + + − | Loop A is important |
| L5 | GGGGGG | GGG | + + − | Loop A is important |
| B1 | GGGAGG | AAC | + + − | Bulge sequence/structure is important |

TABLE 4

B3 sequence variants. Loop motif (left), full sequence (middle) and folding free energy values (right) of the B3 sequence variants.

| Loop motif | Sequence | ΔG of folding (kcal mol$^{-1}$) |
|---|---|---|
| ACAA | ACAUGCAACAAUGCACAC (SEQ ID NO 10) | −2.6 |
| AUUU | ACAUGCAAUUUUGCACAC (SEQ ID NO 11) | −2.6 |
| UUUA | ACAUGCAUUUAUGCACAC (SEQ ID NO 12) | −2.6 |
| GUUU | ACAUGCAGUUUUGCACAC (SEQ ID NO 13) | −2.1 |
| UUUG | ACAUGCAUUUGUGCACAC (SEQ ID NO 14) | −2.9 |
| AUUG | ACAUGCAAUUGUGCACAC (SEQ ID NO 15) | −2.6 |
| GUUA | ACAUGCAGUUAUGCACAC (SEQ ID NO 16) | −3.4 |
| GUUG | ACAUGCAGUUGUGCACAC (SEQ ID NO 17) | −2.5 |
| AUUA | ACAUGCAAUUAUGCACAC (SEQ ID NO 18) | −2.6 |

TABLE 5

Analysis of suboptimal structures of RNA assembly cassettes. Mfold was used to fold each cassette with a suboptimality setting of 500. These folds were then assessed by the following criteria: The presence of the correct -A.X.X.A- loop in PSs 1 through 5 were verified and shown as a percentage (green = 60+, orange = 40+, red 0-39 throughout the table). The nucleotide spacing between each stem loop was measured, compared to the expected value (FIG. 22) and also displayed as a percentage. Where these spacings differed, the maximum nucleotide difference is given.

| Cassette | % of Correctly presented -A.X.X.A- motifs PS1 | PS2 | PS3 | PS4 | PS5 | % of 'correct' spacings 1-2 | 2-3 | 3-4 | 4-5 | Maximum spacing variance |
|---|---|---|---|---|---|---|---|---|---|---|
| WT PS1-5 | 72 | 0 | 8 | 0 | 10 | 8 | 0 | 0 | 0 | +7 |
| Synthetic Stable PS1-5 | 100 | 87 | 100 | 75 | 73 | 9 | 69 | 76 | 72 | +7 |
| Stable PS1-5 | 100 | 87 | 99 | 68 | 31 | 5 | 72 | 55 | 66 | +7 |
| Unstable PS1-5 | 98 | 97 | 0 | 73 | 27 | 73 | 0 | 0 | 67 | +7 |
| All PS3 | 100 | 99 | 100 | 100 | 100 | 92 | 90 | 100 | 90 | +4 |
| PS1-3 | 78 | 2 | 9 | N/A | N/A | 0 | 0 | N/A | N/A | N/A |
| PS2-4 | N/A | 0 | 2 | 0 | N/A | N/A | 0 | 0 | N/A | +3 |
| PS3-5 | N/A | N/A | 34 | 4 | 6 | N/A | N/A | 0 | 0 | N/A |

TABLE 6

Yield and $R_h$ values from QELS experiments. Measured $R_h$ values taken from the midpoint of the main peak (20 min, FIG. 25) eluted from the TSKgel G6000PWxl column. Yields of genomic chimera reassemblies were calculated by integrating the area under the main peak (20 min, FIG. 25) using the peak analyser function in Origin Pro 9. Yields were then normalised to the highest value and shown as percentages.

| Sample | $R_h$ value/nm | Relative Yield/% |
|---|---|---|
| STNV-1 | 9.1 | 80 |
| Unstable PS1-5 + Δ1-127 STNV-1 | 8.9 | 40 |
| Synthetic, Stabilised PS1-5 + Δ1-127 STNV-1 | 9.3 | 100 |

TABLE 7

RNA oligonucleotide primers

| Primer Name | Sequence 5'-3' | SEQ ID NO | Tm °C. |
|---|---|---|---|
| Forward | GACATTAATACGACTCACTATAGGGACATGCA | 19 | 65.5 |
| AUUArev | GTGTGCATAATTGCATGTCCCTATAGTGAGTCG | 20 | 68.2 |
| GUUGrev | GTGTGCACAACTGCATGTCCCTATAGTGAGTCG | 21 | 70.0 |
| AUUGrev | GTGTGCACAATTGCATGTCCCTATAGTGAGTCG | 22 | 69.5 |
| GUUArev | GTGTGCATAACTGCATGTCCCTATAGTGAGTCG | 23 | 69.5 |
| UUUArev | GTGTGCATAAATGCATGTCCCTATAGTGAGTCG | 24 | 68.2 |
| AUUUrev | GTGTGCAAAATTGCATGTCCCTATAGTGAGTCG | 25 | 68.2 |
| GUUUrev | GTGTGCAAAACTGCATGTCCCTATAGTGAGTCG | 26 | 69.5 |
| UUUGrev | GTGTGCACAAATGCATGTCCCTATAGTGAGTCG | 27 | 69.5 |
| ACCArev | GTGTGCATGGTTGCATGTCCCTATAGTGAGTCG | 28 | 64.3 |
| AAAArev | GTGTGCATTTTTGCATGTCCCTATAGTGAGTCG | 29 | 62.0 |
| AGGArev | GTGTGCATCCTTGCATGTCCCTATAGTGAGTCG | 30 | 64.0 |
| AUGArev | GTGTGCATCATTGCATGTCCCTATAGTGAGTCG | 31 | 62.9 |
| AGUArev | GTGTGCATACTTGCATGTCCCTATAGTGAGTCG | 32 | 62.5 |
| Unstable 1-5 forward | AGTAATACGACTCACTATAGGGGGCTGCCCTCAAGGACCAGGGCAGAAAAGAGGAAAAGAA | 33 | 62 |
| Unstable 1-5 template | GGCAGAAAAGAGGAAAAGAAAAGTGACAGAACACTTATAAGGAAATACACAAGTATAAGGAAAAAAGGAAGCTGCAATAGCGCAAGGAA | 34 | 62 |
| Unstable 1-5 reverse | TTCCTTTCCGAATTTTCGGATTCCTTGCGCTATTGCAGCTT | 35 | 62 |
| All PS3 forward | GGGCCCCGCAACAATGCGGGGAAGGAAGGAAGGAAGAAAACGTACAAACGTTTT | 36 | 65 |
| All PS3 template | AGAAAACGTACAAACGTTTTAAGGAACAACGCAACAATGCGTTGAAGGAAGGAAGGAAGGGGCGTACAAACGCCCCAAGGAATTTT | 37 | 65 |
| All PS3 reverse | TTCCTTTTTTGCATTGTTGCAAAATTCCTTGGGGCGTTTGTACGC | 38 | 65 |
| Stable 1-5 template | GGCAGAAAAGAGGAAAAGAAAAGTGACAGAACACTTATAAGGAACCACACAAGTGGAAGGAAAAAAGGAAGCTGCAATAGCGCAAGGAA | 39 | 62 |
| Synthetic stable 1-5 template | GGCAGAAAAGAGGAAAAGAAAAGTGACAGAACACTTATAAGGAAAAACGUACAAACGUUUUAAGGAAAAAAGGAAGCTGCAATAGCGCAAGGAA | 40 | 62 |

TABLE 7-continued

RNA oligonucleotide primers

| Primer Name | Sequence 5'-3' | SEQ ID NO | Tm °C. |
|---|---|---|---|
| PS1-5 forward | AGTAATACGACTCACTATAGGGAGTAAAGACAG GAAACTTTACTGACTAACATGGCAAAAC | 41 | 62 |
| PS1-5 template | ACTGACTAACATGGCAAAACAACAGAACAACAG GCGAAAATCCGCAACAATGCGTGCAGTGAAGC GCATGATAAATACAC | 42 | 62 |
| PS1-5 reverse | TCAGTGCAAACCTTTTATGCTCCAAGTGTGTAT TTATCATGCGCT | 43 | 62 |
| PS1-3 forward | AGTAATACGACTCACTATAGGGAGTAAAGACAG GAAACTTTACTGACTAACATGGCAAAAC | 44 | 61 |
| PS1-3 template | ACTGACTAACATGGCAAAACAACAGAACAACAG GCGAAAAT | 45 | 61 |
| PS1-3 reverse | CGCATTGTTGCGGATTTTCGCCTGTTGT | 46 | 61 |
| PS2-4 forward | AGTAATACGACTCACTATAGGGTGGCAAAACAA CAGAACAACAGGCGAAAAT | 47 | 58 |
| PS2-4 template | AACAGAACAACAGGCGAAAATCCGCAACAATGC GTGCAGTGAAGCGCATGATAAATA | 48 | 58 |
| PS2-4 reverse | CCAAGTGTGTATTTATCATGCGCTTCACTGCAC GCATTGTTGCGG | 49 | 58 |
| PS3-5 forward | AGTAATACGACTCACTATAGGGCCGCAACAATG CG | 50 | 61 |
| PS3-5 template | CCGCAACAATGCGTGCAGTGAAGCGCATGATA AATACAC | 51 | 61 |
| PS3-5 reverse | TCAGTGCAAACCTTTTATGCTCCAAGTGTGTAT TTATCATGCGCT | 52 | 61 |

Materials and Methods

Cloning, Expression and Purification of Proteins Used.

We obtained an *E. coli* Cp-expressing plasmid (a gift of Prof. Nicola Stonehouse), known to produce assembled HBV VLPs containing host RNAs(5). The Cp encoded has the following amino acid sequence differences compared to the current GenBank reference strain (NC_003977.2): A61, E77-FAGAS (single letter amino acid code)-D78 insertion, S92N, F102I, I121L, R156-RD-R157 insertion. Since the wild-type C61 has been implicated in assembly (6), this was restored to the gene before expression in a PET28b plasmid in BL21 (DE3) *E. coli* cells. The inserted FAGAS epitope was also removed. Induction with 1 mM IPTG at 0.6 OD was followed by growth for 20 hrs at 21° C. Cells were lysed using a Soniprep 150 with 5× 30 sec bursts on ice. The lysate was then clarified by spinning at 11,000 g for 1 hr. VLPs were then pelleted by centrifugation at 120,000 g for 14 hr, resuspended in 20 mM Hepes (pH 7.5), 250 mM NaCl, and 5 mM DTT and applied to an XK50 column packed with 25 ml of Capto™ core 700 resin (GE Life Sciences). Fractions containing VLPs were pooled and precipitated with 40% (w/v) ammonium sulphate. The Cp appeared pure on SDS-PAGE and its identity, and that of variants, was confirmed by mass spectrometry (Table 1). Cp lacking the ARD, i.e. $Cp_{149}$, was produced by mutagenesis (Q5 site-directed mutagenesis kit, NEB) and prepared similarly. Note, the $Cp_{149}$ VLP expressed in *E. coli* lacks significant encapsidated cellular RNA. VLPs were visualised by negative stain transmission electron microscopy (TEM). Full length Cp VLPs were additionally purified by sucrose density gradient before dye-labelling using Alexa Fluor®-488 SDP ester fluorophore (Invitrogen) over 4 hrs at room temperature in 200 mM sodium carbonate buffer (pH 8.3), followed by desalting over a NAP5 column. There were two over-lapping VLP peaks on the gradient and it was impossible to separate them. TEM and smFCS confirm that they are the expected T=3 and T=4 shells, with the latter the predominant form (FIG. 7a). The Cp region 140-148 has been shown to be a determinant of morphology, the shorter versions producing more T=3 shells (7). It is possible that the dipeptide insertion adjacent to the linker region at position 157 may alter the properties of the Cp. However, when we removed the RD insertion, yielding $Cp_{183}$, we found no differences with $Cp_{185}$, either in RNA binding, ability to form VLPs with PS RNAs or preference for the dominant quasi-conformer shell formed. Since longer Cp was used for SELEX and the high resolution EM work, those are the data shown throughout.

All HBV variants used for assembly assays were dissociated from VLPs into protein dimers as previously described(3), with the exception that dissociation was at pH 9.5, as opposed to 7.5. This was done in the presence of Complete Protease Inhibitor Tablets (Thermofisher Scientific). HBV core dimer concentration was determined by UV absorbance. Fractions with an $A_{260}$:$A_{280}$ ratio of approximately 0.6 or lower were used in assembly assays. SRPKΔ kinase was expressed and purified from a pRSETb plasmid, as previously described(8).

SELEX Protocol

Purified HBV capsids (~360 μg) were immobilised onto 6 mg of M270 carboxylic acid Dynabeads® microspheres (Thermo Fisher Scientific) following the manufacturer's protocol. Beads were washed twice with selection buffer (25 mM Hepes, pH 7.5, 250 mM NaCl, 2 mM DTT, EDTA-free complete protease inhibitor) and unreacted N-hydroxysuccinamide blocked with a 15 m 50 mM Tris-HCl pH 7.4 wash. Beads were washed a further three times with selection buffer. Immobilised capsids were dissociated with a 30 minute incubation of 2 M guandinium chloride in 0.5 M $LiCl_2$. Beads were then washed three times with B&W buffer (10 mM Tris-HCl, pH 7.5, 1 mM EDTA, 2 M NaCl) and then washed three times with selection buffer. Beads were resuspended in selection buffer so that concentration of beads was 10 mg/mL. Negative selection beads were also prepared in the same manner but with no capsids. Ten rounds of SELEX were performed in vitro using a synthetic, combinatorial N40 2'OH RNA library (~$10^{24}$ potential sequences) as described previously (9). The amplified DNA of round 10 was then subjected to Next Generation Sequencing on an Illumina MiSeq® sequencing-platform. This yielded ~1.6M sequence reads, in which one sequence occurs 65,802 times and there are 1149 aptamers with a multiplicity of 100 or higher. The overall frequencies of the four nucleotides in this aptamer pool is A34.30%; C9.09%; G40.97% & U15.64%, and compares with the same data for the unselected naïve library of A26.10%; C22.03%; G24.64% & U27.22%. The highest multiplicity for sequences in the latter pool is 4. These data confirm that selection from the naïve pool occurred, and that the base composition of the selected aptamers is consistent with the RGAG motif identified within the HBV genomes.

PS Identification

PS identification was carried out using the laboratory HBV strain (*NC_003977.1). The aptamer library contained 1,664,890 unique sequences, each 40 nts in length that have been aligned against the genome as follows: Each aptamer sequence was slid along the genome in increments of 1 nt. For each such position of the reference frame, the subset of the aptamer sequence with the best alignment to the genome was identified according to the Bernoulli score B, which benchmarks the probability of a non-contiguous alignment to that of a contiguous alignment of B nucleotides. The Bernoulli scores for all reference frames of a given aptamer sequence in the library were rank-ordered starting from the largest score, and all matches with the genome up to a Bernoulli score of 12 counted. The procedure was then repeated for the other aptamer sequences and corresponding matches added, resulting in the peaks in FIG. 2a.

Identification of a Consensus Motif

HBV genome sequences with the following accession numbers were randomly extracted from 750 complete HBV genomes found in GenBank: KCS10648.1; *AF223955.1; AY781181.1; *AB116266.1; AB195943.1; KR014086.1; *KR014072.1; KR014055.1; KR013939.1; KR013921.1; KR013816.1; KR013800.1; EU796069.1; AB540582.1, and the NCBI HBV reference strain (GenBank Seq ID *NC_003977.2) and the laboratory strain (GenBank Seq ID NC_003977.1) were added to the ensemble. Sequences used for the statistical analysis in FIG. 2c are marked by an asterisk. Bernoulli peaks, which occurred within at most 10 nts of each other in at least 80% of these 16 HBV strain variants, were marked by a green cross in FIG. 2a to indicate their conservation. To identify the putative PS recognition motif, we extracted sequences of 60 nts, centred around the peak nucleotide of each Bernoulli peak, from three representative strains (AF223955.1, NC_003977.1, & NC_003977.2) and determined all possible stem-loops of negative free energy via Mfold(10). We carried out a similarity analysis of these stem-loops, comparing both sequence and structure elements, we identified for each peak area that representative that has the highest degree of similarity both with secondary structure elements in the other peak areas in the same genome and stem-loops corresponding to the same peak area in the other strains. This returned a stem-loop for each peak. An alignment of the corresponding loop sequences is shown in FIG. 2b.

RNA Dye-Labelling

PS1, PS2 and PS3 (47 nucleotides long) were purchased from Integrated DNA Technologies with a 5' C6-amino group. To label RNA, 6 μL of RNA (200 μM) was mixed with 1 μL 1 M sodium borate buffer, pH 8 and 3 μL 10 mM Alexa Fluor®-488-SDP fluorophore (Thermo Fisher Scientific) and rolled at room temperature for 4 hours. 10 μL of 2× denaturing loading dye was then added to the RNA, boiled for 5 minutes and loaded onto a pre-warmed denaturing PAGE. RNA was gel extracted, isopropanol precipitated and finally re-suspended in DEPC-$H_2O$ and frozen at −80° C. until needed.

Assembly Assays

Assembly reactions were performed by adding HBV Cp in dissociation buffer (50 mM Tris (pH 9.5), 1.5 M GuHCl, 500 mM LiCl and 5 mM DTT) to 15 nM Alexa Fluor®-488 fluorophore labelled RNA in a reassembly buffer containing 20 mM Hepes (pH 7.5), 250 mM NaCl, 5 mM DTT and 0.05% (v/v) Tween®-20 polysorbate emulsifier at 25° C. Successive additions of dimer were performed until assembly was deemed complete by the measured $R_h$ value plateauing, but never exceeded 10% of total reaction volume. Each addition of Cp is marked by a vertical dashed grey line in the titration plots and the expected hydrodynamic radii of T=3 and T=4 particles (as determined for dye-labelled particles expressed in E. coli) are marked by an orange horizontal dashed line within figures.

Manual mixing throughout the reactions caused an approximate 1 min delay at the start of FCS data collection. FCS measurements were made using a custom-built FCS setup with 30 sec data accumulation per autocorrelation function (CF). Individual CFs were decomposed into triplet state relaxation and diffusion (characterized by diffusion time, TD) components, and the latter was converted into an apparent hydrodynamic radius, $R_h$(11). Samples for TEM were taken at the end of each measurement. Plots of $R_h$ over time (thin dashed line) were smoothed (thick solid line) using the FFT filter in Origin Pro-8 with a cutoff percentage of 35%. Plots of $R_h$ distribution were also fitted using Origin Pro-8 software, to a normal single or multiple peak Gaussian function. Samples taken for negative stain TEM analysis were placed on to a glow discharged carbon coated formvar 300 mesh Cu grid. Grids were stained with 2% uranyl acetate and dried.

Assembled Particle Labelling

Assembly was carried out as in smFCS experiments. In particular, Cp was titrated into reassembly buffer with and without 15 nM unlabelled PS1 to a final concentration of 250 nM. This was allowed to incubate at room temperature for 1 hour, and then buffer exchange was carried out via dialysis to remove guanidinium hydrochloride present. Labelling of protein was then carried out by adding Alexa Fluor®-488 SDP ester fluorophore (1:50 ratio of dye to Cp dimer) and incubating overnight at 4° C. The resulting sample was then measured via smFCS in 30 s bins for 100 min and the $R_h$ data plotted as above in a hydrodynamic radial distribution plot.

A sample was then removed for analysis via TEM. Post labelling, Cp dimer became assembly incompetent, therefore Cp could not be tracked during real time assembly.

Photobleaching

HBV VLPs containing Alexa-488 labelled PS1 were assembled as described in smFCS assembly assays. Under those conditions all RNA is bound to protein as judged from fluorescence quenching and photon counting in the FCS experiments. VLPs were then added to two glow discharge-irradiated Carbon/Formvar 300-mesh grids (Agar Scientific), and one grid stained with 2% (w/v) uranyl acetate and viewed with a Jeol 1400 microscope at 40,000× magnification. The remaining, unstained grid was positioned Formvar side down onto a clean microscope coverslip and mounted onto an inverted TIRF microscope. The laser (Coherent Sapphire, 488 nm, 25 mW) power was adjusted to excite and photobleach the labelled RNA within the time frame of several minutes. Sequential images were taken with an emCCD camera (Andor iXon) with 0.2 sec exposures and em gain of 200. An unexposed field of view was used for each series.

Fluorescent spots were identified in the collected frames using previously described procedures and converted into time traces(12). These were then inspected and classified according to the number of photobleaching steps. Frequencies of traces with a defined number of steps were collated in a histogram. Several bright spots per field of view exhibited continuous intensity decay, presumably representing larger aggregates. These were used to estimate the overall photobleaching rate (0.003 per frame) and formally included in the histogram as representing 10 steps. The histogram without the bin representing continuum events was modelled as a weighted sum of binomial distributions for up to quadruple occupancy and probability of labelling of 0.56 estimated from UV-Vis spectra.

Electron Microscopic Reconstructions

Large Scale VLP Preparation smFCS experiments were scaled up into 96 well plates. Two 96 well plates (Non-Binding Surface, Corning) were used. PS1 RNA was labelled and gel purified as described earlier and HBV dimer was purified as described above. Each well contained 200 µL of 15 nM PS1 in reassembly buffer. As in smFCS, ten 2 µL injections of 2.5 µM dimer in dissociation buffer were performed. A Perkin-Elmer Envision plate reader was used to carry out the injections and record the anisotropy of the PS1 RNA (FITC excitation and emission filters). VLPs were purified away from free RNA and capsid using a 1.33 g/mL caesium chloride gradient and spun at 113,652×g for 90 hours using an SW40Ti rotor. A single band was observed and fractionated. The band was dialysed into reassembly buffer to remove caesium chloride. The 2 mL fraction of VLP was concentrated to 200 µL using an Amicon 100 kDa MWCO spin concentrator.

CryoEM Specimen Preparation

After recovery of the PS1-containing VLPs and removal of caesium chloride by dialysis, their structures were analysed using single-particle cryo-EM. VLPs were vitrified. 200 mesh EM grids with Quantifoil R 2/1 support film and an additional ~5 nm continuous carbon film were washed using acetone and glow discharged for 40 s prior to use. CryoEM grids were prepared by placing 3 µl of ~3.2 mg/ml HepB VLP on the grid, before blotting and plunge freezing using a Leica EM GP freezing device. Chamber conditions were set at 8° C. and 95% relative humidity, with liquid ethane temperature at −175° C. Data was collected on a FEI Titan Krios (eBIC, Diamond Light Source, UK) transmission electron microscope at 300 keV using an electron dose of 27 $e^-/Å^2/s$, 2.5 s exposure, yielding a total electron dose of 67.5 $e^-/Å^2$. Data was recorded on a 17 Hz FEI Falcon 11 direct electron detector. The dose was fractionated across 33 frames. Final object sampling was 1.34 Å per pixel. A total of 2397 micrographs were recorded using EPU (FEI) automated data collection software.

Single Particle Image Processing 2397 micrographs were motion corrected and averages of each movie were generated using MotionCorr(13), and contrast transfer function (CTF) parameters for each were determined using CTFFIND4(14). Micrographs with unacceptable astigmatism or charging, as determined by examining the output from CTFFIND4, were discarded leaving a total dataset of 1710 micrographs. All particle picking, classification and alignment was performed in RELION 1.3(15).

Approximately 57,000 particles were manually picked and classified using reference-free 2D classification in RELION 1.3. This classification confirmed the initial visual impression that although the VLPs were purified as a single band on a caesium gradient, two sizes of VLPs were present. A selection of resulting 2D class averages were used as templates for automated particle picking. The particle stack generated using auto-picking was subject to 2D classification to separate T=3 and T=4 particles, and to remove particles not corresponding to VLPs. The subsequent particle stacks (5589 for T=3, 42,411 for T=4) were subject to 3D classification, using a sphere with the approximate diameter of the VLP as a starting model. Subsets of the data were reconstructed including data out to the Nyquist frequency using the 3D autorefine option in RELION with 13 symmetry imposed to generate all structures presented in this work. Within the T=4 42,411 particle dataset it was clear that a further subset (10,851 particles) of the data contained a significant asymmetric feature inside the Cp shell where RNA binding would be expected to occur. An asymmetric (C1) reconstruction was performed on a relatively homogenous set of 10,851 such particles, giving the reconstruction at 11.5 Å resolution.

The 3D model of PS1 RNA was made using RNA Composer(16). The cryoEM figures were rendered using USCF Chimera(17).

Purification of Recombinant STNV CPs

Recombinant STNV VLPs were purified from *E. coli*(18). STNV charge-change mutant plasmids were created using primers designed using Agilent, and a Quikchange site directed mutagenesis kit (Agilent). CP monomers were purified by disassembly in 50 mM Tris (pH 8.5), 10 mM EDTA, in the presence of Complete Protease Inhibitor Cocktail (Roche, United Kingdom). STNV CP was separated from the mRNA by sequential Q-Sepharose, and SP-Sepharose columns (GE Healthcare, Sweden). STNV CP was washed with 20 column volumes of 50 mM HEPES (pH 7.5) and 25 mM NaCl to remove residual EDTA, and subsequently eluted using a 0.025-2 M NaCl gradient in buffer. CP elutes at 0.8 M NaCl. STNV CP was analysed by SDS-PAGE and its concentration determined by UV absorbance. Fractions with an A260:A280 ratio of 0.6 or lower were used in assembly assays. Mutant CPs that did not form VLPs during overexpression were purified using the same sequential Q-Sepharose and SP-Sepharose columns method.

Preparation of RNA Oligonucleotides dsDNA transcripts encoding the RNA oligonucleotides used in this study were produced using primers and the KAPA2G system (KAPA biosystems) following the manufacturer's protocol. Transcriptions were carried out using the HiScribe® T7 High yield RNA synthesis kit (NEB). Products were run on a denaturing RNA gel. The Alexa Fluor®-488 fluorophore labelled B3 oligonucleotide used throughout was synthesised and HPLC purified by DNA Technology A/S (Denmark). Other RNA oligonucleotides requiring a 5' fluorophore were labelled with an amino GMP during transcription and cross linked to an Alexa Fluor®-488 SDP ester fluorophore (Invitrogen) prior to gel purification as described previously (19).

Genomic chimeras were created by purchasing Gene blocks of the Synthetic, stabilised and Unstable+Δ1-127 STNV-1 constructs with a 5' T7 promoter (Integrated DNA technologies), possessing BamHI and HindIII cleavage sites at either end to create sticky ends after restriction digestion and dephosphorylation using Antarctic phosphatase (NEB). This gene block was then ligated into a PACYC184 plasmid using T4 DNA ligase (NEB). Transcription was carried out as above after linearization using BamHI.

RNA was annealed prior to each experiment by heating to 80° C. for 90 s and cooling slowly to 4° C. in a buffer containing 50 mM NaCl, 10 mM HEPES and 1 mM DTT at pH 7. Genomes were only heated to 65° C.

STNV Reassembly in the Presence of B3 Variants and Sedimentation Velocity Analytical Ultracentrifugation (svAUC) Reassembly reactions were carried out in the presence and absence of B3 variants in a 1:3 RNA:CP ratio at a final CP concentration of 4.5 µM, by dialysis into a buffer containing 50 mM HEPES (pH 7.5) and 2 mM Ca2+. All samples were analysed by TEM and AUC. For AUV, 0.32 mL of each sample was placed in a 1.2 cm path length 2-sector meniscus matching epon centrepiece cell constructed with sapphire windows. The samples were centrifuged at 15,000 rpm in an Optima XL-1 analytical ultracentrifuge at 20° C. in an An50-Ti rotor. Changes in absorbance at 260 nm were detected by absorbance optics with 100 scans taken in approximately 11 hrs 30 min. Data were fitted and analysed using the program Sedfit.

smFCS Data Collection and Analysis

FCS measurements were performed on a custom-built smFCS facility. Excitation laser (Sapphire CW blue laser, 488 nm, Coherent, USA) power was set to 65 µW. The focus position was adjusted to 20 µm from the cover slip inner surface (maintained by piezoelectric feedback loop, Piezosystems Jena, Germany). Immersion oil (refractive index 1.515, type DF, Cargille Laboratories, USA) was used with immersion oil objective (63× magnification, numerical aperture 1.4). The photon count was recorded and analysed by an ALVL5000 multiple tau digital correlator (ALV-GmbH) in single channel mode. FCS data was analysed using non-linear, least-squares fitting with a single component diffusion model autocorrelation function corrected for the triplet state in Matlab® software. Diffusion time was used in the calculation of apparent hydrodynamic radius (Rh) and plotted as a function of assembly time. Rh calculations were based on the measured diffusion time for Alexa Fluor®-488 dye with the estimated Rh of the dye (=~0.7 nm in assembly buffer).

smFCS Assembly and Competition Assays

Initial measurements of Alexa Fluor®-488 fluorophore labelled RNA oligonucleotides were taken for at least 10 runs of 30 secs (5 min). Purified STNV CP was titrated into labelled RNA. Each titration was measured for a minimum of 10 30 secs runs. In assembly assays this was repeated until full capsid assembly had occurred. At this point RNase A was added to confirm RNA protection. In competition assays, once the sample had formed a capsomer structure (Rh=~5 nm) the sample was monitored for a further 120 runs of 10 secs (20 min to ensure stability). At this point unlabelled B3 short/B3 variant competitor was added in 100-fold molar excess and measured for 120 runs of 10 secs.

CD Analysis

Transcribed oligonucleotides were diluted to 1.5 µM in 300 µl, in a buffer containing 10 mM MES, 50 mM NaCl and 1 mM DTT at pH 6. Measurements were performed on a Jasco J715 spectropolarimeter, from 200 to 350 nm, with a bandwidth of 2 nm. Each Ca2+ and STNV titration was inverted 5 times and allowed to reach equilibria for 2 min prior to the next measurements. Thermal denaturations were performed using a Peltier temperature control from 10-95° C. in 5° C. steps, and an end scan was performed at 10° C. to check for cleavage. Each measurement was performed in triplicate and averaged. Data was converted to molar ellipticity using the equation: $\Delta\epsilon$ (cm2 mM-1)=$\theta$/(32980 C(mM) L(cm) N(no. of nt)).

Light Scattering Assay of Reassembly with Genomic RNA Variants

Figure 25A:
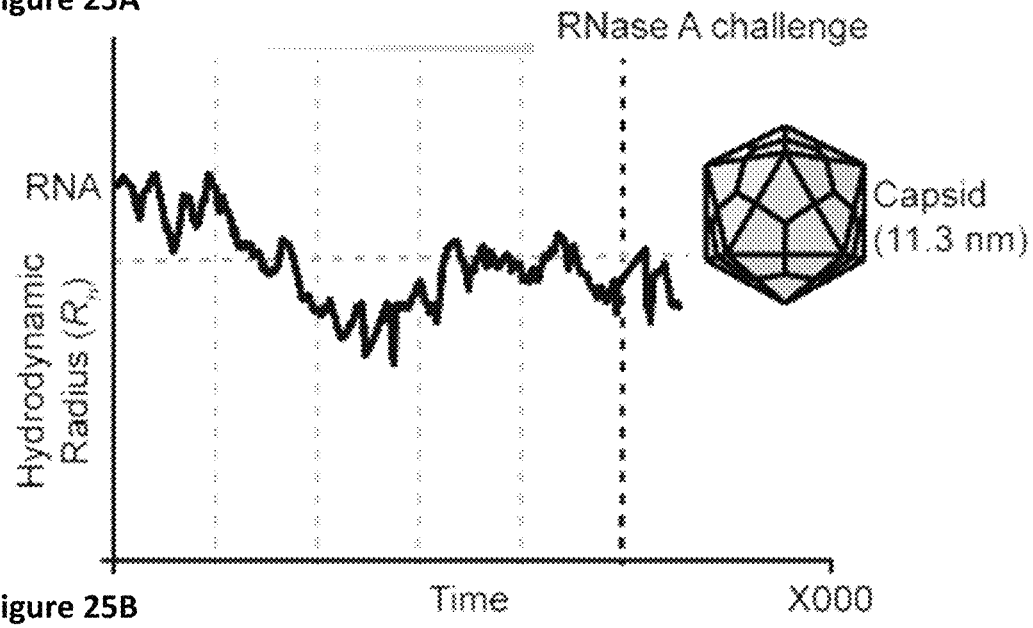
Figure 25B:
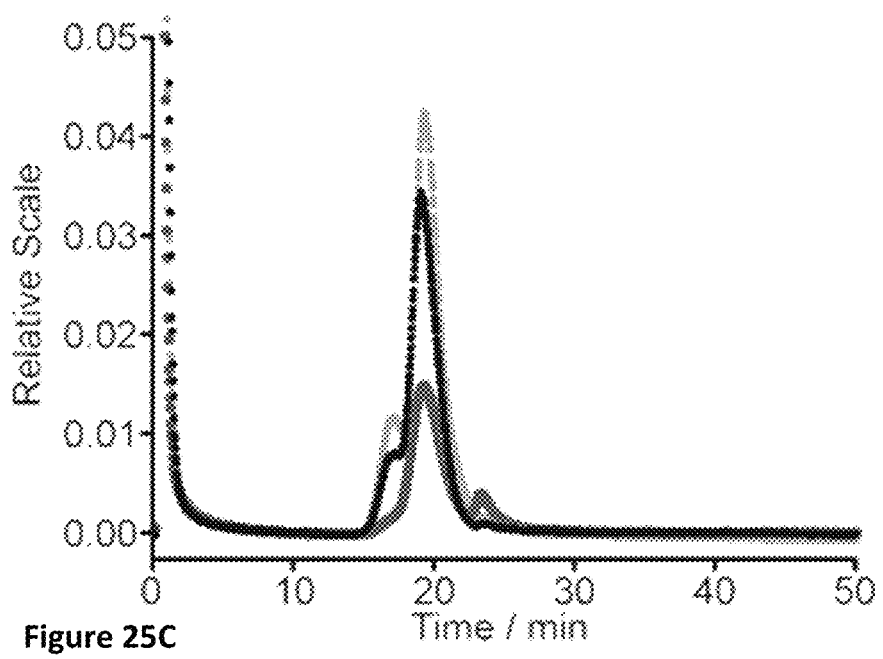
Figure 25C:
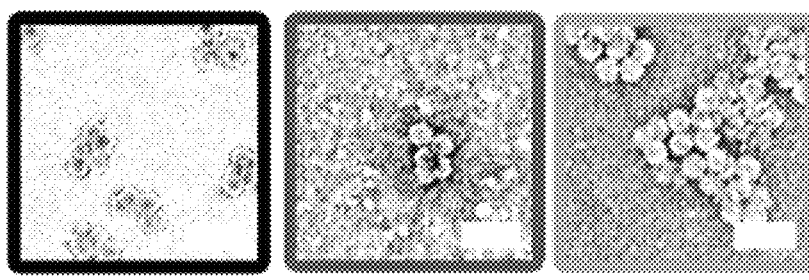

Reassemblies were performed with genomic chimeras in a 96 well plate as in the smFCS assays, with 1 nM genome and CP titrated in until a final concentration of 400 nM STNV CP was reached. This was concentrated through a 100 kDa Centricon® concentrator (Millipore) at 10k xg for 5 min and run on a TSKgel G6000PWxl SEC column (Tosoh) with an AKTA PURE® chromatography system (GE Healthcare) connected to a DAWN® multi-angle static light scattering detector, HELEOS® photometer, Optilab® TrEX refractometer for QELS and refractive index measurements. The column flow-rate was 0.4 ml min-1 for 50 min. Peaks were fractionated, A260/280 ratios measured and EM images obtained (FIG. 25). The yield of the Unstable PS3 sample, as calculated by integration of light scattering signal, is dramatically lower than that of the wild-type STNV RNA, whilst the stabilised synthetic cassette results in a significantly higher (>20%) yield in VLP compared to the natural sequence. QELS estimates the Rh values similar to those from smFCS, 9.3±0.1 nm, 9.1±0.3 nm and 8.9±0.2 nm for Synthetic, stabilised PS1-5+Δ1-127STNV-1, wild type STNV-1 and Unstable PS1-5+Δ1-127STNV-1, respectively (Table 6). The A260/280 ratios of the assembled VLPs eluting from the gel filtration column are also informative. Both the PS1-5+Δ1-127STNV-1 and the wild-type STNV-1 genome samples have identical values (1.62), whilst the Unstable PS1-5+Δ1-127STNV-1 sample has a higher value (1.89). This is consistent with there being a constant amount of RNA in the first two samples fully enclosed in shells containing the same number of CPs, whilst the final sample has the same RNA content in an incomplete shell.

EXAMPLE 1

The HBV pgRNA Contains Preferred Cp Binding Sites

HBV VLPs assembled from (full-length) Cp subunits expressed in *E. coli* were purified as described(3) (FIG. 7a & Table 1). They form a mixture of T=3 and predominantly T=4 shells. These were immobilised onto magnetic beads, disassembled by treatment with guanidinium chloride and then washed to remove host RNA, resulting in immobilised Cp dimers(20) with their ARDs accessible. RNA SELEX was carried out using our standard protocols (FIG. 7b) and the aptamer pool from the 10th round analysed by NextGen DNA sequencing (Methods).

The RNA sequences that bind Cp in the selected library were aligned to the HBV pre-genome most closely related to the protein used for the SELEX experiments (the laboratory strain, GenBank Seq id NC_003977.1 (21)). Statistically significant matches (a Bernoulli score of 12 or more, Methods) to the pgRNA of this strain (the blue peaks in FIG. 2a) were benchmarked against an alignment of the unselected library (grey curve in FIG. 2a) to identify peaks that occur with significant frequency. This identifies multiple sites dispersed across the pgRNA having similar sequences/structures to Cp binding aptamers, consistent with our expectation for PS-like sites across the genome. We applied the same procedure to 14 randomly selected HBV strain variants from GenBank, the current NCBI HBV reference strain (GenBank Seq ID NC_003977.2) as well as the laboratory strain (GenBank Seq ID NC_003977.1) and identified all those peaks that are conserved in at least 80% of these strains (marked with green crosses in FIG. 2a). These genomic regions are thus likely to encompass PSs. The three peaks with the highest conservation (100%) and peak heights, the latter indicating how many aptamers matched these sites, are labelled PS1, PS2 and PS3 in FIG. 2a. For the nine sites with high conservation between strains, we extracted 30 nts 5' and 3' to the peak nucleotide in the genomic sequences of three representative strain variants, including the laboratory strain and the reference genome, and considered all their possible secondary structure folds with negative free energy via Mfold (Methods). A similarity analysis of primary and secondary structure revealed the predicted existence of stem-loops sharing a purine-rich loop recognition motif, RGAG (FIG. 2b).

We computed the frequency of this motif in stem-loops across the 16 HBV strains analysed. Across all strains, the RGAG motif occurs in stem-loops on average ~25.4 times (precisely 25 times in the laboratory strain). Compared to 10,000 randomised versions of the pgRNAs, the frequency of occurrence of RGAG in the actual genome is 4.68 standard deviations above the average (FIG. 2c), strongly implying a functional role(s).

EXAMPLE 2 pgRNA Oligonucleotides Trigger VLP Formation In Vitro

PS1, 2 & 3 oligonucleotides (FIG. 8a), were tested for their ability to bind Cp dimers using single molecule fluorescence correlation spectroscopy (smFCS) (FIGS. 3 & 8b). This technique yields a real time estimate of the hydrodynamic radius ($R_h$) of dye-labelled species. Importantly, it allows reactions to be followed at low nanomolar concentrations, where we have shown that binding specificity more closely reflects the situation in vivo compared to most in vitro reactions. The latter are typically carried out at higher (e.g. 0.1-0.8 μM) concentrations(20), where the specificity of PS-mediated assembly is reduced or lost. In order to avoid electrostatic effects due to differing oligo lengths, each PS was produced as part of a 47 nt long fragment, each dye-labelled at its 5' end (Methods(19)). The labelled oligos (~15 nM) were then titrated with increasing amounts of Cp (5-250 nM Cp dimer) and the $R_h$ values tracked over time (FIG. 3a). After each addition there was a pause of ~10 min to allow reactions to equilibrate. The titrations lead to distortions in the data collection and the averaging, which is visible in the plots as noisy signals. After equilibration at 250 nM Cp, RNase was added to each reaction and the $R_h$ values monitored for ~10 min. If these declined steeply, it was assumed that the VLPs produced were incomplete. Negative stain EM images were obtained for the samples before RNase addition, and the sizes of the complexes present at this point were also assessed by calculation of $R_h$ distribution plots (FIG. 3b and FIG. 8c, respectively).

Each of the PS fragments stimulates assembly of both T=3 and T=4 complete VLPs with roughly equal efficiency under these conditions (FIGS. 3a & b), with the latter being the dominant product, as expected(22). Addition of Cp>250 nM does not increase the $R_h$ values obtained, implying that by this stage all the RNAs have been incorporated into VLPs. In order to assess whether these effects are a direct consequence of Cp-PS interaction, we carried out a number of controls. Dye-labelled PS fragments do not bind to preformed VLPs and remain RNase sensitive in their presence (Table 2), implying that the PSs only get internalised in assembling VLPs. To determine if the RNA triggers assembly, we compared assembly efficiency of Cp with and without PS RNA present by adding a protein modifying dye after incubation of Cp alone or completion of a titration of unlabelled PS1. The $R_h$ distribution plots are shown in FIG. 3b. In the absence of RNA, <5% of Cp assembles under these conditions, in contrast to >80% of the Cp for assembly in the presence of RNA. It appears that Cp-PS interaction triggers an increase in the assembly efficiency. This effect varies with the age of the Cp, consistent with oxidation of an assembly-inhibiting disulphide at the dimer interface(6). Comparative statements here are based on the results of both positive and negative control experiments with each batch of Cp.

We then probed the RNA sequence-specificity of these reactions (FIG. 9a). Test oligos comprised the epsilon stem-loop, as well as loop and bulge variants of PS1. This included a variant in which the bulge region was fully base-paired. In similar assays to the PS1-3 reactions the $R_h$ values for all three RNAs remain sensitive to nuclease action, implying that assembly of closed shells requires a specific RNA sequence/structure. EM images and distribution plots confirm this interpretation. The sequence sensitivity of the assembly reaction is further highlighted by additional PS1 variants (FIGS. 9b & c; Table 3). Their effects on assembly confirm the importance of the bulge and/or sequences within it, and the loop RGAG (here a GGAG) motif. A DNA oligonucleotide encompassing the PS1 sequence (FIG. 9d) elicits aggregation, showing that faithful assembly is a specific property of the PS in its RNA form, i.e. with an A helical duplex stem, as well as the Cp-recognition motif in the loop.

The C-terminal ARD of the HBV Cp is believed to mediate interactions with the pgRNA, and the 1-149 Cp fragment that lacks the ARD readily assembles in the absence of nucleic acid(23). We therefore assessed the ability of $Cp_{149}$ to respond to PSs in the smFCS assay. No RNA-dependent assembly, or PS binding by $Cp_{149}$, occurs under these conditions (FIG. 10a), although EM images show that the truncated Cp alone readily assembles, confirming that the ARD is essential for the interaction with RNA. The ARD is extensively phosphorylated in vivo, although the responsible cellular kinase remains unknown (24). Lowering the positive charge on the C-terminus of Cp should reduce its ability to bind PS RNAs. We phosphorylated Cp in vitro(8) (Table 1) and tested its properties. EM images show that modified Cp readily assembles but does not bind to PS1 in smFCS assays (FIG. 10b).

EXAMPLE 3

HBV NC Assembly is Triggered by Formation of a Sequence-Specific RNA-Core Protein Complex.

The VLPs assembled around PS1 were purified on a larger scale and their structures determined by cryo-EM, yielding icosahedrally-averaged reconstructions of the T=3 and T=4 particles (FIG. 4). A significant fraction (~25%) of the T=4 particles also contained an asymmetric feature located just below the protein shell. An asymmetric reconstruction of these particles was also calculated (FIG. 5). The result suggests the asymmetric feature represents a complex between PS1 oligonucleotides and the ARD domains of the overlying Cp subunits.

From the EM map at this resolution it is not possible to determine the number of PS oligonucleotides present in the complex. The $A_{260/280}$ ratio of the purified VLP suggests that the RNA content, assuming T=4 morphology, is ~5 oligos/particle(25). An additional estimate of this stoichiometry was obtained by studying photobleaching of PS1 VLPs (FIG. 4, Methods). VLPs show multiple bleaching steps, confirming that there are multiple oligos within each shell. Given the labelling efficiency of the oligos, the data are consistent with 2-4 oligos/VLP. We built a 3D model of PS1 and manually positioned it within the EM map (FIG. 4f, Methods). From the relative volume of the asymmetric density and the size of the PS1 oligo, it appears that at least two copies of the PS are present within the density. We cannot exclude the possibility that other RNA molecules are bound to the protein shell elsewhere, but are not visible due to mobility or an irregular location with respect to the ordered RNA density. The biochemical and structural data are consistent with the asymmetric structure being an assembly initiation complex, where an RNA preferred site(s) has initiated assembly culminating in the formation of the T=4 NC.

The cryo-EM data hint at a further insight into HBV biology. A minority of HBV particles, whether from assembly reactions or wild-type virus infections, assemble with T=3 quasi-symmetry and both types of particles are visible in our cryo-EM data. Using 2D and 3D classification the T=3 (~11%) and T=4 (89%) particles are readily separable. FIG. 4 shows 3D reconstructions of the two particles with imposed icosahedral symmetry at 5.6 Å and 4.7 Å resolution, respectively. In addition to the obvious differences in size and number of Cp dimers that the two VLP structures contain, the T=4 and T=3 maps are different in the features visible on their inner surfaces, where the ARDs are located and where RNA binding occurs. As might be expected for icosahedrally-averaged maps of a sub-stoichiometrically occupied VLP, both structures are essentially devoid of density attributable to RNA. The capsid shell of the T=4 structure is visibly thinner than the T=3 equivalent, however, and closer examination of the T=3 map suggests that additional density corresponding to ordered segments of the ARDs is visible (FIG. 4), which is absent in the T=4 structure (FIG. 4 c & d). This difference persists when the T=4 map is Fourier filtered to be at a similar resolution as the T=3 (FIG. 11). This is consistent with previous studies that showed that the Cp C-terminal region, including the ARD, plays a role(s) in determining capsid geometry(22, 26).

EXAMPLE 4

Sequence-Specific Recognition of Individual PS Sites

There are multiple consequences of sequence-specific RNA-CP recognition in the STNV system (FIG. 12). Titration of CP into oligonucleotides encompassing only PS3 (or B3) initially results in formation of a trimeric capsomer (Rh ~5 nm), followed by formation of T=1 VLPs (Rh~11.3 nm) as the CP concentration is raised gradually. Rh distribution plots of the smFCS data at the end of the titration suggest that the VLPs formed are homogeneous, whilst electron microscopy images (EM) and RNase challenge assays suggest that they are composed of complete protein shells. A similar titration with a PS3/B3 variant having a loop sequence of -U.U.U.U-, showed that CP binds such SLs, but the complex formed is unable to assemble to VLPs(19). The natural 127-mer, encompassing PSs1-5, shows more complex behaviour. Addition of low CP concentrations triggers a collapse in its $R_h$ by about 20-30%, mimicking the behaviour seen for the full length genome(27). Subsequent CP additions result in co-operative conversion to T=1 VLPs with the same properties as those formed around PS3 alone. PS sequence variants within this fragment confirm that -A.X.X.A- is a CP recognition motif and its presence is only absolutely required in PS3, however the variants no longer assemble with wild-type co-operativity(19). STNV-1 CP alone shows no tendency to aggregate below 15 µM under these conditions, and therefore everything in the titrations shown here is a consequence of RNA-CP binding.

These results highlight the importance of PS3 recognition by CP for assembly. In order to identify the critical features of that recognition, we produced a series of SLs encompassing variant loop sequences with the PS3 stem (FIG. 17 & Table 4). The variants have altered nucleotides in the "inner" two positions (-C.C-; -A.A-; -G.G-; -G.U- & -U.G-) compared to the wild-type -C.A- of PS3. "Outer" variants (-A.U.U.A-; -A.U.U.G-; -G.U.U.A-; -G.U.U.G-; -G.U.U.U-; -U.U.U.G-; -U.U.U.A- & -A.U.U.U-), in which both inner nucleotides were altered to uridines, were also tested. Our expectation was that there would be no base specificity at the middle positions while the adenines would be preferred at the first and last positions of the tetraloop. We examined their abilities to support assembly of both the T=1 shell and the trimeric capsomer. Test RNAs and CP were mixed at ~5 µM concentrations in reassembly buffer and the results assayed by velocity sedimentation analysis and in EM images. Under these conditions, the inner nucleotide variants form T=1 capsids with roughly similar efficiency as PS3, confirming that their identities are not part of the CP recognition motif (FIGS. 13 A/B & FIG. 17). The outer nucleotide variants showed differing behaviour, with only the -A.U.U.U-, -U.U.U.A- and -A.U.U.A- variants having a peak in a similar position to PS3, confirming that the outer adenines are part of the CP recognition motif.

In order to examine their relative importance for CP affinity, we adapted the smFCS assay (FIG. 13B). Labelled B3 was titrated with CP to form the trimer, as judged by the Rh value, and then a 100-fold molar excess of each sequence variant was added to compete off the B3. Variants that do not bind with a similar affinity to B3 fail to displace the labelled RNA, whereas B3 and other variants outcompete the labelled species restoring the Rh of CP-free RNA. The results (FIG. 13D) show the percentage Rh change following this challenge, revealing a wide variation in the ability of the variant RNAs to compete. All those with guanine substitutions, and the -A.U.U.U- variant, fail to compete. The superior performance of the -U.U.U.A- variant suggests that either the 3' A is the most important for CP recognition, or that the A-U base pair at the top of the adjacent stem breaks, presenting an -A.U.U.U.A.U- variant of the B3 motif that is still recognised by the CP. Either way, -A.X.X.A- outperforms all variants, suggesting that SLs carrying tetraloop motifs of -A.X.X.A- encompass the best CP recognition motif for assembly into VLPs.

EXAMPLE 5: THE ROLES OF ELECTROSTATICS AND PS COOPERATIVITY IN VLP ASSEMBLY

PS-mediated assembly explains features of viral genome packaging that purely electrostatically driven reactions do not, although there is clearly a beneficial effect of charge neutralisation in supplying some of the free energy to drive encapsidation. We therefore examined the importance of these effects on STNV assembly using a series of charge-change CP variants. Mutations at three positively charged residues R8, R14 and K17 in the N-terminal arm of the CP (FIG. 12), were produced with A or D in place of K or R. Since R14 and K17 are adjacent in three-dimensions, their variants were made as the double mutants, i.e. R14 Å/K17 Å and R14D/K17D. The mutated CPs express normally (FIG. 18), but both double mutants fail to assemble significantly in E. coli under these conditions. Since VLPs obtained from E. coli contain host cell RNA, as well as the recombinant mRNA encoding the viral CP, this outcome suggests that R14 and K17 play important roles in assembly.

Figure 20:
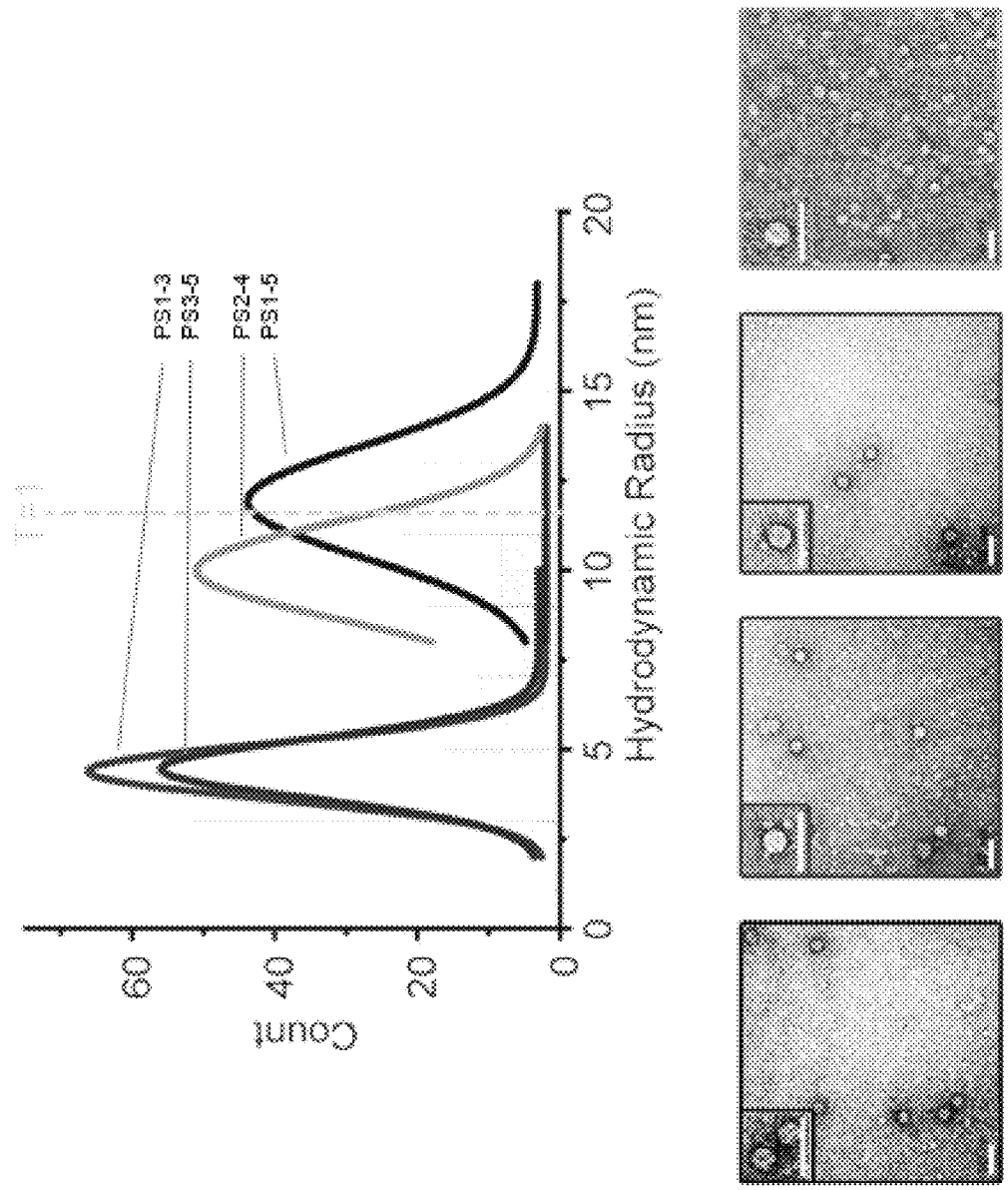
Figure 21:
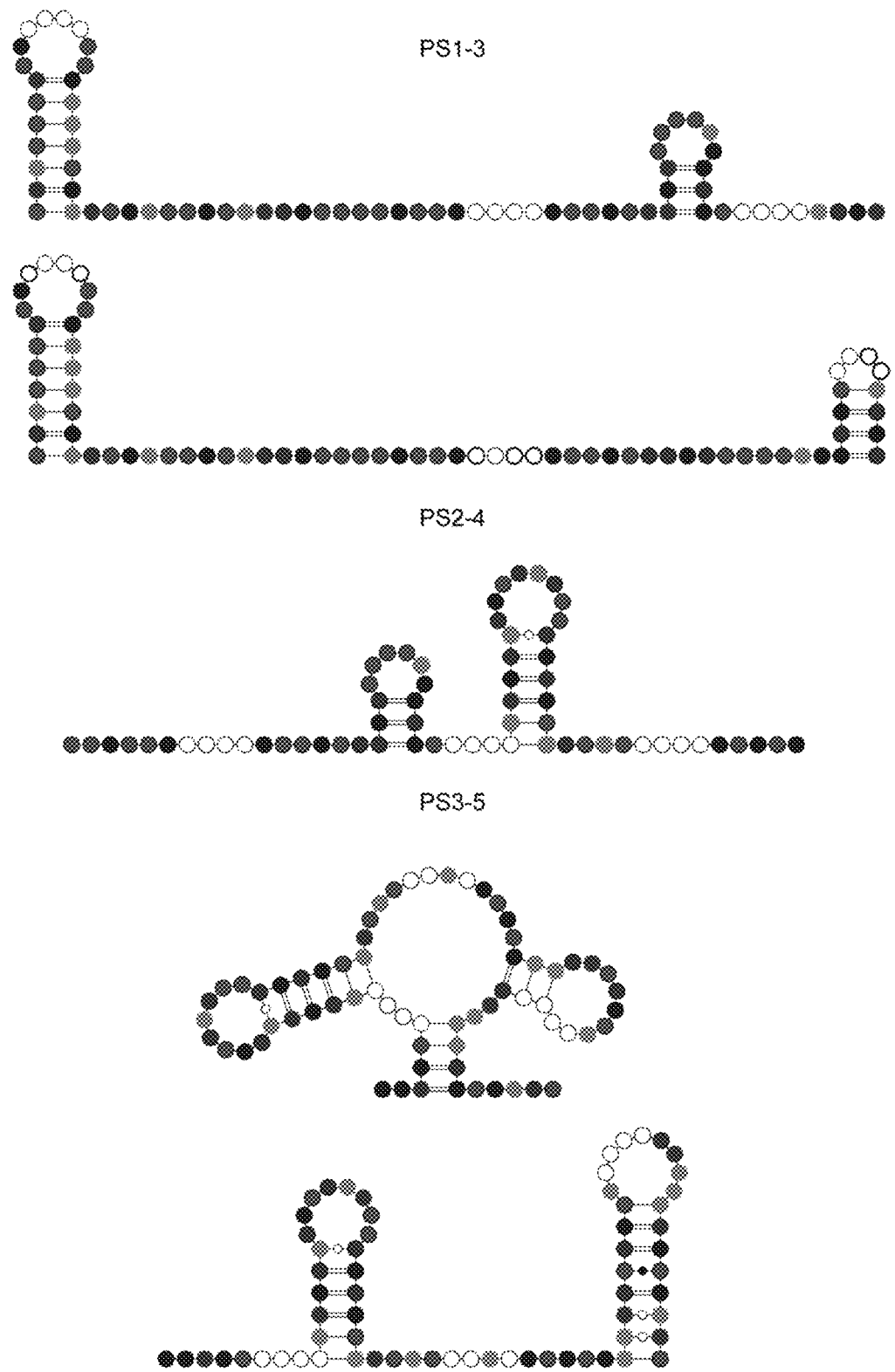

All the variant proteins were examined for their abilities to bind RNA oligos encompassing either a single PS (B3) or the 127-mer fragment (FIG. 14 & FIG. 19). Neither double mutant bound either RNA under these conditions. R8A assembles around B3 but requires a much higher (>10 fold) CP concentration to do so, consistent with it having a lowered affinity for the RNA. By 1 μM CP it forms T=1 shells that are resistant to RNase challenge. The R8D variant confirms the importance of the positive charge, failing to form any stable higher order species, even at higher concentrations, with the RNA remaining accessible to RNase digestion. This dependence on favourable electrostatic interaction remains when R8D is titrated against the 127-mer (FIG. 14A). However, with this RNA both R8A and wild-type CP show very similar binding curves, including the initial Rh decrease. It appears that the co-operativity arising from CP binding at multiple PS sites overcomes the deleterious effect on intrinsic RNA-CP affinity of reduced electrostatic attraction. If we assume that the altered charge(s) on the N-terminal arm does not significantly alter the unliganded CP conformation, these effects probe the role(s) of electrostatic interactions during RNA sequence-specific triggering of assembly. They imply that charge neutralisation is not an absolute requirement for assembly on longer natural RNA fragments, consistent with the PS-mediated, but not the electrostatic assembly mechanism. Given that the cooperativity of multiple RNA PSs can overcome diminution of electrostatic attraction, as expected for a process in which PSs act collectively, we then examined how many PSs are required to generate cooperative assembly. Given the importance of recognition at PS3 and the effects seen for fragments containing five PSs, three sub-fragments of the 127-mer each containing PS3 were tested (FIG. 14B & FIG. 20). These are PS1-PS3 (nts 1-76); PS2-PS4 (nts 38-104) and PS3-PS5 (nts 66-127), each potentially able to bind CP at PS3 but differing in the numbers of flanking sites, from two 5' or 3' of PS3, to just one on each flank. Only the fragment with the PS3 centrally located assembles T=1 shells that are RNase resistant, although it does not show a collapse and the overall yield is lower than for the 127-mer. The other fragments appear to form non-specific aggregates that eventually spontaneously dissociate.

The interpretation of these results is non-trivial. The effects are clearly not purely electrostatic in nature since the PS2-4 fragment (66 nts) is shorter than PS1-3 (76 nts) and 1 nt shorter than PS3-5. To understand the specificity of the reactions we need to consider the folding propensity of each of the PS-encompassing sites. The secondary structure of the 127-mer shown (FIG. 15) was arrived at by constraining its folds to capture the maximum number of SLs with -A.X.X.A- loop motifs present. In this fragment only PS1 and PS3 are predicted to have a favourable folding free energy (Mfold,(10). in isolation. This is consistent with our previous smFCS assays, in which alterations of the CP recognition motifs within each PS and variations in the relative spacing of PS3 with its neighbours resulted in markedly different assembly behaviour(28). We expect these RNA molecules to exist in solution as an ensemble of differing conformations. Interaction with the STNV CP will displace this equilibrium, preferentially selecting a single or few assembly competent conformations in which the PSs are present. The assembly efficiency we see may therefore be directly related to the population of such conformers in the ensemble and thus related to the free energy costs in imposing this conformation. Assessing the extent of a conformational ensemble is difficult, but a sense of the likelihood of alternate structures can be obtained from Mfold by altering the usual default parameters to explore an ensemble of suboptimal folds within 500 percent from the minimum free energy fold (suboptimality=500).

When such structures are examined for the three PS-containing fragments, a possible explanation for their assembly competencies emerges. For PS1-3, the dominant folds encompass PS1 with a minority also containing PS3 (Table 5). In principle, that minor conformer could promote assembly, but the critical spacing between PS1 and PS3 is too large to facilitate the co-operative effects of multiple PSs. A similar analysis of PS2-4 suggests that the dominant secondary structure does not contain any of the PS folds expected for the 127-mer. However, its predicted secondary structure contains two alternative SLs that are almost always present, one of which presents an -A.X.X.A- sequence (FIG. 22). Their relative spacing (4 nt) is short enough to see a co-operative effect. The PS3-5 fragment forms two SLs within 10-12 nts of one another, one presenting an -A.X.X.A- motif as PS5. This would suggest an assembly-competent structure. However, in the ensemble of possible structures, this SL is only present in 6% of the potential folds (Table 5), which may account for the assembly behaviour (FIG. 14B).

The conformational scrambling behaviour described above for the fragments encompassing three PSs probably reflects events in vivo where it is known that sequences within the 127-mer participate in formation of a translational enhancer with sequences in the 3' UTR(29). That complex cannot be present in the assembly competent conformer. In order to explore the effects of such secondary structure folding propensity further, we turned to the design of artificial PS-containing sequences.

EXAMPLE 6: ASSEMBLY OF NON-VIRAL SUBSTRATES

Figure 23A:
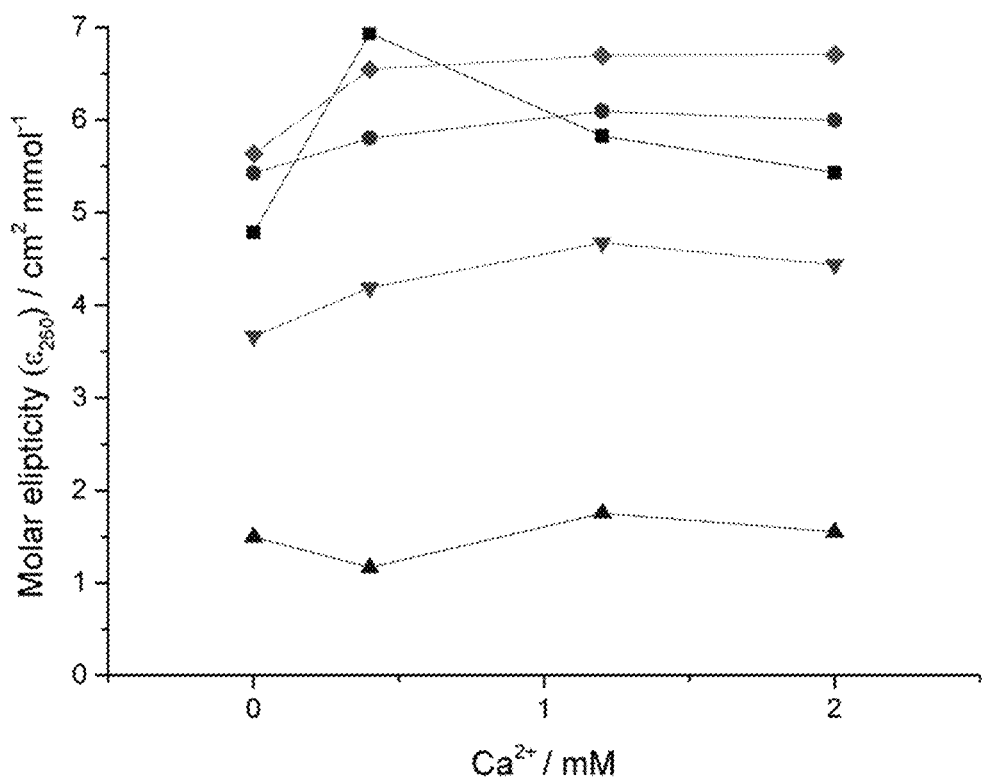
Figure 23B:
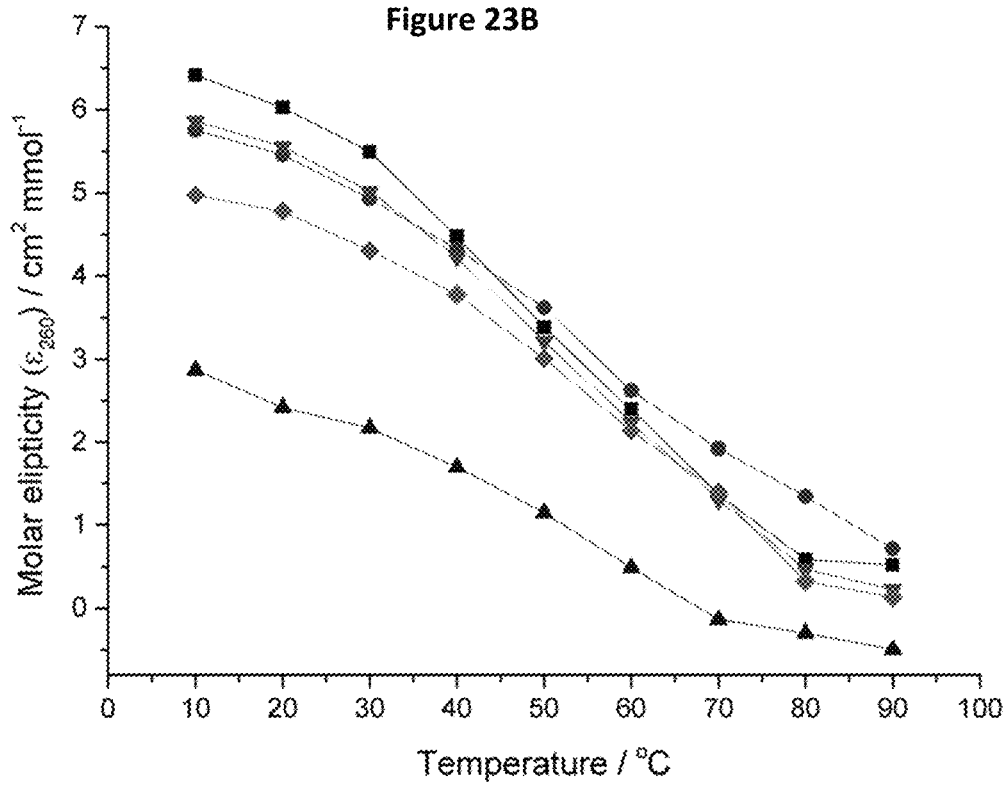

In order to investigate the requirements for an efficient assembly substrate, we produced synthetic cassettes mimicking aspects of the wild-type 127 mer (PS1-5) in which most of the natural viral sequence has been replaced (~77%). Attempts to create these sequences using a simple base substitution scheme, e.g. swapping all As for Us; Cs for Gs, Gs for Cs and Us for As in the regions other than the CP recognition motifs, all resulted in unstable secondary structures. We therefore chose to modify the existing SLs by conversion of base pairs to G-C, inversion of existing G-C pairs, or adding extra base pairs and then checking that they would likely fold into similar secondary structures to those in the wild-type 127-mer. The natural viral sequences connecting these SLs were then replaced with strings of As and Gs until only one fold was most likely (FIG. 18 & FIG. 23). The relative separations of the base-paired stems were kept identical to those in the wild-type 127-mer. As a result of these changes, PSs 1, 2, 4, and 5 have been stabilised compared to the wild-type 127mer, with all SLs having favourable folding propensity (FIG. 23).

To assess the importance of the folding propensity of the dominant PS3 site we also created the following synthetic versions: 1) Unstable PS1-5, in which the folding free energy of PS3, the central PS, is positive (0.3 vs −2.6 kcal/mol), i.e. a scenario in which PS3 is unlikely to fold spontaneously; 2) Stable PS1-5, in which the folding free energy of the central PS is more negative (−3.5 vs −2.6 kcal/mol for the 127-mer), i.e. where PS3 is more stable; 3) AII PS3, in which all five PSs mimick PS3, with stems of all PSs extended to the same length (7 bp) and all CP recognition motifs identical to that in wild-type PS3; & 4) Synthetic, stabilised PS1-5, containing the artificial PSs 1, 2, 4 and 5 from Stable PS1-5, and the artificial extended stem-loop for PS3 from the AII PS3 construct. The latter is hyper-stabilised with respect to the PS3 in both the wild-type 127-mer and the Stable PS1-5 (−7.6 vs −2.6 or −3.5 kcal/mol, respectively).

EXAMPLE 7

Figure 24A:
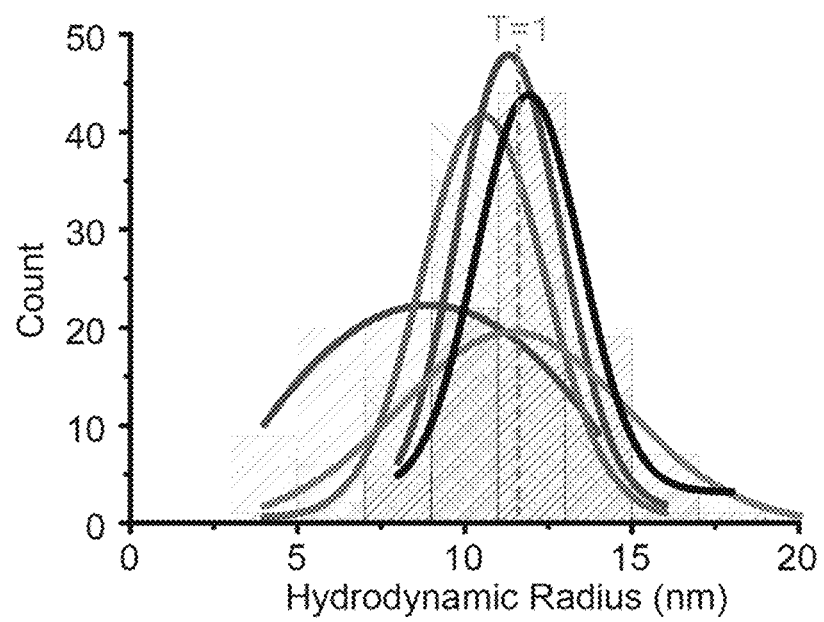
Figure 24B:
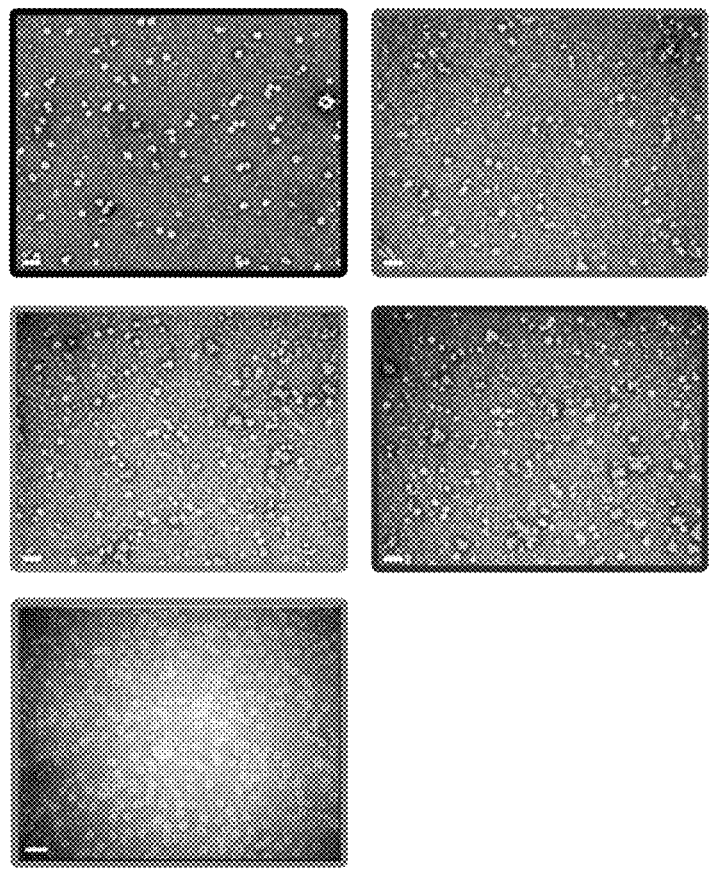

In order to compare the behaviours of these test variant oligonucleotides we examined their potential secondary structures. Table 5 lists the frequency of occurrence of each PS in ensembles created using the suboptimality feature in Mfold, together with their relative spacings. In addition, we compared their circular dichroism (CD) spectra. CD provides a physical signal(30), the molar ellipticity at 260 nm, that is proportional to the percentage of base-paired residues and/or tertiary structure. The measurements were made in a buffer containing calcium ions since these are required in the reassembly buffer, there being several Ca2+ binding sites within the STNV capsid (38, 39). Titration of the test RNAs up to 2 mM calcium, the concentration in reassembly buffers, results in mild increases (9-17%) in the 260 nm ellipticity, as expected (FIG. 24A). The only exception is Unstable PS1-5, which does not respond to the presence of the cation. The molar ellipticity values of all test RNAs in this buffer decline as expected with temperature (FIG. 24B). All the RNAs have different CD ellipticities at 260 nm, illustrating the complexity of comparing RNA conformational ensembles. The Unstable PS1-5 sample is much less structured throughout the temperature range. Perhaps surprisingly given the apparent Mfold structures, the wild-type 127-mer has the highest amount of structure at the lower temperatures. At the highest temperature tested all the RNAs except Unstable PS1-5 have roughly similar ellipticity values, implying that they had reached similar levels of denaturation.

All these synthetic variants trigger assembly of T=1 capsids and are able to protect the encapsidated RNA from challenge by nuclease but with very different CP concentration dependences. All but the Unstable PS1-5 show similar initial decreases in Rh to the 127-mer (FIG. 15B). The Unstable PS1-5 assembly behaviour resembles that of PS3 alone, suggesting that it has lost co-operativity, and its distribution plot and appearance in EM images (FIG. 24) suggests that it has also lost the ability to regulate capsid formation efficiently. In contrast, the importance of the central PS folding propensity is illustrated by the behaviour of Stable PS1-5. Despite the potential issues with a folding ensemble, it shows a similar collapse to the 127-mer and a cooperative assembly to T=1 particles with a similar Rh distribution to the wild-type fragment. It assembles into VLPs at lower CP concentrations than the wild-type 127-mer, i.e. under these conditions it is a better assembly substrate. Remarkably, AII PS3 also assembles more efficiently than wild-type even though it encompasses PSs that are longer than those found in the 127-mer, suggesting that there is some leeway in the PS secondary structure context in which the recognition motif is presented. This is a little surprising given the critical dependency on PS spacing around PS3 observed previously(19). The efficiency of assembly and the folding propensity of the AII PS3 variant notwithstanding, the Synthetic, stabilised PS1-5 is by far the best assembly substrate, assembling to VLPs most efficiently (i.e. it assembles more quickly following 100 nM CP titration point) (FIG. 15B).

EXAMPLE 8

These results suggest that it is possible to abstract the critical assembly features from a viral genomic RNA fragment. Given the alterations in the stem lengths and loop sizes in the synthetic fragments it would also appear that there is considerable scope for engineering templates with improved PS folding propensity.

Transfer of Critical Assembly Features to Genomic-Scale RNAs

As a test of whether these experiments have successfully identified essential assembly features we examined how inclusion of this improved RNA "cassette" alters the assembly efficiency of a natural RNA. That RNA must be inherently able to be assembled into the small volume of the STNV virion. The genomic fragment from 128-1239 nts of the STNV-1 RNA is the obvious test fragment. We therefore constructed two genomic chimeras: [Unstable PS1-5+Δ1-127STNV-1], which is 1242 nts long and [Synthetic, stabilised PS1-5+Δ1-127STNV-1], 1248 nts long, and compared their assembly efficiencies in vitro relative to the wild-type STNV-1 RNA (FIG. 16A). All three behaved differently in these assays, implying that the sequence and structure of the 5' 127-mers regulates the assembly pathway of a fragment that is over 10 times its size. The wild-type genome shows the expected initial collapse in Rh (to ~7.5 nm) followed by a slight rise in Rh consistent with the formation of T=1 particles (FIG. 16B). Note, the data in FIG. 16A are for a CP titration compared to the single step addition of a complete complement of CPs described previously (12). In contrast, the Unstable PS1-5 leader sequence results in a larger initial collapse in Rh (to ~5 nm; 65%) followed by only a small rise that implies VLPs are not made efficiently. Indeed the RNA in this species remains susceptible to RNase degradation, implying that it has not been completely encapsidated. Synthetic, stabilised PS1-5+Δ1-127STNV-1 has roughly the same initial, CP-free Rh, but appears simply to shrink to values consistent with VLP formation, rather than collapsing and recovering. Rh distributions and EM images of the assembly products are consistent with this interpretation. It is noticeable that the Synthetic, stabilised PS1-5+Δ1-127STNV-1 VLP trace is less noisy than the other samples and has a distribution in Rh sizes that more closely matches that of authentic VLPs isolated from *E. coli*. Confirmation of the interpretation of these results is provided by quasi-elastic light scattering (QELS) of the products following elution from a gel filtration column (FIG. 25).

EXAMPLE 9

We have shown that the dual code inherent in RNA PS-mediated virus assembly, i.e. that genomic RNAs simultaneously encode a genetic message as well as instructions for efficient capsid assembly, are separable. An important question is why do the codes not separate during the course of viral evolution, especially as replication in ssRNA viruses occurs via error-prone processes that lead to creation of a quasi-species of genome variants. There are now three examples of viruses using RNA PS-mediated virus assembly where we have structural information that partially answer this question. In bacteriophage MS2(31), human parechovirus-1(32) and STNV(19), at least one of the PS sites in the genome also encodes amino acid residues forming part of the PS binding site. This intimate embedding of both codes has the consequence of favouring assembly only of progeny RNAs in which PS-mediated assembly persists. Similarly the density of functions encoded within such RNAs is well known. The natural 5' 127-mer in the STNV genome also forms an essential transcriptional/translational enhancer contact with the 3' end sequence. Since that structure and assembly are mutually excluding functions, the natural sequence has evolved to balance the propensity that they form such that the viral lifecycle can proceed efficiently.

The focus here is the property of the assembly code liberated from the wild-type viral RNA sequence. Indeed, by sequentially investigating each aspect of the STNV assembly sequence in its natural context we have been able to reproduce its effects in triggering in vitro assembly of STNV CPs using a synthetic non-viral RNA. Additional refinements allow us to produce sequences that are either less or more efficient than the wild-type STNV 127-mer. These results confirm the nature of PS-mediated assembly for STNV. Assembly in vitro initiates within the 127-mer by recognition by CP subunits of the PS3 stem-loop. Higher-order CP binding is dependent on the correct positioning and folding of the neighbouring PSs (PS2 and 4), each presenting a consensus CP recognition motif in the loop. The 127-mer potentially encompasses five PSs that make the initial binding co-operative with respect to protein concentration leading to a collapse in the hydrodynamic radius of the RNA, a necessary precursor to encapsidation. Electrostatic interactions contribute to these protein-RNA contacts but are not the major driving force, which instead is a high-affinity sequence-specific interaction of the stem and loop regions of the PSs with the inner surface of the protein capsid. Despite its minimal sequence content, the -A.U.U.A-sequence is bound with low nanomolar affinity by the CP. Remarkably, grafting the synthetic variant 127-mers onto the remainder of the natural STNV-1 genome results in chimeras whose assembly properties are dominated by the first ~10% of the RNA.

Previously, Wilson and colleagues showed they could direct assembly of non-viral RNAs into rods of Tobacco Mosaic Virus (TMV) CP by creating RNA chimeras encompassing the TMV assembly initiation site(33, 34). This was successful, with the length of the protein-coated rods formed being determined by the length of the RNA being packaged, as expected from the known assembly mechanism(35). This approach was less successful when applied to spherical ssRNA viruses(36), the highest affinity MS2 PS having positive effects on in vitro encapsidation of short RNAs but being less important on longer ones(37). Note, all these experiments were done at micromolar concentrations where the effects of PS-mediated assembly are lost(31, 37). The results described above suggest an efficient route for encapsidation of bespoke, non-viral RNAs in shells of viral CPs. In vitro assembly may be possible for a large number of CP-RNA combinations, but it differs from in vivo assembly where, in many viruses, there is good evidence suggesting that only nascent genomic transcripts emerging from the viral polymerase complex are packaged into progeny virions. In such reactions, the RNA is very likely to fold kinetically, avoiding some of the issues with RNA conformational ensembles in the in vitro reactions such as those described here.

Viruses and virus-like particles are finding increasing potential medical applications as gene therapy or drug-delivery vectors, as well as acting as non-replicating synthetic vaccines. Viral protein shells are also of interest for nanotechnology applications. The results described here offer an important insight into ways to create such structures with high efficiency and potentially carrying non-viral RNAs with advantageous properties. This will be essential for the production of designer synthetic virions.

REFERENCES

1. Yu X, Jin L, Jih J, Shih C, Zhou Z H (2013) 3.5 Å cryoEM structure of hepatitis B virus core assembled from full-length core protein. *PLOS ONE* 8(9):e69729.
2. Darty K, Denise A, Ponty Y (2009) VARNA: Interactive drawing and editing of the RNA secondary structure. *Bioinformatics* 25(15):1974-1975.
3. Porterfield J Z, et al. (2010) Full-length hepatitis B virus core protein packages viral and heterologous RNA with similarly high levels of cooperativity. *J Virol* 84(14): 7174-7184.
4. Lakowicz J R ed. (2006) *Principles of Fluorescence Spectroscopy* (Springer US, Boston, MA).
5. Holmes K, et al. (2015) Assembly Pathway of Hepatitis B Core Virus-like Particles from Genetically Fused Dimers. *Journal of Biological Chemistry* 290(26):16238-16245.
6. Selzer L, Katen S P, Zlotnick A (2014) The hepatitis B virus core protein intradimer interface modulates capsid assembly and stability. *Biochemistry* 53(34):5496-5504.
7. A Zlotnick, et al. (1996) Dimorphism of Hepatitis B Virus Capsids Is Strongly Influenced by the C-Terminus of the Capsid Protein. *Biochemistry* 35(23):7412-7421.
8. Aubol B E, et al. (2003) Processive phosphorylation of alternative splicing factor/splicing factor 2. *Proceedings of the National Academy of Sciences* 100(22):12601-12606.
9. Bunka D H J, et al. (2011) Degenerate RNA packaging signals in the genome of Satellite Tobacco Necrosis Virus: implications for the assembly of a T=1 capsid. *J Mol Biol* 413(1):51-65.
10. Zuker M (2003) Mfold web server for nucleic acid folding and hybridization prediction. *Nucleic Acids Res* 31(13):3406-3415.
11. Podjarny A, Dejaegere A P, Kieffer B eds. (2011) *Biophysical Approaches Determining Ligand Binding to Biomolecular Targets: Detection, Measurement and Modelling* (Royal Society of Chemistry, Cambridge) Available at: http://ebook.rsc.org/?DOI=10.1039/9781849732666.
12. Sharma A, et al. (2014) Domain movements of the enhancer-dependent sigma factor drive DNA delivery into the RNA polymerase active site: insights from single molecule studies. *Nucleic Acids Res* 42(8):5177-5190.
13. Li X, et al. (2013) Electron counting and beam-induced motion correction enable near-atomic-resolution single-particle cryo-EM. *Nature Methods* 10(6):584-590.
14. Rohou A, Grigorieff N (2015) CTFFIND4: Fast and accurate defocus estimation from electron micrographs. *Journal of structural biology* 192(2):216-221.

15. Scheres S H W (2015) Semi-automated selection of cryo-EM particles in RELION-1.3. *Journal of structural biology* 189(2):114-122.
16. Popenda M, et al. (2012) Automated 3D structure composition for large RNAs. *Nucleic Acids Res* 40(14): e112-e112.
17. Pettersen E F, et al. (2004) UCSF Chimera—A visualization system for exploratory research and analysis. *Journal of computational chemistry* 25(13):1605-1612.
18. Lane S W, et al. (2011) Construction and crystal structure of recombinant STNV capsids. *J Mol Biol* 413(1):41-50.
19. Patel N, et al. (2015) Revealing the density of encoded functions in a viral RNA. *Proc Natl Acad Sci USA* 112(7):2227-2232.
20. Porterfield J Z, et al. (2010) Full-length hepatitis B virus core protein packages viral and heterologous RNA with similarly high levels of cooperativity. *J Virol* 84(14): 7174-7184.
21. Wang J C-Y, Nickens D G, Lentz T B, Loeb D D, Zlotnick A (2014) Encapsidated hepatitis B virus reverse transcriptase is poised on an ordered RNA lattice. *Proc Natl Acad Sci USA* 111(31):11329-11334.
22. A Zlotnick, et al. (1996) Dimorphism of Hepatitis B Virus Capsids Is Strongly Influenced by the C-Terminus of the Capsid Protein. *Biochemistry* 35(23):7412-7421.
23. Birnbaum F, Nassal M (1990) Hepatitis B virus nucleocapsid assembly: primary structure requirements in the core protein. *J Virol* 64(7):3319-3330.
24. Ludgate L, et al. (2012) Cyclin-dependent kinase 2 phosphorylates s/t-p sites in the hepadnavirus core protein C-terminal domain and is incorporated into viral capsids. *J Virol* 86(22):12237-12250.
25. Porterfield J Z, Zlotnick A (2010) A simple and general method for determining the protein and nucleic acid content of viruses by UV absorbance. *Virology* 407(2): 281-288.
26. Watts N R, et al. (2002) The morphogenic linker peptide of HBV capsid protein forms a mobile array on the interior surface. *EMBO Journal* 21(5):876-884.
27. Borodavka A, Tuma R, Stockley P G (2012) Evidence that viral RNAs have evolved for efficient, two-stage packaging. *Proc Natl Acad Sci USA* 109(39):15769-15774.
28. Dykeman E C, Stockley P G, Twarock R (2014) Solving a Levinthal's paradox for virus assembly identifies a unique antiviral strategy. *Proc Natl Acad Sci USA* 111(14):5361-5366.
29. Kaempfer R, van Emmelo J, Fiers W (1981) Specific binding of eukaryotic initiation factor 2 to satellite tobacco necrosis virus RNA at a 5'-terminal sequence comprising the ribosome binding site. *Proceedings of the National Academy of Sciences* 78(3):1542-1546.
30. Sosnick T R, Fang X, Shelton V M (2000) Application of circular dichroism to study RNA folding transitions. *Meth Enzymol* 317:393-409.
31. Beckett D, Uhlenbeck O C (1988) Ribonucleoprotein complexes of R17 coat protein and a translational operator analog. *J Mol Biol* 204(4):927-938.
32. Shakeel S, et al. (2017) Genomic RNA folding mediates assembly of human parechovirus. *Nat Commun* 8(1):5.
33. Sleat D E, Turner P C, Finch J T, Butler P J, Wilson T M (1986) Packaging of recombinant RNA molecules into pseudovirus particles directed by the origin-of-assembly sequence from tobacco mosaic virus RNA. *Virology* 155(2):299-308.
34. Gallie D R, Plaskitt K A, Wilson T M (1987) The effect of multiple dispersed copies of the origin-of-assembly sequence from TMV RNA on the morphology of pseudovirus particles assembled in vitro. *Virology* 158(2): 473-476.
35. Caspar D L, Klug A (1962) Physical principles in the construction of regular viruses. *Cold Spring Harb Symp Quant Biol* 27:1-24.
36. Qu F, Morris T J (1997) Encapsidation of turnip crinkle virus is defined by a specific packaging signal and RNA size. *J Virol* 71(2):1428-1435.
37. Beckett D, Wu H N, Uhlenbeck O C (1988) Roles of operator and non-operator RNA sequences in bacteriophage R17 capsid assembly. *J Mol Biol* 204(4):939-947.

The invention claimed is:

1. An immunogenic composition comprising:
   an adjuvant; and
   a virus like particle (VLP) comprising an artificial RNA cassette, wherein the artificial RNA cassette comprises:
   one or more packaging signals arranged in series and separated by a non-coding viral nucleic acid, said one or more packaging signals comprising a nucleic acid loop domain comprising a nucleotide binding motif for cognate viral capsid protein(s), and a nucleic acid stem domain comprising a double stranded region by intramolecular base pairing,
   wherein:
   a) said VLP is a Hepatitis B virus VLP, said one or more packaging signals is from Hepatitis B virus, and said nucleotide binding motif comprises the nucleotide sequence RGAG, wherein R is G or A; or
   b) said VLP is a Satellite Tobacco Necrosis Virus VLP, said one or more packaging signals is from Satellite Tobacco Necrosis Virus, and said nucleotide binding motif comprises the nucleotide sequence AXXA or AXXXA, wherein X is any nucleotide base; and
   wherein said artificial RNA cassette, when contacted with a plurality of cognate viral capsid proteins, assembles said cognate viral capsid proteins into a VLP that protects said packaging signals contained within said VLP from ribonuclease digestion.

2. The immunogenic composition according to claim 1, wherein said artificial RNA cassette is non-replicating.

3. The immunogenic composition according to claim 1, wherein said VLP provokes an immune response similar to an immune response of a native virus particle when administered to an animal subject.

4. The immunogenic composition of claim 1, wherein said artificial RNA cassette does not comprise a protein-encoding nucleic acid.

5. The immunogenic composition according to claim 1, wherein said artificial RNA cassette comprises at least 2, at least 3, at least 4 or at least 5 packaging signals.

6. The immunogenic composition according to claim 1, wherein said non-coding viral nucleic acid separating said one or more packaging signals is at least 5 nucleotides in length.

7. The immunogenic composition according to claim 1, wherein
   said nucleic acid loop domain is at least 4 nucleotides in length;
   said nucleic acid stem domain is at least 5 base pairs (bp) in length;
   said artificial RNA cassette is at least 50 nucleotides in length; and/or
   said artificial RNA cassette is between 50 and 1000 nucleotides in length.

8. The immunogenic composition according to claim 1, wherein said artificial RNA cassette comprises at least one, two or three packaging signals from Hepatitis B virus, wherein one or more of said at least one, two or three packaging signals from Hepatitis B includes the nucleotide binding motif RGAG.

9. The immunogenic composition according to claim 1, wherein said artificial RNA cassette comprises at least one Hepatitis B packaging signal, wherein each of said Hepatitis B packaging signals includes the binding motif RGAG.

10. The immunogenic composition according to claim 1, wherein said artificial RNA cassette comprises:

i) a nucleic acid molecule comprising the nucleotide sequence GUUUGUUUAAAGACUGGGAG-GAGUUGGGGGAGGAG, as set forth by SEQ ID NO: 1;
ii) a nucleic acid molecule comprising at least 25% sequence identity to the nucleotide sequence of SEQ ID NO: 1 and comprising the nucleotide binding motif GGGAG;
iii) a nucleic acid molecule comprising the nucleotide sequence GGGCCCU-CUGACAGUUAAUGAAAAAGGAGAUUAAAA UUAAUUAUG CCU, as set forth by SEQ ID NO: 2;
iv) a nucleic acid molecule comprising at least 25% sequence identity to the nucleotide sequence of SEQ ID NO: 2 and comprising the nucleotide binding motif GAAAAAGGAG;
v) a nucleic acid molecule comprising the nucleotide sequence GGCUGGCAUUC-UAUAUAAGAGAGAAACUACACGC, as set forth by SEQ ID NO: 3;
vi) a nucleic acid molecule comprising at least 25% sequence identity to the nucleotide sequence of SEQ ID NO: 3 and comprising the nucleotide binding motif AUAUAAGAG;
vii) a nucleic acid molecule comprising SEQ ID NO: 1;
viii) a nucleic acid molecule comprising SEQ ID NO: 2;
ix) a nucleic acid molecule comprising SEQ ID NO: 3; or
x) a nucleic acid molecule comprising SEQ ID NO: 4.

11. The immunogenic composition according to claim 1, wherein said artificial RNA cassette comprises a nucleotide sequence selected from the group consisting of:
i) a nucleic acid molecule comprising the nucleotide sequence of SEQ ID NO: 5;
ii) a nucleic acid molecule comprising a nucleotide sequence comprising at least 25% sequence identify to the nucleotide sequence of SEQ ID NO: 5 and comprising the nucleotide binding motif AXXA;
iii) a nucleic acid molecule comprising the nucleotide sequence of SEQ ID NO: 6;
iv) a nucleic acid molecule comprising at least 25% sequence identity to the nucleotide sequence of SEQ ID NO: 6 and comprising the nucleotide binding motif AXXA;
v) a nucleic acid molecule comprising the nucleotide sequence of SEQ ID NO: 7;
vi) a nucleic acid molecule comprising at least 25% sequence identity to the nucleotide sequence of SEQ ID NO: 7 and comprising the nucleotide binding motif AXXA;
vii) a nucleic acid molecule comprising the nucleotide sequence of SEQ ID NO: 8; and
viii) a nucleic acid molecule comprising at least 25% sequence identity to the nucleotide sequence of SEQ ID NO: 8 and comprising the nucleotide binding motif AXXA.

12. The immunogenic composition according to claim 1, wherein said artificial RNA cassette further comprises a transcription cassette comprising a nucleic acid molecule adapted to transcribe a nucleic acid encoding a polypeptide or a functional RNA.

13. The immunogenic composition according to claim 12 wherein said transcription cassette comprises a promoter sequence and termination sequence to enable expression of said nucleic acid molecule encoding said polypeptide or functional RNA.

14. The immunogenic composition according to claim 13, wherein said polypeptide is a therapeutic polypeptide.

15. The immunogenic composition according to claim 13, wherein said functional RNA is an mRNA encoding a therapeutic polypeptide, an antisense oligonucleotide or an siRNA.

16. A method of stimulating an immune response in a subject, comprising administering an effective amount of the immunogenic composition of claim 1 to the subject, thereby stimulating an immune response.

17. The method of claim 16, wherein
the immune response is induction of an antibody response wherein said antibody response induces antibodies that specifically bind native virus particles; and/or
said virus like particle retains or has enhanced cell tropism when compared to native virus particles.

18. A virus like particle (VLP) comprising:
(i) a non-viral RNA; and
(ii) an artificial RNA cassette, wherein said artificial RNA cassette comprises:
one or more packaging signals arranged in series and separated by a non-coding viral nucleic acid, said one or more packaging signals comprising a nucleic acid loop domain comprising a nucleotide binding motif for cognate viral capsid protein(s), and a nucleic acid stem domain comprising a double stranded region by intra-molecular base pairing,
wherein:
a) said VLP is a Hepatitis B virus VLP, said one or more packaging signals is from Hepatitis B virus and said nucleotide binding motif comprises the nucleotide sequence RGAG, wherein R is G or A; or
b) said VLP is a Satellite Tobacco Necrosis Virus VLP, said one or more packaging signals is from Satellite Tobacco Necrosis Virus, and said nucleotide binding motif comprises the nucleotide sequence AXXA or AXXXA, wherein X is any nucleotide base; and
wherein said artificial RNA cassette, when contacted with a plurality of cognate viral capsid proteins, assembles said cognate viral capsid proteins into a VLP that protects said packaging signals contained within said VLP from ribonuclease digestion.

19. A vaccine or immunogenic composition comprising the virus like particle of claim 18.

20. The VLP according to claim 18, wherein said artificial RNA cassette is a non-replicating nucleic acid.

21. The VLP according to claim 18, wherein said VLP provokes an immune response similar to an immune response of a native virus particle when administered to an animal subject.

22. The VLP according to claim 18, wherein said artificial RNA cassette does not comprise a protein-encoding nucleic acid.

23. The VLP according to claim 18, wherein said artificial RNA cassette comprises at least 2, at least 3, at least 4 or at least 5 nucleic acid packaging signals.

24. The VLP according to claim 18, wherein said non-coding viral nucleic acid separating said one or more packaging signals is at least 5 nucleotides in length.

25. The VLP according to claim 18, wherein
said nucleic acid loop domain is at least 4 nucleotides in length;
said nucleic acid stem domain is at least 5 base pairs (bp) in length;
said artificial RNA cassette is at least 50 nucleotides in length; and/or
said artificial RNA cassette is between 50 and 1000 nucleotides in length.

26. The VLP according to claim 18, wherein said artificial RNA cassette comprises at least one, two or three packaging signals from Hepatitis B virus, wherein one or more of said at least one, two or three packaging signals from Hepatitis B includes the nucleotide binding motif RGAG.

27. The VLP according to claim 18, wherein said artificial RNA cassette comprises at least one Hepatitis B packaging signal, wherein each of said Hepatitis B packaging signals includes the binding motif RGAG.

28. The VLP according to claim 18, wherein said artificial RNA cassette comprises:
   i) a nucleic acid molecule comprising the nucleotide sequence GUUUGUUUAAAGACUGGGAG-GAGUUGGGGAGGAG, as set forth by SEQ ID NO: 1;
   ii) a nucleic acid molecule comprising at least 25% sequence identity to the nucleotide sequence of SEQ ID NO: 1 and comprising the nucleotide binding motif GGGAG;
   iii) a nucleic acid molecule comprising the nucleotide sequence GGGCCCU-CUGACAGUUAAUGAAAAAGGAGAUUAAAA UUAAUUAUG CCU, as set forth by SEQ ID NO: 2;
   iv) a nucleic acid molecule comprising at least 25% sequence identity to the nucleotide sequence of SEQ ID NO: 2 and comprising the nucleotide binding motif GAAAAAGGAG;
   v) a nucleic acid molecule comprising the nucleotide sequence GGCUGGCAUUC-UAUAUAAGAGAGAAACUACACGC, as set forth by SEQ ID NO: 3;
   vi) a nucleic acid molecule comprising at least 25% sequence identity to the nucleotide sequence of SEQ ID NO: 3 and comprising the nucleotide binding motif AUAUAAGAG;
   vii) a nucleic acid molecule comprising SEQ ID NO: 1;
   viii) a nucleic acid molecule comprising SEQ ID NO: 2;
   ix) a nucleic acid molecule comprising SEQ ID NO: 3; or
   x) a nucleic acid molecule comprising SEQ ID NO: 4.

29. The VLP according to claim 18, wherein said artificial RNA cassette further comprises a transcription cassette comprising a nucleic acid molecule adapted to transcribe a nucleic acid encoding a polypeptide or a functional RNA.

30. The VLP according to claim 29, wherein said transcription cassette comprises a promoter sequence and termination sequence to enable expression of said nucleic acid molecule encoding said polypeptide or functional RNA.

31. The VLP according to claim 30, wherein said polypeptide is a therapeutic polypeptide.

32. The VLP according to claim 30, wherein said functional RNA is an mRNA encoding a therapeutic polypeptide, an antisense oligonucleotide or an siRNA.

\* \* \* \* \*